US009751908B2

(12) United States Patent
Pereira

(10) Patent No.: US 9,751,908 B2
(45) Date of Patent: Sep. 5, 2017

(54) CONVERGENT PROCESSES FOR PREPARING MACROLIDE ANTIBACTERIAL AGENTS

(71) Applicant: CEMPRA PHARMACEUTICALS, INC., Chapel Hill, NC (US)

(72) Inventor: David Eugene Pereira, Apex, NC (US)

(73) Assignee: CEMPRA PHARMACEUTICALS, INC., Chapel Hill, NC (US)

( * ) Notice: Subject to any disclaimer, the term of this patent is extended or adjusted under 35 U.S.C. 154(b) by 0 days.

(21) Appl. No.: 14/774,843

(22) PCT Filed: Mar. 15, 2014

(86) PCT No.: PCT/US2014/029932
§ 371 (c)(1),
(2) Date: Sep. 11, 2015

(87) PCT Pub. No.: WO2014/145210
PCT Pub. Date: Sep. 18, 2014

(65) Prior Publication Data
US 2016/0046660 A1 Feb. 18, 2016

Related U.S. Application Data

(60) Provisional application No. 61/786,914, filed on Mar. 15, 2013.

(51) Int. Cl.
C07H 17/08 (2006.01)
(52) U.S. Cl.
CPC .................... C07H 17/08 (2013.01)
(58) Field of Classification Search
CPC ..................................... C07H 17/08
See application file for complete search history.

(56) References Cited

U.S. PATENT DOCUMENTS

| | | |
|---|---|---|
| 1,354,753 A | 10/1920 | Howard |
| 2,180,006 A | 11/1939 | Hasche |
| 3,668,282 A | 6/1972 | Below |
| 3,843,787 A | 10/1974 | Fabrizio |
| 4,312,866 A | 1/1982 | Caruso |
| 4,331,803 A | 5/1982 | Watanabe |
| 4,474,768 A | 10/1984 | Bright |
| 4,742,049 A | 5/1988 | Baker |
| 4,886,792 A | 12/1989 | Djokic |
| 4,990,602 A | 2/1991 | Morimoto |
| 5,211,955 A | 5/1993 | Legros |
| 5,444,051 A | 8/1995 | Agouridas |
| 5,527,780 A | 6/1996 | Agouridas |
| 5,543,400 A | 8/1996 | Agouridas |
| 5,614,614 A | 3/1997 | Agouridas |
| 5,635,485 A | 6/1997 | Agouridas |
| 5,656,607 A | 8/1997 | Agouridas |
| 5,747,467 A | 5/1998 | Agouridas |
| 5,760,233 A | 6/1998 | Agouridas |
| 5,770,579 A | 6/1998 | Agouridas |
| 5,834,428 A | 11/1998 | Drucker |
| 5,985,844 A | 11/1999 | Heck |
| 6,011,142 A | 1/2000 | Bonnet |
| 6,020,521 A | 2/2000 | Randolph |
| 6,028,181 A | 2/2000 | Or |
| 6,096,714 A | 8/2000 | Agouridas |
| 6,096,922 A | 8/2000 | Lal |
| 6,121,432 A | 9/2000 | Bonnet |
| 6,270,768 B1 | 8/2001 | OConnell |
| 6,313,101 B1 | 11/2001 | Denis |
| 6,395,300 B1 | 5/2002 | Straub et al. |
| 6,395,710 B1 | 5/2002 | Chu |
| 6,407,074 B1 | 6/2002 | Bronk |
| 6,407,257 B1 | 6/2002 | Agouridas et al. |
| 6,420,535 B1 | 7/2002 | Phan |
| 6,437,106 B1 | 8/2002 | Stoner |
| 6,440,941 B1 | 8/2002 | Denis |
| 6,455,505 B2 | 9/2002 | Agouridas |
| 6,515,116 B2 | 2/2003 | Suh |
| 6,555,524 B2 | 4/2003 | Kaneko |
| 6,664,238 B1 | 12/2003 | Su |
| 6,777,393 B2 | 8/2004 | Bronk |
| 6,809,188 B1 | 10/2004 | Suh |
| 6,849,608 B2 | 2/2005 | Su |
| 6,890,907 B2 | 5/2005 | Speirs |
| 7,163,924 B2 | 1/2007 | Burger |
| 7,332,476 B2 | 2/2008 | Burger |
| 7,375,234 B2 | 5/2008 | Sharpless |
| 7,419,961 B2 | 9/2008 | Napoletano |
| 7,601,695 B2 | 10/2009 | Liang et al. |
| 7,951,905 B2 | 5/2011 | Schweizer et al. |

(Continued)

FOREIGN PATENT DOCUMENTS

| | | |
|---|---|---|
| CN | 1354753 | 6/2002 |
| CN | 101045063 | 10/2007 |

(Continued)

OTHER PUBLICATIONS

PCT Search Report prepared for PCT/US2014/029932, mailed Aug. 11, 2014.
Baker, William R., et al. "Modification of macrolide antibiotics. Synthesis of 11-deoxy-11-(carboxyamino)-6-O-methylerythromycin A 11, 12-(cyclic esters) via an intramolecular Michael reaction of O-carbamates with an. aplpha.,. beta.-unsaturated ketone." The Journal of Organic Chemistry 53.10 (1988): 2340-2345.
Birkenmeyer, R. D., Kroll, S. J., Lewis, C., Stern, K. F., and Zurenko, G. E. 'Synthesis and Antibacterial Activity of Clindamycin Analogues: Pirlimycin, a Potent Antibacterial Agent', Journal of Medicinal Chemistry, vol. 27, No. 2, 1984, 216-223.

(Continued)

Primary Examiner — Layla Berry
(74) Attorney, Agent, or Firm — Brannon Sowers & Cracraft PC

(57) ABSTRACT

The invention described herein relates to processes for preparing ketolide antibacterial agents. In particular, the invention relates to intermediates and processes for preparing ketolides that include a 1,2,3-triazole substituted side chain.

17 Claims, No Drawings

(56) References Cited

U.S. PATENT DOCUMENTS

| | | |
|---|---|---|
| 8,012,943 B2 | 9/2011 | Duffield |
| 8,247,394 B2 | 8/2012 | Fernandes |
| 8,791,080 B2 | 7/2014 | Fernandes |
| 8,796,232 B2 | 8/2014 | Fernandes |
| 9,051,346 B2 | 6/2015 | Pereira |
| 9,200,026 B2 | 12/2015 | Liang |
| 2002/0028781 A1 | 3/2002 | Agouridas |
| 2002/0044967 A1 | 4/2002 | Yamashita |
| 2003/0143162 A1 | 7/2003 | Speirs |
| 2003/0176327 A1 | 9/2003 | Cassell |
| 2004/0009930 A1 | 1/2004 | Su |
| 2004/0014685 A1 | 1/2004 | Mercep |
| 2005/0009764 A1 | 1/2005 | Burger et al. |
| 2005/0014706 A1 | 1/2005 | Falzari |
| 2005/0022242 A1 | 1/2005 | Rosetti |
| 2005/0153905 A1 | 7/2005 | Burger |
| 2005/0209172 A1 | 9/2005 | Woo |
| 2005/0222427 A1 | 10/2005 | Sharpless |
| 2006/0076536 A1 | 4/2006 | Barshied |
| 2006/0100164 A1 | 5/2006 | Liang |
| 2006/0264385 A1 | 11/2006 | Wang |
| 2007/0015719 A1 | 1/2007 | Jenkins |
| 2007/0167382 A1 | 7/2007 | Finkelstein |
| 2007/0197518 A1 | 8/2007 | Johnson |
| 2007/0281894 A1 | 12/2007 | Gant |
| 2008/0113926 A1 | 5/2008 | Ivezic |
| 2008/0132546 A1 | 6/2008 | Basarab et al. |
| 2008/0221048 A1 | 9/2008 | Woo |
| 2008/0227730 A1 | 9/2008 | Mutak |
| 2008/0241959 A1 | 10/2008 | Culic |
| 2008/0287376 A1 | 11/2008 | Das |
| 2009/0005325 A1 | 1/2009 | Bas |
| 2009/0075916 A1 | 3/2009 | Upadhyay |
| 2009/0076253 A1 | 3/2009 | Kashimura |
| 2009/0087389 A1 | 4/2009 | Leonard |
| 2009/0156517 A1 | 6/2009 | Zhang |
| 2009/0209547 A1 | 8/2009 | Kim |
| 2010/0143505 A1 | 6/2010 | Gant et al. |
| 2010/0216731 A1 | 8/2010 | Pereira |
| 2011/0119604 A1 | 5/2011 | Lo |
| 2011/0195920 A1 | 8/2011 | Fernandes |
| 2012/0071429 A1 | 3/2012 | Duffield |
| 2012/0172323 A1 | 7/2012 | Fernandes |
| 2012/0231995 A1 | 9/2012 | Beck |
| 2013/0011453 A1 | 1/2013 | Latta |
| 2013/0018008 A1 | 1/2013 | Pereira |
| 2013/0045937 A1 | 2/2013 | Pereira |
| 2013/0053362 A1 | 2/2013 | Castro |
| 2013/0102523 A1 | 4/2013 | Bartizal |
| 2013/0156705 A1 | 6/2013 | Zhang |
| 2013/0164351 A1 | 6/2013 | Fernandes |
| 2013/0172280 A1 | 7/2013 | Pereira |
| 2013/0345410 A1 | 12/2013 | Liang |
| 2014/0088062 A1 | 3/2014 | Pereira |
| 2014/0148431 A1 | 5/2014 | Patel |

FOREIGN PATENT DOCUMENTS

| | | |
|---|---|---|
| EP | 0248279 A2 | 12/1987 |
| EP | 1024145 A2 | 8/2000 |
| EP | 0680967 A1 | 2/2001 |
| EP | 1167375 | 1/2002 |
| GB | 891817 | 3/1962 |
| JP | S59175414 | 10/1984 |
| JP | 06220082 | 8/1994 |
| JP | 08053489 | 2/1996 |
| JP | 2000507573 | 6/2000 |
| JP | 2000229993 | 8/2000 |
| JP | 2000351794 | 12/2000 |
| JP | 2002514197 | 5/2002 |
| JP | 2004502736 | 1/2004 |
| JP | 2006528667 | 12/2006 |
| JP | 2007536371 | 12/2007 |
| JP | 2008519788 | 6/2008 |
| JP | 2008526948 | 7/2008 |
| JP | 2008534504 | 8/2008 |
| JP | 2009500356 | 1/2009 |
| JP | 2009502788 | 1/2009 |
| JP | 5914335 | 5/2016 |
| RU | 2230748 | 6/2004 |
| WO | 9736912 | 10/1997 |
| WO | 9830574 A1 | 7/1998 |
| WO | 9856800 A1 | 12/1998 |
| WO | 9921866 A1 | 5/1999 |
| WO | 9928311 A1 | 6/1999 |
| WO | 0012521 A1 | 3/2000 |
| WO | 0031099 A1 | 6/2000 |
| WO | 0044761 A2 | 8/2000 |
| WO | 0062783 A2 | 10/2000 |
| WO | 0110878 A1 | 2/2001 |
| WO | 0250092 A1 | 6/2002 |
| WO | 03004509 | 1/2003 |
| WO | 03004509 A | 1/2003 |
| WO | 03072141 A1 | 9/2003 |
| WO | 2004080391 A2 | 9/2004 |
| WO | 2004101587 | 11/2004 |
| WO | 2005074945 | 8/2005 |
| WO | 2005105821 | 11/2005 |
| WO | 2005108412 | 11/2005 |
| WO | 2006050941 | 5/2006 |
| WO | 2006050942 | 5/2006 |
| WO | 2006087642 | 8/2006 |
| WO | 2007008537 | 1/2007 |
| WO | 2007059307 A2 | 5/2007 |
| WO | 2007060627 | 5/2007 |
| WO | 20070143507 | 12/2007 |
| WO | 2009055557 A1 | 4/2009 |
| WO | 2010048599 | 4/2010 |
| WO | 2010048600 | 4/2010 |
| WO | 2010048601 | 4/2010 |
| WO | 2011008193 | 1/2011 |
| WO | 2011032052 | 3/2011 |
| WO | 2011112864 A1 | 9/2011 |
| WO | 2011119604 | 9/2011 |
| WO | 2011146829 | 11/2011 |
| WO | 2012042534 | 4/2012 |
| WO | 2013148891 | 10/2013 |
| WO | 2014145210 | 9/2014 |
| WO | 2014152326 | 9/2014 |
| WO | 2014165792 | 10/2014 |
| WO | 2015181723 | 12/2015 |

OTHER PUBLICATIONS

Champney et al., 'Structure-Activity Relationships for Six Ketolide Antibiotics', Current Microbiology, 42:203-10 (2001).

Denis et al., beta-Keto-Ester Chemistry and Ketolides. Snythesis and antibacterial Activity of 2-Halogeno, 2-Methyl and 2,3 Enol-Ether Ketolides, Bioorganic & Medicinal Chemistry Letters, 10:2019-22 (2000).

Djokic, S. et al., 'Erythromycin Series. Part 11. Ring Expansion of Erythromycin A Oxime by the Beckmann Rearrangement.' J. Chem. Soc Perkin Trans 1., 1881-1890 (1986).

LeMahieu, R. A., Carson, M., and Kierstead, R. W., 'Glycoside Cleavage Reactions on erythromycin A. Preparation of Erythronolide A,' Journal of Medicinal Chemistry, vol. 17, No. 9, 1974, 953-956.

Liang C. H. et al., 'Synthesis and biological activity of new 5-0-sugar modified ketolide and 2-fluoro-ketolide antibiotics,' Bioorganic & Medicinal Chemistry Letters, Pergamon, Elsevier Science, GB, vol. 15, No. 5, Mar. 1, 2005, pp. 1307-1310.

Or et al., 'Design, Synthesis, and Antimicrobial Activity of 6-0-Substituted Ketolides Active Against Resistant Respiratory Tract Pathogens', J. Med. Chem., 43:1045-49 (2000).

PCT Search Report and Written Opinion for PCT/US2011/037330 completed Aug. 26, 2011.

Phan, L.T. et al., 'Synthesis of 2-Fluoro-6-O-propargyl-11,12-carbamate Ketolides. A Novel Class of Antibiotics,' Org. Ltrs., 2:2951-2954 (2000).

Plata, Daniel J., et al. "The synthesis of ketolide antibiotic ABT-773 (cethromycin)." Tetrahedron 60.45 (2004): 10171-10180.

(56) References Cited

OTHER PUBLICATIONS

Romero et al., 'An efficient entry to new sugar modified ketolide antibiotics' Tetrahedron Letters, vol. 46, 2005, pp. 1483-1487.
Rostovtsev, V.V. et al., 'A Stepwise Huisgen Cycloaddition Process: Copper(I)=Catalyzed Regioselective 'Ligation' of Azides and Terminal Alkynes,' Angew. Chem. Int. Ed., 41: 2596-2599 (2002).
Tome et al. 'Peptidotriazoles on Solid Phase: [1,2,3]-Triazoles by Regiospecific Copper(I)-Catalyzed 1,3-Dipolar Cycloadditions of Terminal Alkynes to Azides', J. Org. Chem., 67:3057-64 (2002).
Vince, R., Almquist, R. G., Ritter, C. L., and Daluge, S., Antimicrobial Agents and Chemotherapy, vol. 8, No. 4, 1975, 439-443.
Zhenkun Ma & Peter A. Nemoto "Discovery and Development of Ketolides as a New Generation of MacrolideAntimicrobial Agents" Curr Med Chem-Anti-Infective Agents 1:15-34 (2002).
Bebear, C.M., et al., In vitro activity of trovafloxacin compared to those of five antimicrobials against mycoplasmas including Mycoplasma hominis and Ureaplasma urealyticum fluoroquinolone-resistant isolates that have been genetically characterized, Antimicrob Agents Chemother 44:2557-2560 (2000).
Berge, Stephen M., et al., "Pharmaceutical Salts", 1977, Journal of Pharmaceutical Sciences, vol. 66, No. 1, pp. 1-19.
Bermudez, Luiz E., et al., "Telithromycin is Active Against *Mycobacterium avium* in Mice Despite Lacking Significant Activity in Standard in Vitro and Macrophage Assays and Is Associated with Low Frequency of Resistance During Treatment", 2001, Antimicrobal Agents and Chemotherapy, vol. 45, No. 8, pp. 2210-2214.
Celebuski, J.E. et al., 'Chemical Modification of Erythromycin: Novel Reaction Observed by Treatment with Metalloporphyrins', vol. 35, No. 23, pp. 3837-3850, 1994, Elsevier Science Ltd.
Cynamon, M. H., et al., "Activity of ABT-773 Against *Mycobacterium avium* Complex in the Beige Mouse Model", 2000, Antimicrobal Agents and Chemotherapy, vol. 44, No. 10, pp. 2895-2896.
Hill, D.R. et al., 'Novel Macrolides via meso-Tetraarylmetalloporphyrin Assisted Oxidation', Tetrahedron Letters, vol. 37, No. 6, pp. 787-790, 1996, Elsevier Science Ltd.
Holzer, G., et al., "Kα1,2 and Kβ1,3 X-Ray Emission Lines of the 3d Transition Metals", Dec. 1997, Physical Review, vol. 56, No. 6, pp. 4554-4568.
Inglesby, Thomas V., et al., "Anthrax as a Biological Weapon, 2002", 2002, Journal of the American Medical Association, vol. 287, No. 17, pp. 2236-2252.
Laine, Loren, et al., "Prospective comparison of H&E, Giemsa and Genta stains for the diagnosis of Helicobacter pylori," 1997, Gastrointestinal Endoscopy, vol. 45, No. 6, pp: 463-467.
Lee, Adrian, et al., "A standard mouse model of Helicobacter pylori infection: introducing the Sydney Strain," 1997, Gastroenterology, vol. 112, pp. 1386-1397.
Morimoto S. et al., 'Chemical Modification of Erythromycins VII. Molecular Rearrangement Observed During Chemical Modification Study of the Desosamine Unit of Erythromycins', Heterocycles, Elsevier Science Publishers, vol. 31, No. 2, Jan. 1, 1990, pp. 305-319.
Nilius et al.: 'Ketolides: the future of the macrolides?' Current Opinion in Pharmacology, [Online] vol. 2, Jan. 14, 2002, pp. 1-8 Retrieved from the Internet: <URL:http://www.sciencedirect.com/science/article/pii/S1471489202001984>.
Patel, Ramesh N., "Stereoselective Biocatalysis", 2000, Bristol-Myers Squibb Research Institute; pp. 775-797.
Barcia-Macay, Maritza, et al., 'Pharmacodynamic Evaluation of the Intracellular Activities of Antibiotics Against *Staphylococcus aureus* in a Model of THP-1 Macrophages', 2006, Antimicrobial Agents and Chemotherapy. vol. 50, No. 3, pp. 841-851.
Bermudez, Luiz E., et al., "EDP-420, a Bicyclolide (Bridged Bicyclic Macrolide), Is Active Against *Mcyobacterium avium*", 2007, Antimicrobal Agents and Chemotherapy, vol. 51, No. 5, pp. 1666-1670.
Crone, Julia, et al., "Evaluation of a monoclonal antibody-based test for detection of Helicobacter pylori-Specific Antigen in stool samples from mice," Jul. 2004, Clinical and Diagnostic Laboratory Immunology, vol. 11, No. 4, pp. 799, 800.
Drusano, G. L., et al., "Is 60 Days of Ciprofloxacin Adminstration Necessary for Postexposure Prophylaxis for Bacillus Anthracis?", 2008, Antimicrobial Agents and Chemotherapy. vol. 52, No. 11, pp. 3973-3979.
Duffy, L., et al., Fluoroquinolone resistance in Ureaplasma parvum in the United States, J Clin Microbiol 44:1590-1591 (2006).
Jensen, J.S., et al., Azithromycin Treatment Failure in Mycoplasma genitaliumPositive Patients with Nongonococcal Urethritis Is Associated with Induced Macrolide Resistance, Clin Infect Dis 47:1546-53 (2008).
Lemaire, Sandrine, et al., "Cellular Accumulation and Pharmacodynamic Evaluation of the Intracellular Activity of CEM-101, a Novel Fluoroketolide, Against *Staphylococcus aureus*, Listeria Monocytogenes and Legionella Pneumophila in Human THP-1 Macrophages", 2009, Antimicrobial Agents and Chemotherapy. vol. 53, No. 9, pp. 3734-3743.
Li, X., et al., Emerging macrolide resistance in Mycoplasma pneumoniae in children: detection and characterization of resistant isolates, Pediatr Infect Dis J, 28:693-696 (2009).
Physicians' Desk Reference, p. 2905, (2007).
Vennerstrom, Jonathan L., et al., "Identification of an Antimalarial Synthetic Trioxolane Drug Development Candidate", 2004, Letters to Nature, vol. 430, pp. 900-904.
Waites, K.B., et al., Mycoplasmas and ureaplasmas as neonatal pathogens, Clin Microbiol Rev 18:757-89 (2005).
Zuckerman, "Macrolides and ketolides: azithromycin, clarithromycin, telithromycin", Infectious Disease Clinics of North America, vol. 18, (2004), pp. 621-649.
Jones et al.: 'MIC Quality Control Guidelines and Disk Diffusion Test Optimization for CEM-101, a Novel Fluoroketolide' Journal of Clinical Microbiology vol. 48, No. 4, Dec. 30, 2009, pp. 1470-1473.
PCT International Search Report and Written Opinion for PCT/US2011/029424, mailed May 25, 2011.
Feder, P. I., et al., 1991. Statistical Analysis of Dose-Response Experiments by Maximum Likelihood Analysis and teratively Reweighted Nonlinear Least Squares Regression Techniques, 1991, Drug Information Journal, vol. 28, pp. 323-334.
Caira MR, "Crystalline polymorphism of orgainic compounds," Design of Organic Solids, Topics in Current Chemistry, Springer Berlin Heidelberg, 1998, p. 163-208.
Pathak et al., "Enzymatic Protecting Group Techniques in Organic Synthesis," Stereosel, Biocatal., 2000; pp. 775-797.
Katz, Leonard, and Gary W. Ashley. "Translation and protein synthesis: macrolides." Chemical reviews 105.2 (2005): 499-528.
Threlfall, Terence L. "Analysis of organic polymorphs. A review." Analyst 120.10 (1995): 2435-2460.
Petit, Samuel, and G?? © rard Coquerel. "The amorphous state." Polymorphism: In the Pharmaceutical Industry 10 (2006): 1.
Organic Compounds Crystal Manufacture Handbook—Principles and Knowhow, 2008, pp. 57 to 84.
Salzer, W. (2005). Antimicrobial-resistant gram-positive bacteria in PD peritonitis and the newer antibiotics used to treat them. Peritoneal Dialysis International, 25(4), 313-319.
International Search Report Written Opinion for PCT/US2008/080936 dated Dec. 8, 2008.
Hancock, Bruno C., Sheri L. Shamblin, and George Zografi. "Molecular mobility of amorphous pharmaceutical solids below their glass transition temperatures." Pharmaceutical research 12.6 (1995): 799-806.
Akshizawa, Kazuhide, "Physico-Chemical Studies on the molecular Details of Drug Crystals," Phar Tech Japan, 2002, vol. 18, No. 10. pp. 81-96.
PCT Search Report and Written Opinion prepared for PCT/US2009/061978 dated Dec. 9, 2009.
European Search Report for EP 09 82 2827, dated Mar. 21, 2012.
International Search Report for PCT/US2009/061977, dated Dec. 23, 2009, (3 pages).
PCT Search Report/Written Opinion prepared for PCT/US2010/048540, dated Oct. 21, 2010.

(56) References Cited

OTHER PUBLICATIONS

Bym, S., Pfeiffer, R., Ganey, M., Hoiberg, C., & Poochikian, G. (1995). Pharmaceutical solids: a strategic approach to regulatory considerations. Pharmaceutical research, 12(7), 945-954.

Sumerkan, B., Aygen, B., Doganay, M., & Sehmen, E. (1996). Antimicrobial susceptibility of Bacillus anthracis against macrolides. Salisbury Med Bull Supplement, 87, 138.
Maurin, M., Mersali, N. F., & Raoult, D. (2000). Bactericidal activities of antibiotics against intracellular Francisella ularensis. Antimicrobial agents and chemotherapy, 44(12), 3428-3431.
Luna, V. A., King, D. S., Gulledge, J., Cannons, A. C., Amuso, P. T., & Cattani, J. (2007). Susceptibility of Bacillus anthracis, Bacillus cereus, Bacillus mycoides, Bacillus pseudomycoides and Bacillus thuringiensis to 24 antimicrobials using Sensititre??® automated microbroth dilution and Etest??® agar gradient diffusion methods. Journal of antimicrobial chemotherapy, 60(3), 555-567.
Barthel, D., Schlitzer, M., & Pradel, G. (2008). Telithromycin and quinupristin-dalfopristin induce delayed death in Plasmodium falciparum. Antimicrobial agents and chemotherapy, 52(2), 774-777.
Still, J. G., et al. “Single Oral Dose Pharmacokinetics and Safety of CEM-101 in Healthy Subjects.” 46th Annual Meeting. ldsa, 2008.
Lee, Joo Hyun, and Myung Gull Lee. “Dose-dependent pharmacokinetics of telithromycin after intravenous and oral administration to rats: contribution of intestinal first-pass effect to low bioavailability.” J. Pharm. Pharm. Sci 10 (2007): 37-50.
Chen, M., Muri, E. M., Jacob, T. M., & Williamson, J. S. (2003). Synthesis and bioactivity of erythromycin derivatives. Medicinal chemistry research, 12(3), 111-129.
Kerdesky, F. A., Premchandran, R., Wayne, G. S., Chang, S. J., Pease, J. P., Bhagavatula, L., . . . & King, S. A. (2002). Synthesis of 2'-O-Benzoyl-3-keto-6-O-propargyl-11, 12-carbamoyl Erythromycin A. Organic process research & development, 6(6), 869-875.
Zhu, Z. J., Krasnykh, O., Pan, D., Petukhova, V., Yu, G., Liu, Y., . . . & Franzblau, S. G. (2008). Structure-activity relationships of macrolides against Mycobacterium tuberculosis. Tuberculosis, 88, S49-S63.
Putnam S. D. et al, Antimicrobial Characterization of Solithromycin (Cem-101), A Novel Fluroroketolide: Activity Against Staphlococci and Enterococci. International Journal of Antimicrobial Agents, vol. 37, No. 1, 2011, pp. 39-45.
Written Opinion, Singapore Application No. 11201405895U: Intellectual Property Office of Singapore, dated Mar. 31, 2015, 6 pages.
Database WPI Week 200822 Thomson Scientific, London, GB; AN 2008-D02982.
Zimmermann, Torsten, et al. “Comparative tolerability of intravenous azithromycin, clarithromycin and erythromycin in healthy volunteers.” Clinical Drug Investigation 21.8 (2001): 527-536.
Luke, D. R., and G. Foulds. “Toleration of intravenous azithromycin.” The Annals of pharmacotherapy 31.9 (1997): abstract only.
Cannon, John B., N. Adeyinka Williams, and Karen J. Papp. “Reduction of pain on intravenous infusion with bile salt formulations for a macrolide antibiotic.” International journal of pharmaceutics 114.1 (1995): abstract only.
Lu, Yan, YanJiao Wang, and Xing Tang. “Formulation and thermal sterile stability of a less painful intravenous clarithromycin emulsion containing vitamin E.” International journal of pharmaceutics 346.1 (2008): abstract only.
Llano-Sotelo, B., D. Klepacki, and A. S. Mankin. 2008. Binding and action of CEM-10, a new macrolide/ketolide in development for treating infections with macrolide-resistant and macrolide-susceptible bacteria. 48th Annu. Intersci. Conf. Antimicrob. Agents Chemother./46th Infect. Dis. Soc. Am. Ann. Meet., abstr. F1-3983.
International Search Report for PCT/US2015/015353, dated May 14, 2015, (8 pages).
Ferris, C. F., Lu, S. F., Messenger, T., Guillon, C. D., Heindel, N., Miller, M., . . . & Simon, N. G. (2006). Orally active vasopressin V1a receptor antagonist, SRX251, selectively blocks aggressive behavior. Pharmacology Biochemistry and Behavior, 83(2), 169-174.
Amsden, G. W. “Anti-inflammatory effects of macrolides—and underappreciated benefit in the treatment of community-acquired respiratory tract infections and chronic inflammatory pulmonary conditions?.” Journal of Antimicrobial Chemotherapy 55.1 (2005): 10-21.
de Jong, J. T., et al. “[Large-scale, acute, bacterial gastroenteritis caused by the enterotoxin of *Staphylococcus aureus* after a barbecue].” Nederlands tijdschriff voor geneeskunde 148.43 (2004): 2136-2140.
Raj, Pushker. “Pathogenesis and laboratory diagnosis of *Escherichia coli*—associated enteritis.” Clinical microbiology Newsletter 15.12 (1993): 89-93.
Ikeue, T., et al. “[Pneumonia caused by Nocardia nova].” Nihon Kokyuki Gakkai zasshi=the journal of the Japanese Respiratory Society 39.7 (2001): 492-497.
Thakkar, Shyam, and Radheshyam Agrawal. “A case of *Staphylococcus aureus* enterocolitis: a rare entity.” Gastroenterology & hepatology 6.2 (2010): 115-117.
Wain, Harry, and Paul A. Blackstone. “Staphylococcal Gastroenteritis.” The American journal of digestive diseases 1.10 (1956): 424-429.
Wain, Harry, and Paul A. Blackstone. “Staphylococcal Gastroenteritis.” The American journal of digestive diseases 1.10 (1956): 424.
Boyce, Thomas G., “Staphylococcal Food Poisoning,” Merck Manuals (2015) 2 pages.
Lv Yang et al., “Polymorphic Drugs.” Oct. 31, 2009, pp. 110-111.
Le Loir, Yves, Florence Baron, and Michel Gautier. “*Staphylococcus aureus* and food poisoning.” Genet Mol Res 2.1 (2003): 63-76.
Brittain HG editor “Polymorphism in pharmaceutical solids”, Chapter 1, p. 1-10 (Grant DJW) and Chapter 5, p. 183-226 (1999).
Graeme, A. O'May, Nigel Reynolds, and George T. Macfarlane. “Effect of pH on an in vitro model of gastric microbiota in enteral nutrition patients.” Applied and environmental microbiology 71.8 (2005): 4777-4783.
Cotter, Paul D., and Colin Hill. “Surviving the acid test: responses of gram-positive bacteria to low pH.” Microbiology and Molecular Biology Reviews 67.3 (2003): 429-453.
Lyczak, J. B., Cannon, C. L., & Pier, G. B. (2002). Lung infections associated with cystic fibrosis. Clinical microbiology reviews, 15(2), 194-222.
Denis, Alexis, et al. “Synthesis and antibacterial activity of HMR 3647 a new ketolide highly potent against erythromycin-resistant and susceptible pathogens.” Bioorganic & medicinal chemistry letters 9.21 (1999): 3075-3080.
Bryskier, A. “Ketolides—telithromycin, an example of a new class of antibacterial agents.” Clinical Microbiology and Infection 6.12 (2000): 661-669.
Morimoto, Shigeo, et al. “Chemical modification of erythromycins. I. Synthesis and antibacterial activity of 6-O-methylerythromycins A.” The Journal of antibiotics 37.2 (1984): 187-189.
Hallgren, Anita, et al. “Antimicrobial susceptibility patterns of enterococci in intensive care units in Sweden evaluated by different MIC breakpoint systems.” Journal of Antimicrobial Chemotherapy 48.1 (2001): 53-62.
Fernandes, P., et al. Intravenous Formulation of Solithromycin, a Painless Macrolide Antibiotic in a Rabbit Intravenous Injection Model, 2011, 5 pages.
Allen Loyd V Jr, Acidifying Agents, Featured Excipient. International Journal of Pharmaceutical Compounding, Dec. 13, 1999, vol. 3, No. 4, pp. 309 (abstract only).
Yatin R. G. et al., Excipients for Protein Drugs. Excipient Development for Pharmaceutical, Biotechnology, and Drug Delivery Systems, Jul. 28, 2006, pp. 299-300.
Fernandes, P., et al. “Solithromycin Macrolide Antibiotic.” Drugs of the Future 36.10 (2011): 751-758.
Raoul, Jennifer M., Marc R. Peterson, and Theresa C. Peterson. “A novel drug interaction between the quinolone antibiotic ciprofloxacin and a chiral metabolite of pentoxifylline.” Biochemical pharmacology 74.4 (2007): 639-646.

CONVERGENT PROCESSES FOR PREPARING MACROLIDE ANTIBACTERIAL AGENTS

CROSS-REFERENCE TO RELATED APPLICATION

This application is a U.S. national application under 37 C.F.R. §371(b) of International Application Serial No. PCT/US2014/029932 filed on Mar. 15, 2014, which claims the benefit under 35 U.S.C. §119(e), of U.S. Provisional Application No. 61/786,914, filed on Mar. 15, 2013, the entire disclosures of which are incorporated herein by reference.

TECHNICAL FIELD

The invention described herein relates to processes for preparing ketolide antibacterial agents. In particular, the invention relates to intermediates and processes for preparing ketolides that include a 1,2,3-triazole substituted side chain.

BACKGROUND AND SUMMARY

The use of macrolides for various infectious diseases is well known. Erythromycin was the first compound of this class to be introduced into clinical practice. Since then, additional macrolides, including ketolides have garnered much attention for their ability to treat a wide range of disease states. In particular, macrolides are an important component of therapies for treating bacterial, protozoal, and viral infections. In addition, macrolides are often used in patients allergic to penicillins.

Illustrative of their wide ranging uses, macrolide compounds have been found to be effective for the treatment and prevention of infections caused by a broad spectrum of bacterial and protozoal pathogens. They are also useful for treating respiratory tract infections and soft tissue infections. Macrolide antibiotics are found to be effective on beta-hemolytic streptococci, pneumococci, staphylococci, and enterococci. They are also found to be effective against *mycoplasma*, mycobacteria, some *rickettsia*, and *chlamydia*.

Macrolide compounds are characterized by the presence of a large lactone ring, which is generally a 14, 15, or 16-membered macrocyclic lactone, to which one or more saccharides, including deoxy sugars such as cladinose and desosamine, may be attached. For example, erythromycin is a 14-membered macrolide that includes two sugar moieties. Spiramycin belongs to a second generation of macrolide compounds that include a 16-membered ring. Third generation macrolide compounds include for example semi-synthetic derivatives of erythromycin A, such as azithromycin and clarithromycin. Finally, ketolides represent a newer class of macrolide antibiotics that have received much attention recently due to their acid stability, and most importantly due to their excellent activity against organisms that are resistant to other macrolides. Like erythromycins, ketolides are 14-membered ring macrolide derivatives characterized by a keto group at the C-3 position (Curr. Med. Chem., "Anti-Infective Agents," 1:15-34 (2002)). Ketolide compounds are also currently under clinical investigation.

Liang et al. in U.S. Patent Appl. Pub. No. 2006/0100164, the disclosure of which is incorporated herein by reference, describes a new series of triazole-containing ketolide compounds, and an illustrative synthesis thereof. These new compounds show excellent activity against pathogenic organisms, including those that have already exhibited resistance to current therapies. However, it has been discovered herein that side-reactions occur in the processes disclosed by Liang et al leading to impurities that are difficult to remove, and low yields. In addition, starting material impurities are also difficult to remove. Those side-reactions decrease the overall yield of the desired compounds, and those side-products and impurities may complicate the purification of the desired compounds. The occurrence of such side reactions and the presence of such impurities are exacerbated on large commercial scales. In addition, the processes disclosed by Liang et al. include an azide intermediate, which at larger commercial manufacturing scales, may be undesirable, or represent a safety issue. Due to the importance of these triazole-containing ketolide compounds for use in providing beneficial therapies for the treatment of pathogenic organisms, alternative and/or improved processes for their preparation are needed.

The azide intermediate may be avoided by a process that incorporates the side chain intact. However, it has also been reported that introduction of an intact side chain is not a viable process (see, Lee et al., "Process Development of a Novel Azetidinyl Ketolide Antibiotic" Org. Process Res Dev 16:788-797 (2012)). In particular, it has been reported that introduction of an intact side chain leads to an isomeric mixture of products. In addition, it has been reported that introduction of the intact side chain provides only a low yield (<20%).

It has been unexpectedly discovered herein that triazole-containing side chains do not result in an isomeric mixture of products. It has also been unexpectedly discovered herein that triazole-containing side chains provide high yielding reactions. It has also been unexpectedly discovered herein that if the side chain is introduced before the removal of the cladinose, then a single isomer is obtained. It has also been unexpectedly discovered herein that if the side chain is introduced before the removal of the cladinose, then the process provides a high yield.

Described herein are new processes that may be advantageous in preparing compounds of formula (I) that avoid such side-products, and/or may be purified to higher levels of purity. In addition, the processes described herein avoid the azide intermediate by proceeding through a convergent synthetic route.

In one illustrative embodiment of the invention, processes and intermediates are described for preparing compounds of formula (I):

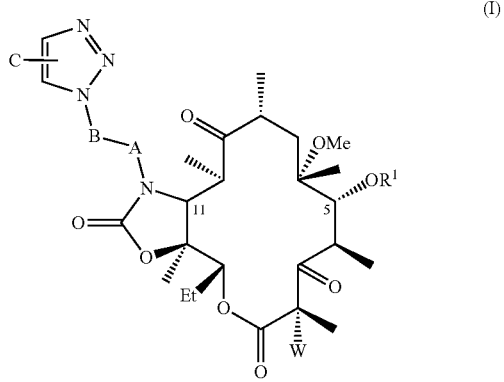

and pharmaceutically acceptable salts, solvates, and hydrates thereof; wherein $R^1$ is a desosamine or a desosamine derivative;

A is —CH$_2$—, —C(O)—, —C(O)O—, —C(O)NH—, —S(O)$_2$—, —S(O)$_2$NH—, —C(O)NHS(O)$_2$—;

B is —(CH$_2$)$_n$— where n is an integer ranging from 0-10; or B is saturated C$_2$-C$_{10}$; or B is unsaturated C$_2$-C$_{10}$, which may contain one or more alkenyl or alkynyl groups; or -A-B- taken together is alkylene, cycloalkylene, or arylene;

C represents 1 or 2 substituents independently selected in each instance from hydrogen, halogen, hydroxy, acyl, acyloxy, sulfonyl, ureyl, and carbamoyl, and alkyl, alkoxy, heteroalkyl, aryl, heteroaryl, arylalkyl, and heteroarylalkyl, each of which is optionally substituted; and W is hydrogen, F, Cl, Br, I, or OH.

In another illustrative embodiment, processes and intermediates are described herein for preparing 11-N-[[4-(3-aminophenyl)-1,2,3-triazol-1-yl]-butyl]-5-desosaminyl-2-fluoro-3-oxoerythronolide A, 11,12-cyclic carbamate, also known as OP-1068, CEM-101, and solithromycin.

In another embodiment of the compounds of formula (I), $R^1$ is a desosamine that includes an optionally protected 2'-hydroxy group. In another embodiment, $R^1$ is a desosamine that includes a protected 2'-hydroxy group. In another embodiment, the protecting group is an acyl group. In another embodiment, the protecting group is a sterically hindered acyl group, such as a branched alkyl, aryl, heteroaryl, arylalkyl, arylalkyl, or heteroarylalkyl acyl group, each of which is optionally substituted. In another embodiment, the protecting group is an optionally substituted benzoyl group. In another embodiment, the protecting group is a benzoyl group. In another embodiment, -A-B- is alkylene, cycloalkylene, or arylene. In another embodiment, -A-B- is alkylene. In another embodiment, -A-B- is C$_3$-C$_5$ alkylene. In another embodiment, -A-B- is C$_4$ alkylene. In another embodiment, -A-B- is —(CH$_2$)$_4$—. In another embodiment, C is optionally substituted aryl, heteroaryl, arylalkyl, or heteroarylalkyl. In another embodiment, C is optionally substituted aryl or heteroarylalkyl. In another embodiment, C is optionally substituted aryl. In another embodiment, C is substituted aryl. In another embodiment, C is amino substituted aryl. In another embodiment, C is amino substituted phenyl. In another embodiment, C is 3-aminophenyl. In another embodiment, W is H or F. In another embodiment, W is F.

It is to be understood that each and every combination, and each and every selection, and combination thereof, of the forgoing and following embodiments is described herein. For example, in another embodiment, $R^1$ is a desosamine that includes a protected 2'-hydroxy group, where the protecting group is an acyl group; or $R^1$ is a desosamine that includes a protected 2'-hydroxy group, where the protecting group is a sterically hindered acyl group; or $R^1$ is a desosamine that includes a protected 2'-hydroxy group, where the protecting group is a benzoyl group, and -A-B- is C$_3$-C$_5$ alkylene; or $R^1$ is a desosamine that includes a protected 2'-hydroxy group, where the protecting group is a benzoyl group, and -A-B- is —(CH$_2$)$_4$—; or $R^1$ is a desosamine that includes a protected 2'-hydroxy group, where the protecting group is a benzoyl group, and -A-B- is —(CH$_2$)$_4$—, and C is optionally substituted aryl; or $R^1$ is a desosamine that includes a protected 2'-hydroxy group, where the protecting group is a benzoyl group, and -A-B- is —(CH$_2$)$_4$—, and C is 3-aminophenyl; and so forth.

It is to be understood that the processes described herein may be advantageously performed simply and cost-effectively. It is further to be understood that the processes described herein may be scaled to large production batches. It is further to be understood that the processes described herein are performed in fewer steps than conventional processes. It is further to be understood that the processes described herein are performed are more convergent, and/or require shorter linear sub-processes, than conventional processes. It is further to be understood that the processes described herein may concomitantly produce fewer or different side products than known processes. It is further to be understood that the processes described herein may yield compounds described herein in higher purity than known processes.

DETAILED DESCRIPTION

Several illustrative embodiments of the invention are described by the following enumerated clauses:

1A. A process for preparing a compound of formula (I) as described herein, the process comprising the step of (A) contacting a compound of formula

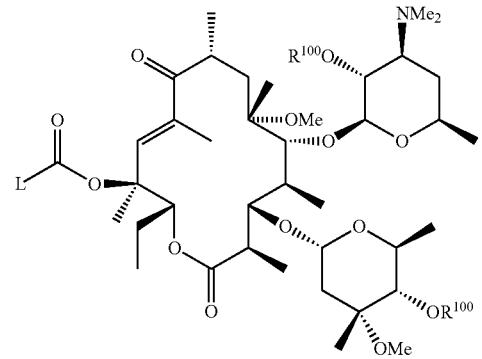

or a salt thereof, where $R^{100}$ is a hydroxyl protecting group, and L is a leaving group, with a compound of formula

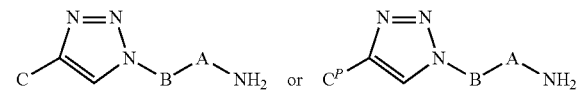

or a salt thereof, where C is as defined herein, and $C^P$ is a protected form of C, and a base, to prepare a compound of formula

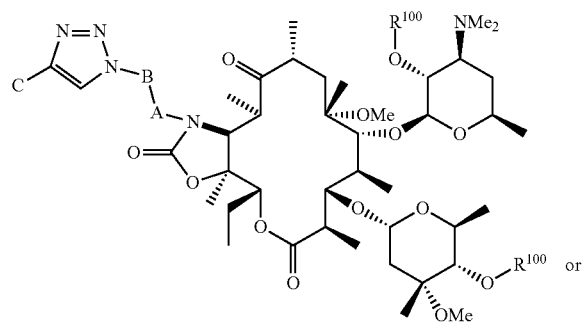 or

-continued
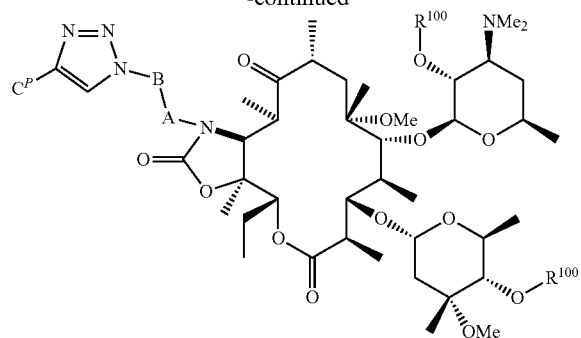
or a salt thereof; or
(B) contacting a compound of formula
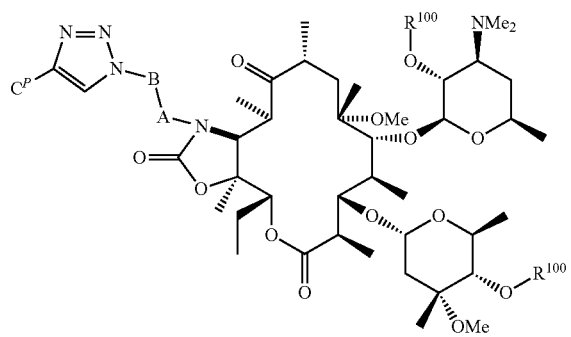
or a salt thereof, with one or more protecting group forming agents to prepare a compound of formula
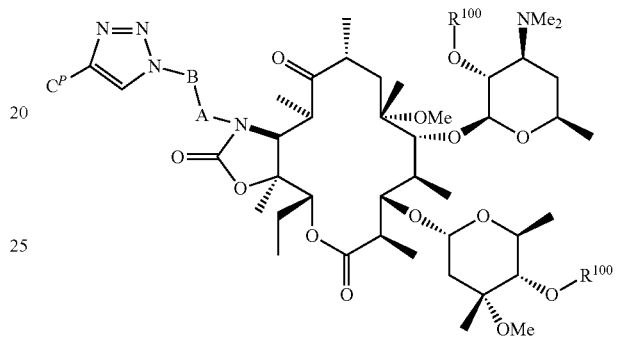
or a salt thereof; or
(C) contacting a compound of formula
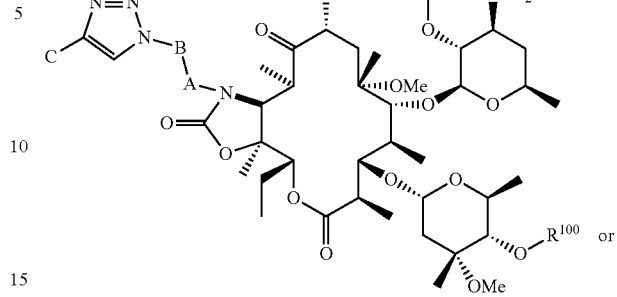
or a salt thereof, with an acid to prepare a compound of formula
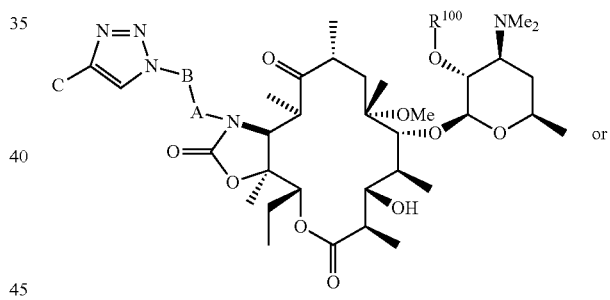
or a salt thereof; or
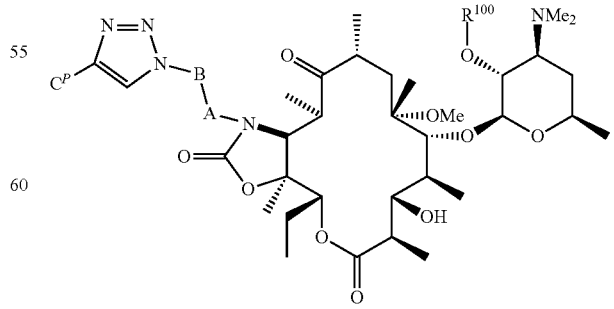
or a salt thereof; or (D) contacting a compound of formula

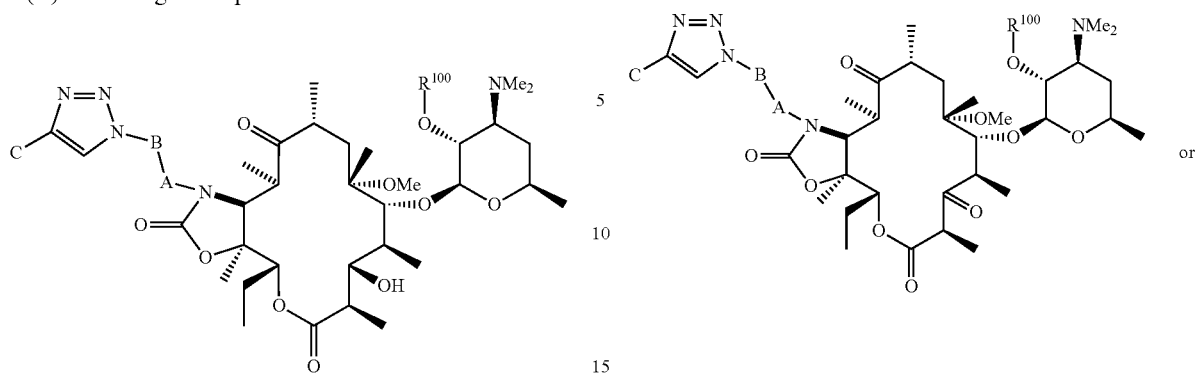

or a salt thereof, with one or more protecting group forming agents to prepare a compound of formula

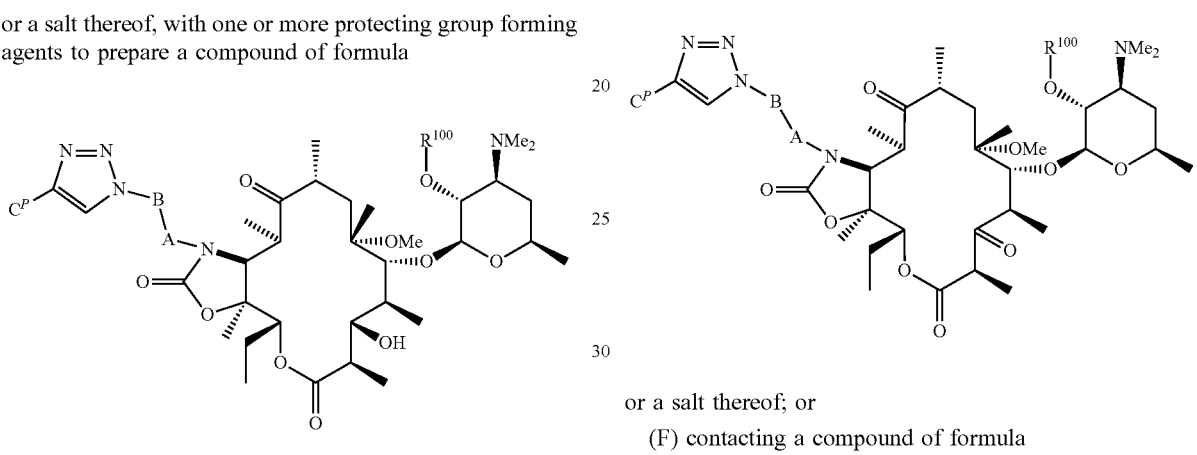

or a salt thereof; or (E) contacting a compound of formula

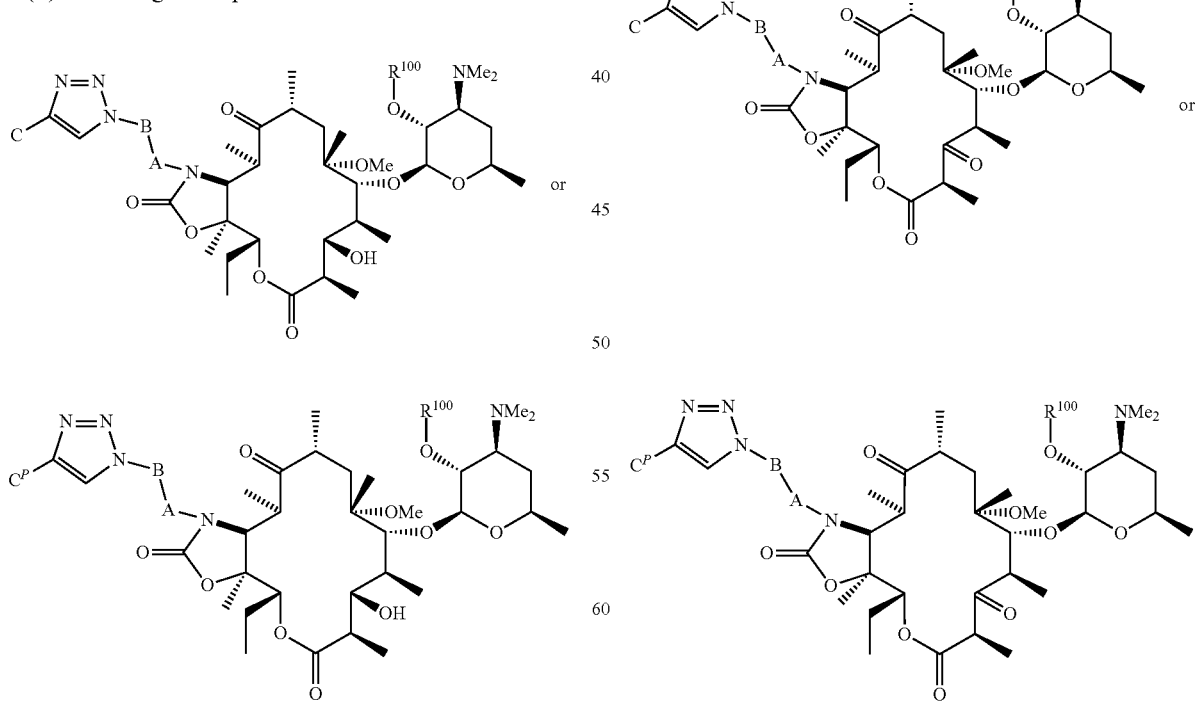

or a salt thereof, with an oxidizing agent to prepare a compound of formula or a salt thereof; or (F) contacting a compound of formula or a salt thereof, with a hydroxylating or halogenating agent to prepare a compound of formula

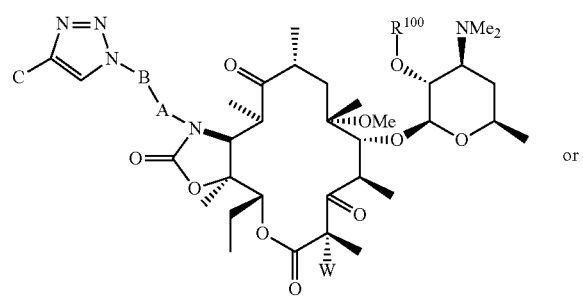

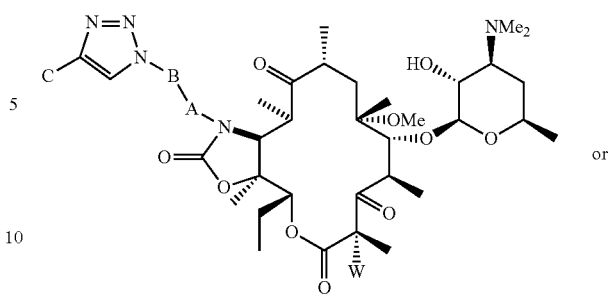

or

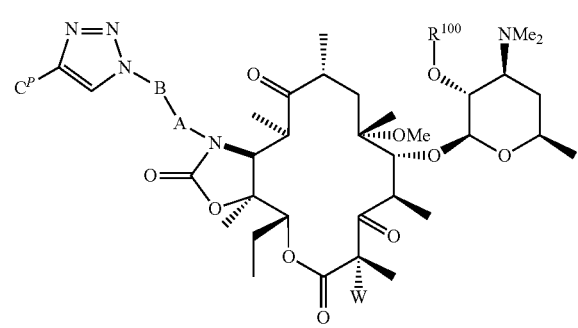

or a salt thereof; or
(G1) contacting a compound of formula

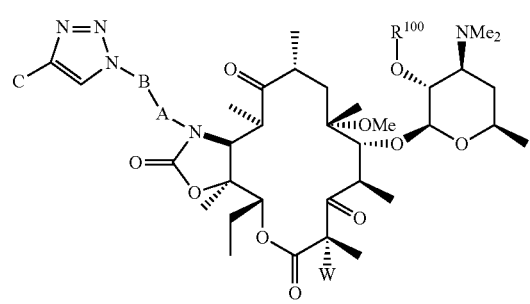

or a salt thereof, with a hydroxy deprotecting agent to prepare a compound of formula

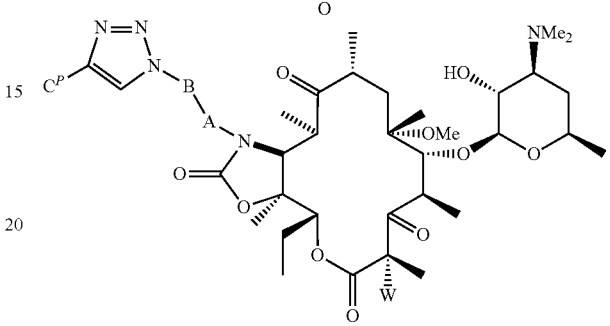

or

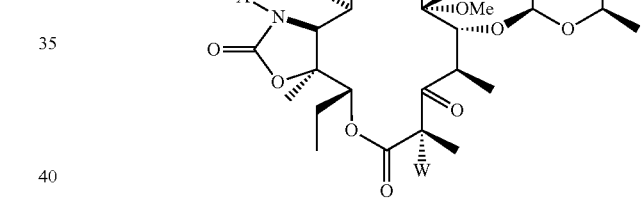

or a salt thereof; or
(G2) contacting a compound of formula

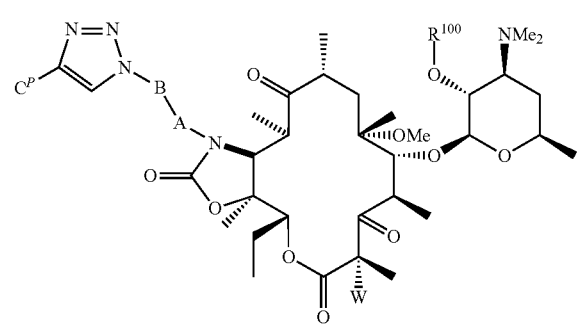

or

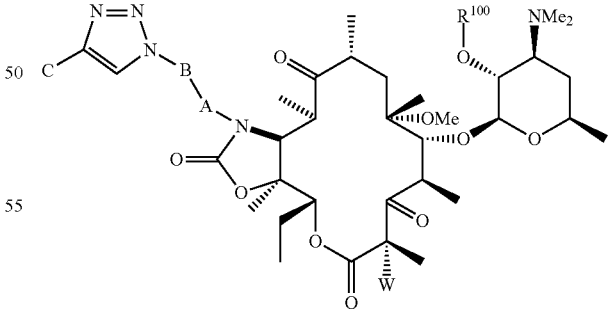

or a salt thereof, with one or more deprotecting agents to prepare the corresponding deprotected compound of formula or a salt thereof; or
any combination of the foregoing.

1B. The process of clause 1A wherein steps (G1) and (G2) are performed sequentially, contemporaneously, or simultaneously.

1C. The process of clause 1A wherein steps (G1) and (G2) are performed simultaneously.

1D. The process of clauses 1 wherein the deprotecting agent and the hydroxy deprotecting agent are the same.

1E. The process of clauses 1 wherein $C^P$ is $N^P$-substituted phenyl.

2A. A process for preparing a compound of formula (I) as described herein, the process comprising the step of (a) contacting a compound of formula

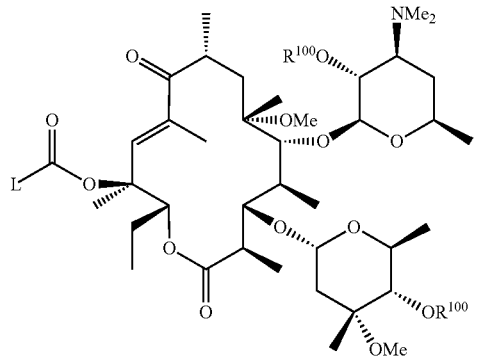

or a salt thereof, where $R^{100}$ is a hydroxyl protecting group, and L is a leaving group, with a compound of formula

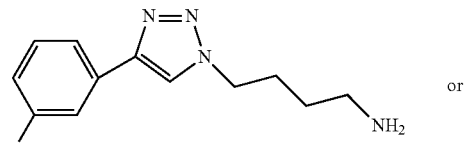

or

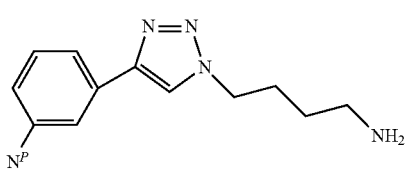

or a salt thereof, where $N^P$ is a protected amine, and a base; to prepare a compound of formula

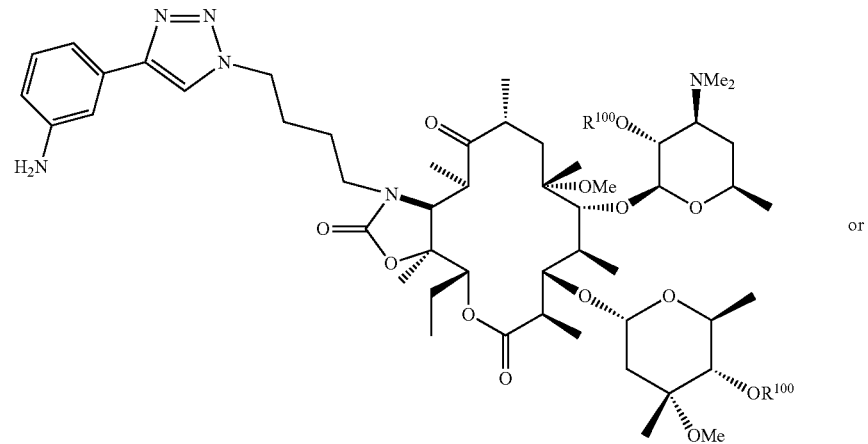

or

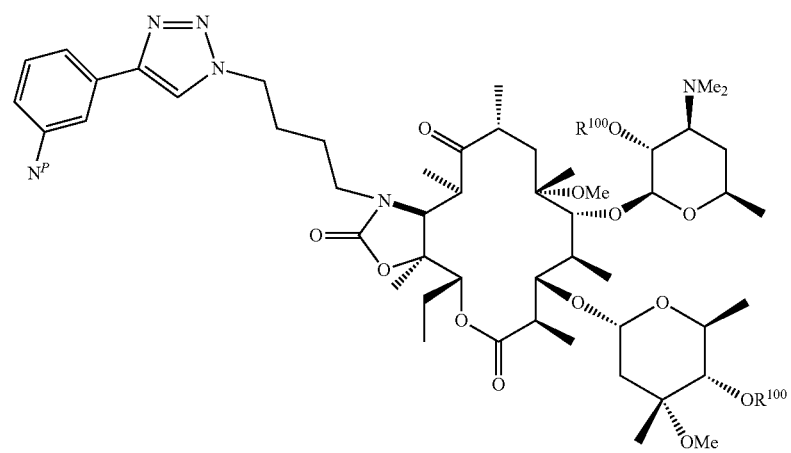

or a salt thereof; or
  (b) contacting a compound of formula
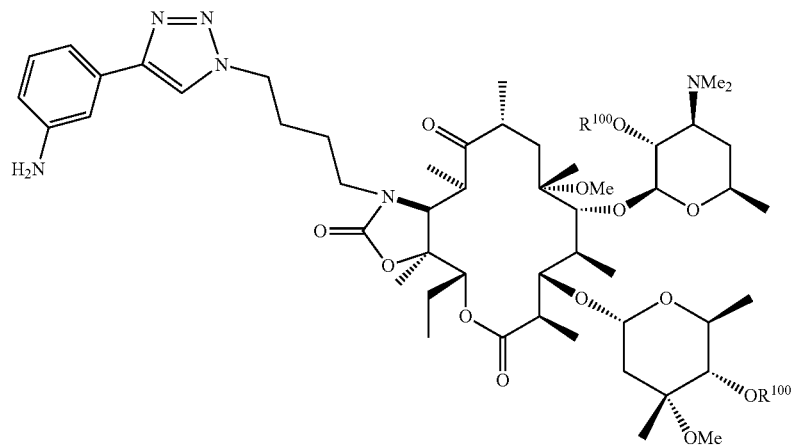
or a salt thereof, with an amine protecting group forming agent to prepare a compound of formula
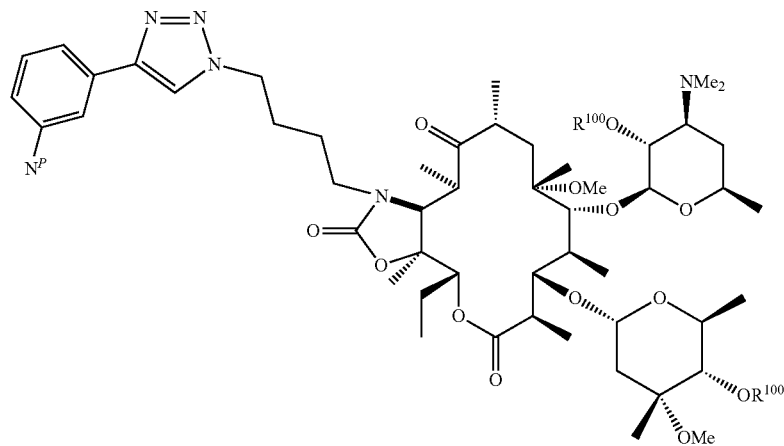
45
or a salt thereof; or
  (c) contacting a compound of formula
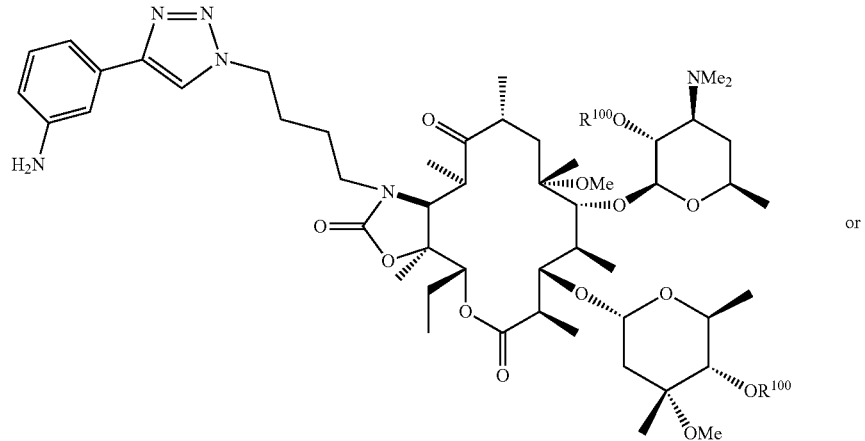
or

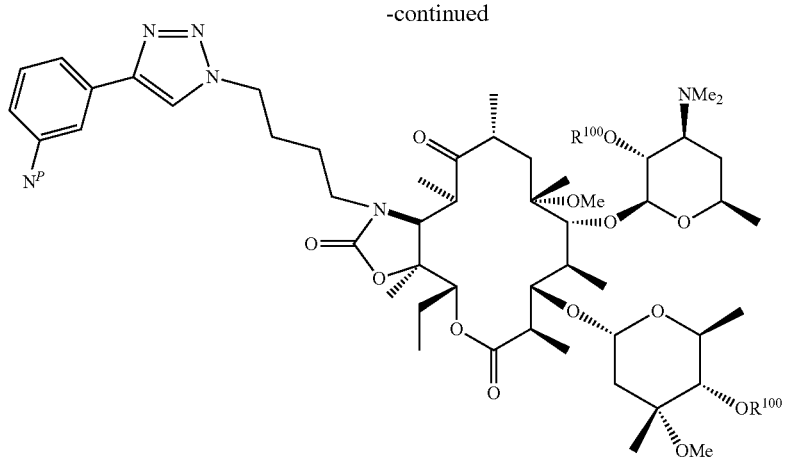
or a salt thereof, with an acid to prepare a compound of formula
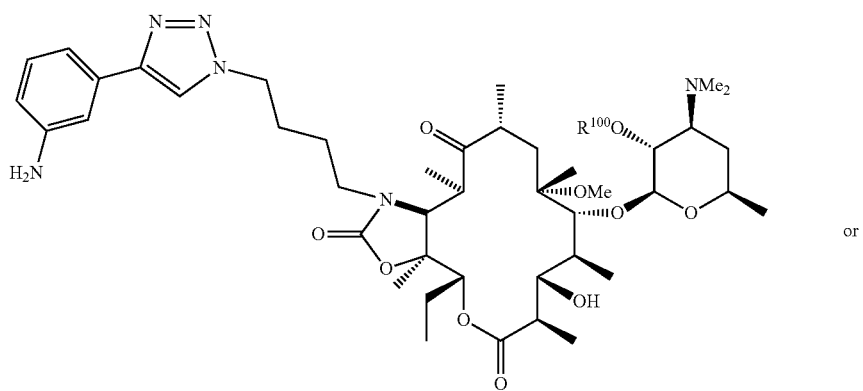
or
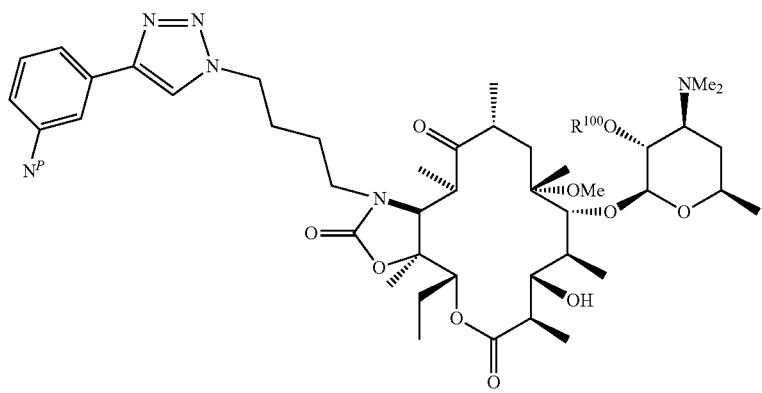

or a salt thereof; or
(d) contacting a compound of formula

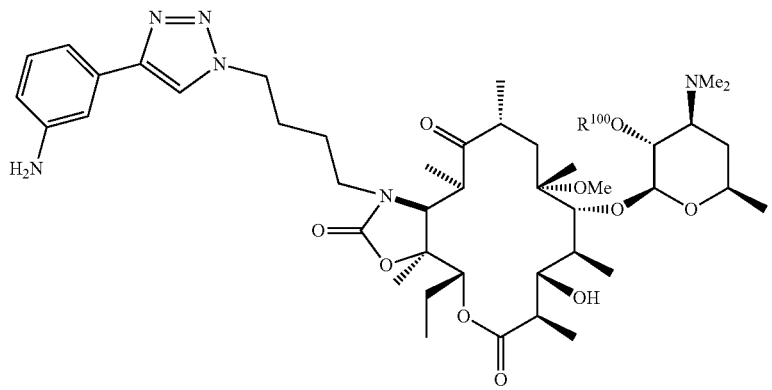

or a salt thereof, with an amine protecting group forming agent to prepare a compound of formula

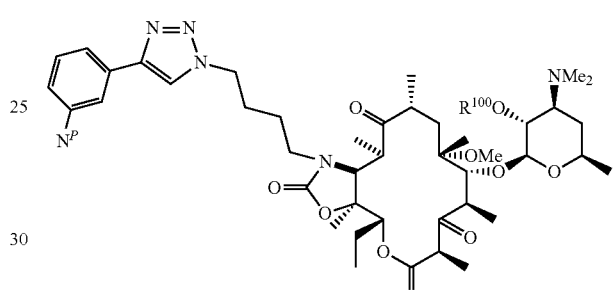

or a salt thereof; or
(e) contacting a compound of formula

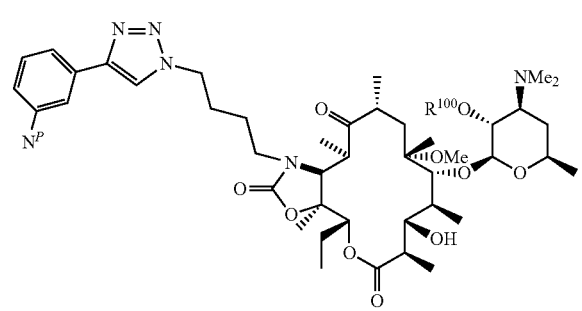

or a salt thereof; or
(f) contacting a compound of formula

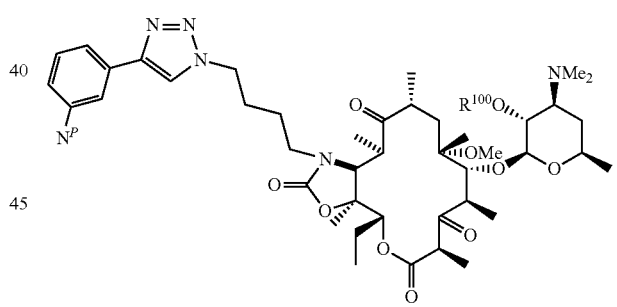

or a salt thereof, with an amine deprotecting agent to prepare a compound of formula

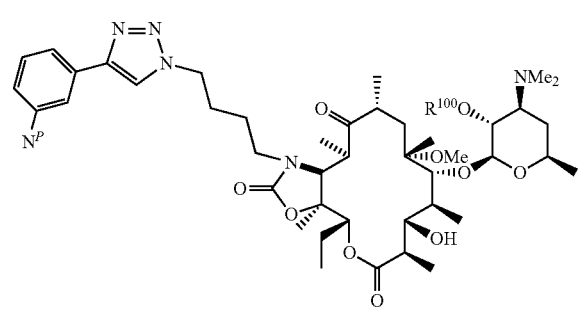

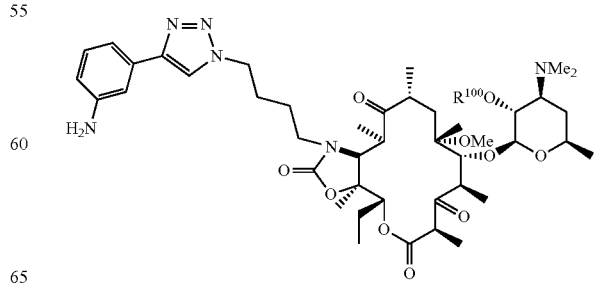

or a salt thereof, with an oxidizing agent to prepare a compound of formula or a salt thereof; or
(g) contacting a compound of formula
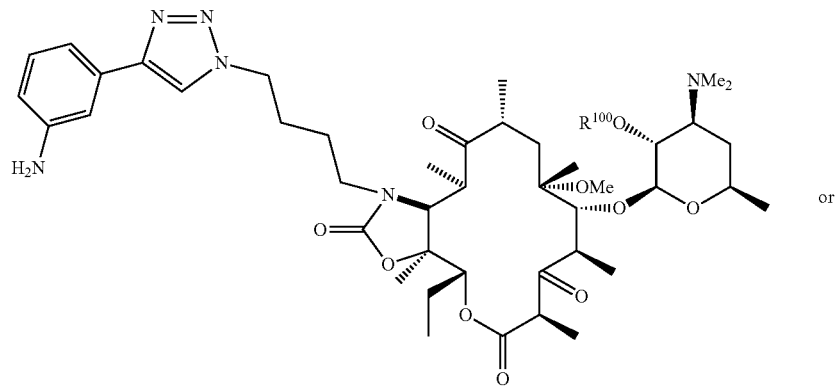
or
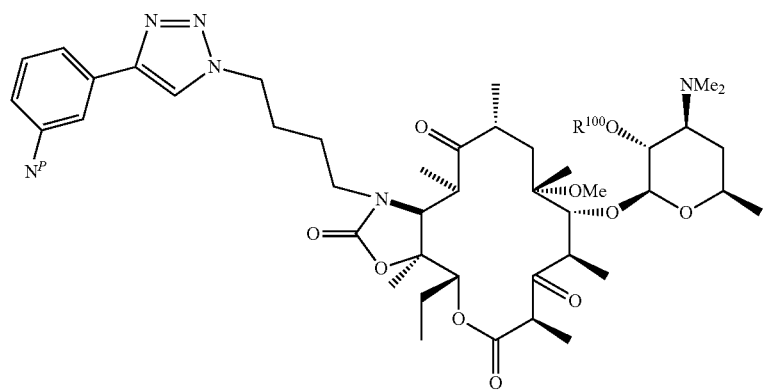
or a salt thereof, with a fluorinating agent to prepare a compound of formula
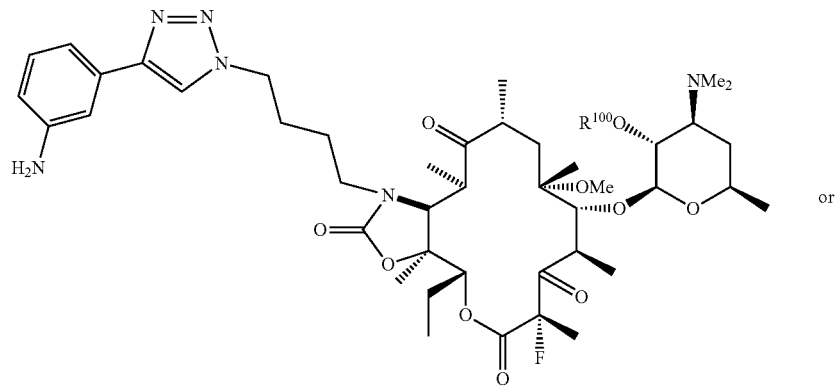
or -continued
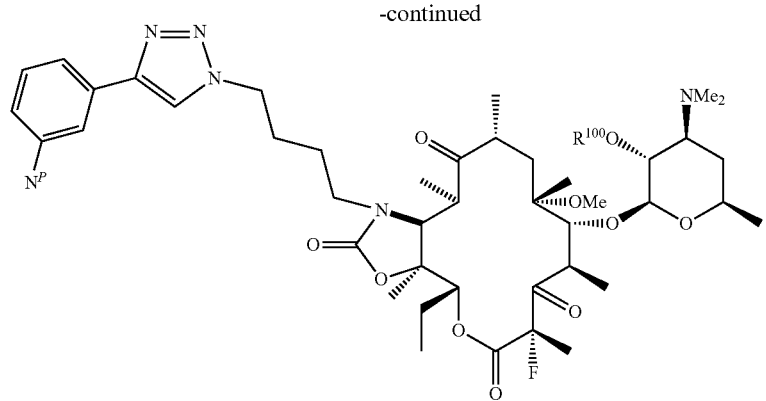
or a salt thereof; or
(h1) contacting a compound of formula
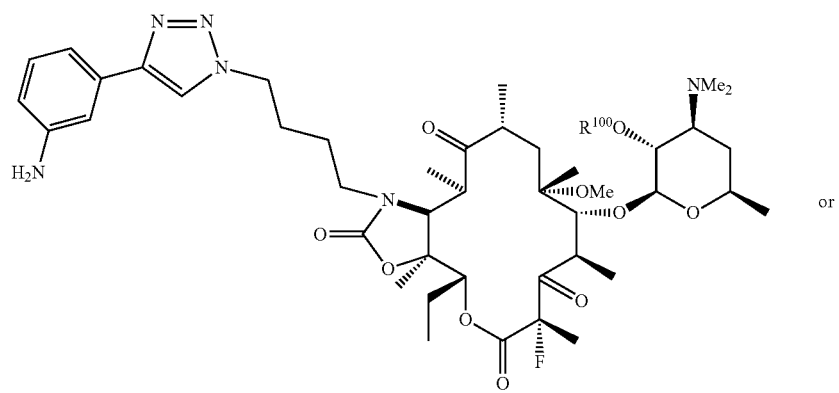
or
or a salt thereof, with a hydroxy deprotecting agent to prepare a compound of formula
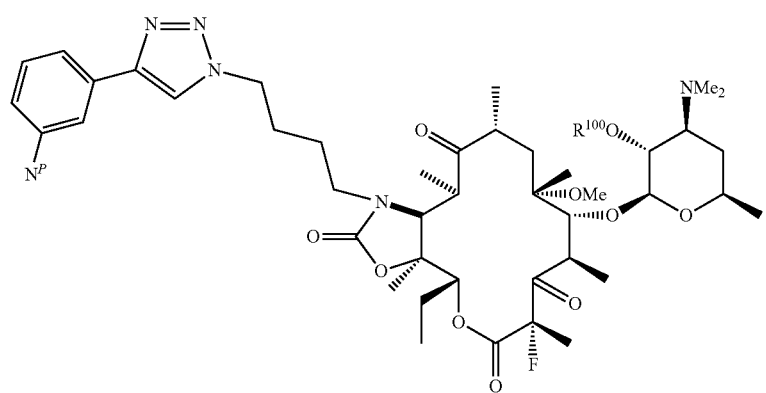
65

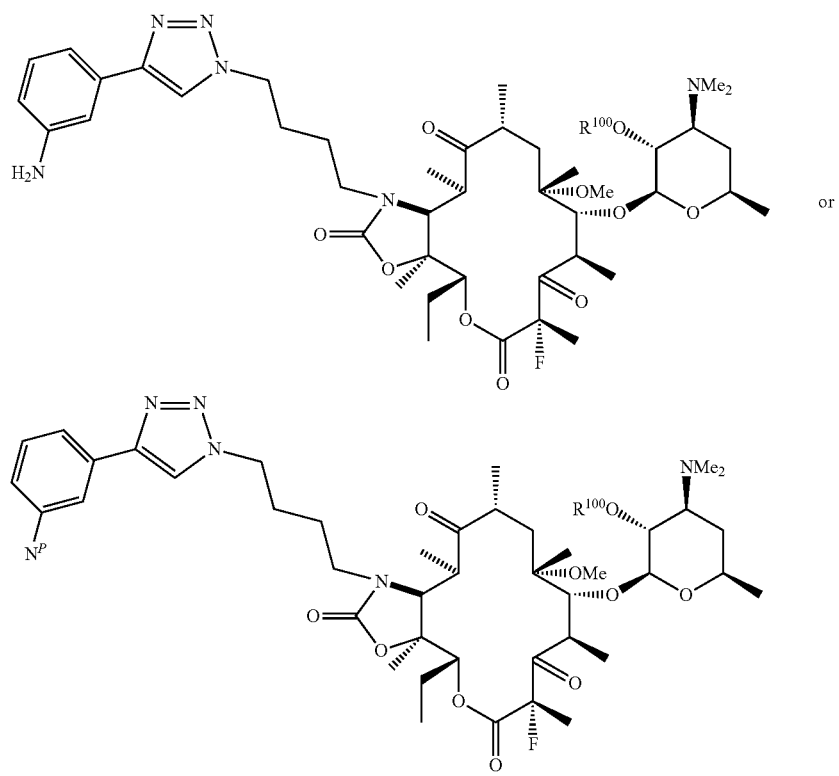
or a salt thereof; or
  (h2) contacting a compound of formula
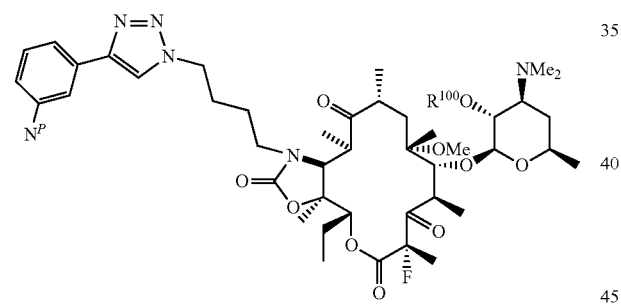
or a salt thereof, with an amine deprotecting agent to prepare a compound of formula
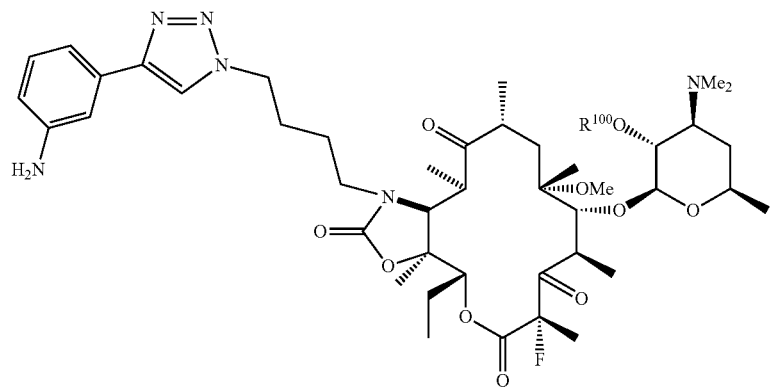
or a salt thereof; or
  any combination of the foregoing.

2B. The process of clause 2A wherein steps (h1) and (h2) are performed sequentially, contemporaneously, or simultaneously.

2C. The process of clause 2A wherein steps (h1) and (h2) are performed simultaneously.

3. The process of clauses 2 wherein the amine protecting group forming agent is an acylating agent or amide, carbamate, or urea forming agent.

4. The process of any one of clauses 2 to 3 wherein the amine deprotecting agent and the hydroxyl deprotecting agent are the same, such as ammonia or ammonium hydroxide and a solvent.

5. The process of any one of clauses 1 to 4 wherein $N^P$ is $NHC(O)CF_3$.

6A. A process for preparing a compound of formula (I) as described herein, the process comprising the step of (a') contacting a compound of formula

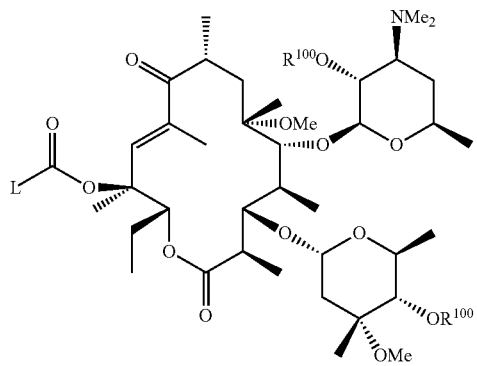

or a salt thereof, where $R^{100}$ is a hydroxyl protecting group, and L is a leaving group, with a compound of formula

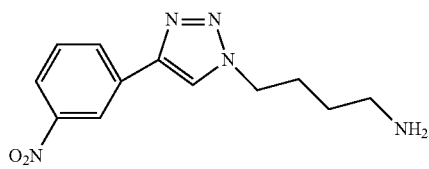 [SMILES: NCCCCn1cc(-c2cccc([N+](=O)[O-])c2)nn1]

or a salt thereof, and a base; to prepare a compound of formula

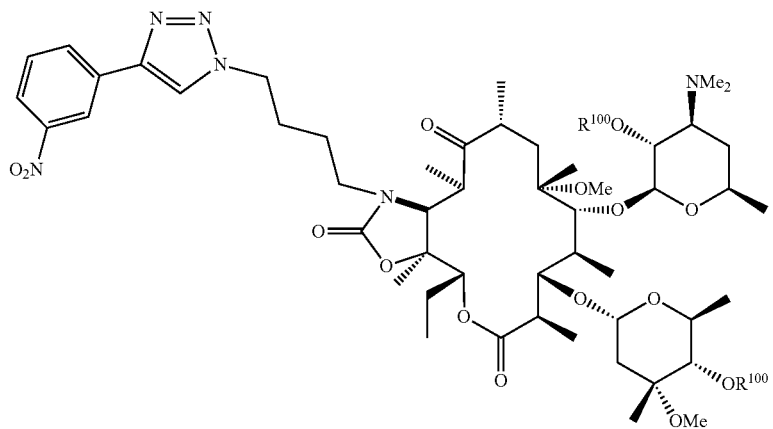

or a salt thereof; or
(b') contacting a compound of formula

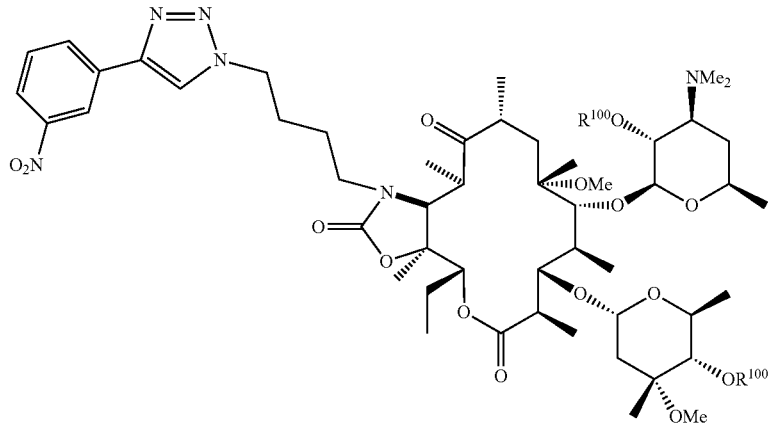

or a salt thereof, with an acid to prepare a compound of formula

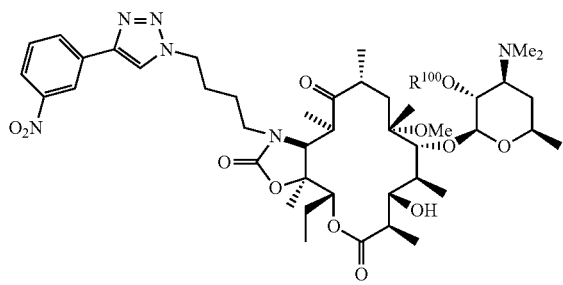

or a salt thereof; or
(c') contacting a compound of formula

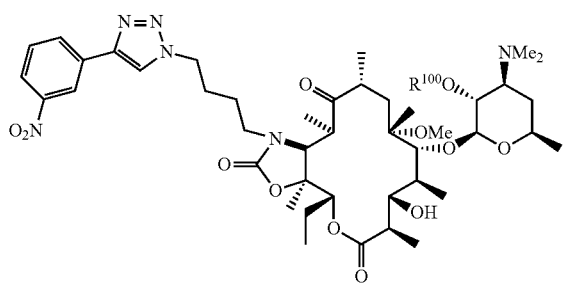

or a salt thereof, with an oxidizing agent to prepare a compound of formula

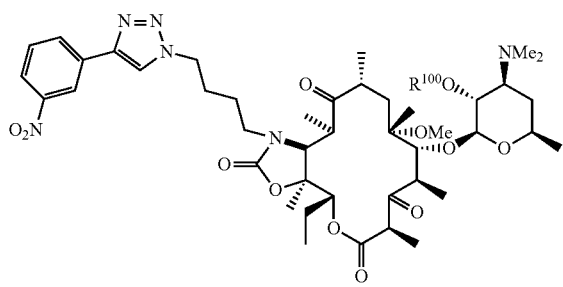

or a salt thereof; or (d') contacting a compound of formula

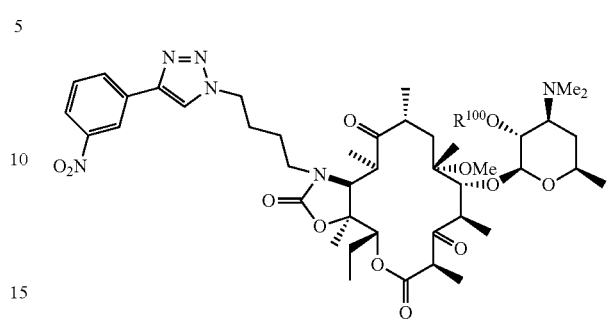

or a salt thereof, with a fluorinating agent to prepare a compound of formula

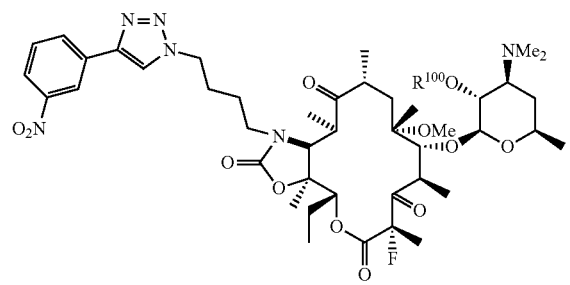

or a salt thereof; or
(e') contacting a compound of formula

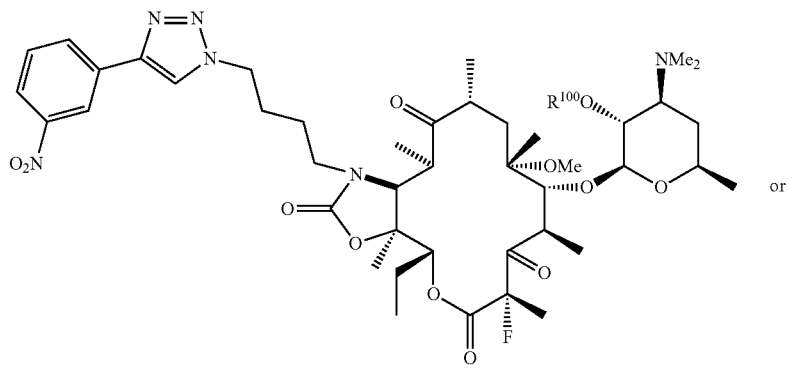

or

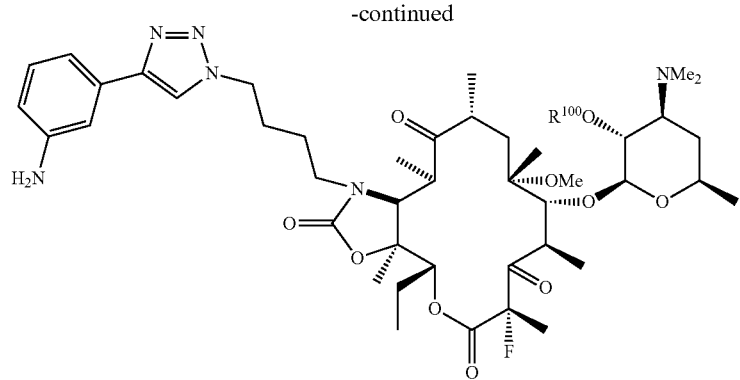
or a salt thereof, with a hydroxy deprotecting agent to prepare a compound of formula
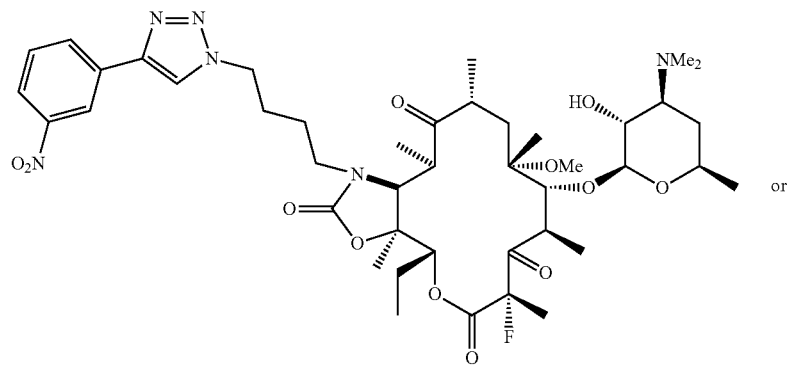
or
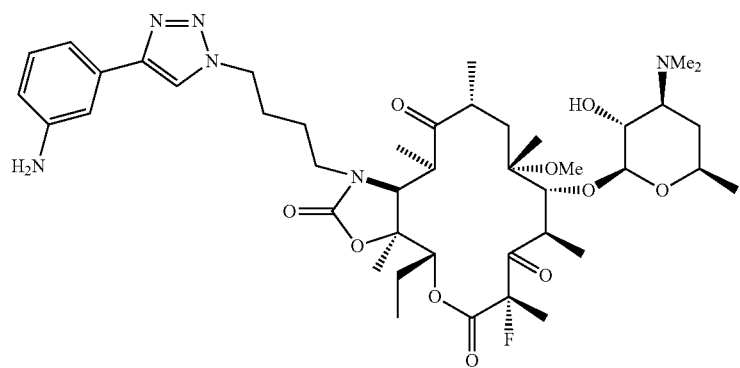

or a salt thereof; or
(f') contacting a compound of formula
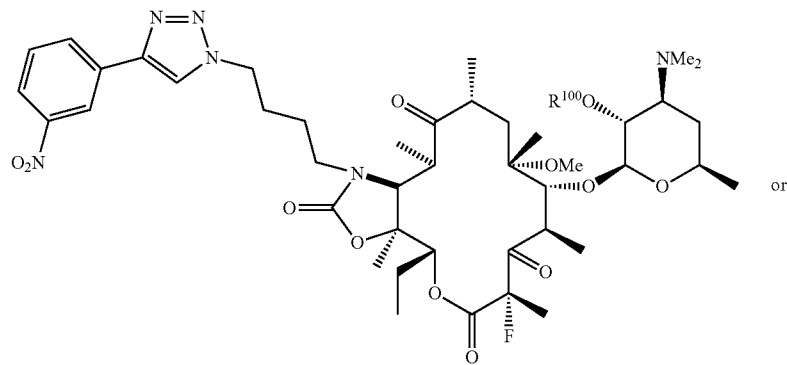
or
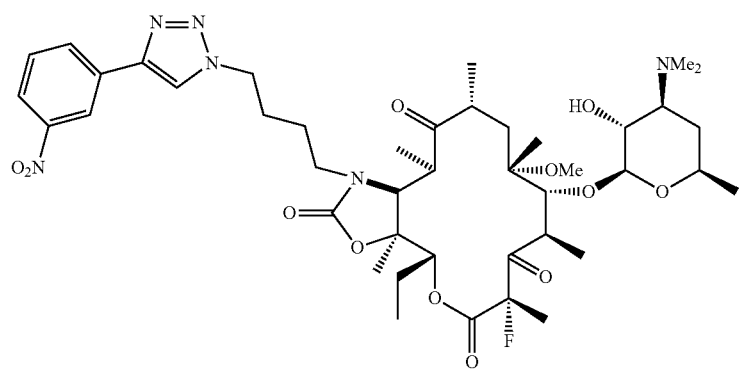
or a salt thereof, with a reducing agent to prepare a compound of formula
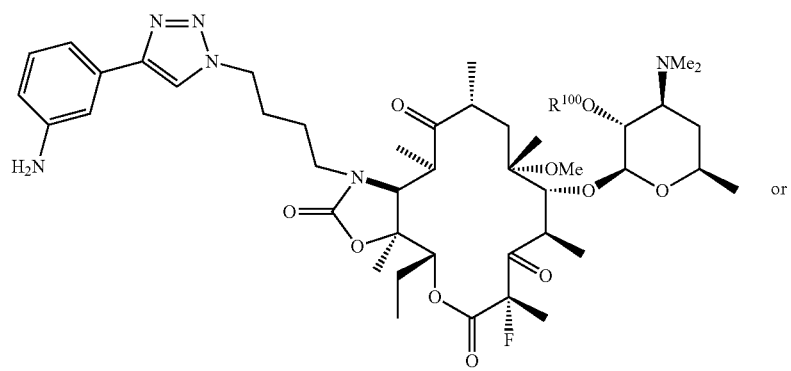
or -continued

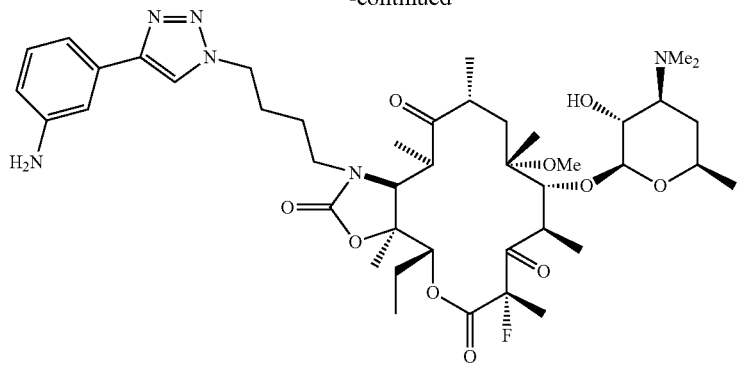

or a salt thereof; or
any combination of the foregoing.

6B. The process of clause 6A wherein steps (e') and (f') are performed sequentially, contemporaneously, or simultaneously.

6C. The process of clause 6A wherein steps (e') and (f') are performed simultaneously.

7. The process of clauses 6 wherein the hydroxy deprotecting agent and the reducing agent are the same.

8. The process of any one of clauses 1 to 7 wherein the leaving group is halo, pentafluorophenoxy, a sulfonate, such as triflate, a hydroxyamino, such as an HOBt, or imidazol-1-yl.

9. The process of any one of clauses 1 to 8 wherein the leaving group is imidazol-1-yl.

10. The process of any one of clauses 1 to 9 wherein the base is DBU.

11A. The process of any one of clauses 1 to 10 wherein the acid is aqueous HCl, such as 5% HCl, optionally with an organic cosolvent, such as a ketone, such as acetone.

11B. The process of any one of clauses 1 to 10 wherein the acid is HCl in an organic cosolvent, such as a ketone, such as acetone, or an alcohol, such as methanol, or a combination thereof.

12. The process of any one of clauses 1 to 11 wherein $N^P$ is an amide or carbamate, such as Bz-NH, $CF_3C(O)$—NH, Cbz-NH, Boc-NY, Fmoc-NY, BsMoc-NH, Trityl-NH, MeOTrityl-NH, and the like 13. The process of any one of clauses 1 to 12 wherein the amine protecting group forming agent is TFAA.

14. The process of any one of clauses 1 to 12 wherein the amine protecting group forming agent is benzoyl chloride.

15. The process of any one of clauses 1 to 12 wherein the amine protecting group forming agent is Boc-anhydride.

16. The process of any one of clauses 1 to 12 wherein the amine protecting group forming agent is Fmoc chloride.

17. The process of any one of clauses 1 to 12 wherein the protected amine is formed in the presence of base, such a TEA.

18. The process of any one of clauses 1 to 17 wherein the oxidizing agent is trifluoroacetic anhydride in pyridine, PCC, Jones oxidation, TEMPO/NaOCl, Swern oxidation, Dess-Martin reagent, or Corey-Kim reagent.

19. The process of any one of clauses 1 to 17 wherein the oxidizing agent is N-chlorosuccinimide (NCS)/DMS.

20. The process of any one of clauses 1 to 19 wherein the fluorinating agent is NFSI, F-TEDA, or Selectfluor.

21. The process of any one of clauses 1 to 20 wherein the amine deprotecting agent is an amide hydrolyzing, cleaving, or removing agent.

22. The process of any one of clauses 1 to 20 wherein the amine deprotecting agent is hydrogen, such as hydrogen gas or hydrogen produced in situ, such as by transfer hydrogenation, such as by a transfer hydrogenation agent like formic acid, ammonium formate, and the like, and a metal catalyst.

23. The process of any one of clauses 1 to 20 wherein the amine deprotecting agent is ammonia, aqueous ammonia, or ammonia or aqueous ammonia with an organic cosolvent, such as an alcohol, such as methanol.

24. The process of any one of clauses 1 to 20 wherein the amine deprotecting agent is a carbamate hydrolyzing, cleaving, or removing agent.

25. The process of any one of clauses 1 to 24 wherein the deprotecting agent is an acid, such as TFA.

26. The process of any one of clauses 1 to 25 wherein the hydroxy deprotecting agent is an ester hydrolyzing, cleaving, or removing agent.

27. The process of any one of clauses 1 to 25 wherein the hydroxy deprotecting agent is an alcohol, such as methanol.

28. The process of any one of clauses 1 to 27 wherein the reducing agent is hydrogen, such as hydrogen gas or hydrogen produced in situ, such as by transfer hydrogenation, such as by a transfer hydrogenation agent like formic acid, ammonium formate, and the like, and a metal catalyst.

29. The process of clause 28 wherein the metal catalyst is 5% Pd—C, 5% Pt—C, 10% Pd—C, 10% Pd—C, Pearlman's Catalyst, 20% Pd(OH)2, Raney-Ni, nickel sponge, iron, and the like.

30. The process of any one of clauses 1 to 29 wherein C is aryl, heteroaryl, arylalkyl, or heteroarylalkyl, each of which is optionally substituted.

31. The process of any one of clauses 1 to 30 wherein A is $CH_2$.

32. The process of any one of clauses 1 to 31 wherein B is $(CH_2)_n$.

33. The process of any one of clauses 1 to 31 wherein B is $(CH_2)_n$, and n is an integer between 2 and 6.

34. The process of any one of clauses 1 to 31 wherein B is $(CH_2)_n$, and n is an integer between 2 and 5.

35. The process of any one of clauses 1 to 31 wherein B is $(CH_2)_n$, and n is an integer between 3 and 6.

36. The process of any one of clauses 1 to 31 wherein B is $(CH_2)_n$, and n is an integer between 3 and 5.

37. The process of any one of clauses 1 to 31 wherein B is $(CH_2)_n$, and n is an integer between 3 and 4.

38. The process of any one of clauses 1 to 31 wherein B is $(CH_2)_n$, and n is 3.

39. The process of any one of clauses 1 to 38 wherein $R^{100}$ is acyl.

40. The process of any one of clauses 1 to 38 wherein $R^{100}$ is alkylcarbonyl or optionally substituted benzoyl.

41. The process of any one of clauses 1 to 38 wherein $R^{100}$ is acetyl or benzoyl, or $R^{100}$ is benzoyl.

42. The process of any one of clauses 1 to 41 wherein W is H or F.

43. The process of any one of clauses 1 to 41 wherein W is F.

In another illustrative embodiment, $R^{100}$ is a hydroxy protecting group, such as an acyl group. Additional hydroxyl protecting groups are described in Greene & Wuts, "Protective Groups in Organic Synthesis," 2nd Ed. John Wiley & Sons, Inc., the disclosure of which is incorporated herein by reference. In another embodiment, $R^{100}$ is such an additional hydroxyl protecting. In another illustrative embodiment, $R^{100}$ is a sterically hindered acyl group; formed with a sterically hindered acylating agent $R^{100}$-L, wherein $R^{100}$ is a sterically hindered acyl group and L is a leaving or activating group, to form the corresponding 2'-acyl derivative.

Illustrative sterically hindered acyl or diacyl derivatives include but are not limited to cyclohexylcarbonyl, benzoyl, neopentoyl, pivaloyl, and the like. A wide variety of activating groups for forming the acyl derivative may be used to prepare the required acylating agent, including but not limited to anhydrides, chlorides, triflates, bromides, and the like. In one aspect, the sterically hindered acylating agent is benzoic anhydride, or an equivalent activated benzoyl reagent capable of forming a benzoyl ester at the 2' or both the 2' and 4' positions. In another embodiment $R^{100}$ is an optionally substituted benzoyl group, and the process includes an optionally substituted benzoic anhydride, or an equivalent activated optionally substituted benzoylating reagent capable of forming the optionally substituted benzoyl ester.

Acylation is generally performed in the presence of a solvent and a base. Illustrative solvents include, but are not limited to, ethyl acetate, dichloromethane, acetone, pyridine and the like, and mixtures thereof. Illustrative bases include but are not limited to inorganic bases, such as sodium and potassium bicarbonates and carbonates, sodium and potassium hydroxides, and the like, and mixtures thereof; and amine bases, such as pyridine, dimethylaminopyridine (DMAP), triethylamine (TEA), diisopropylethylamine (DIPEA, Hünigs base), 1,4-diazabicyclo[2.2.2]octane (DABCO), and the like, and mixtures thereof. The reaction may be performed at a variety of temperatures, such as in the range from about 0° C. to about 60° C., and illustratively at about 10° C. to about 30° C.

In another illustrative embodiment, processes are described for preparing compounds of formulae

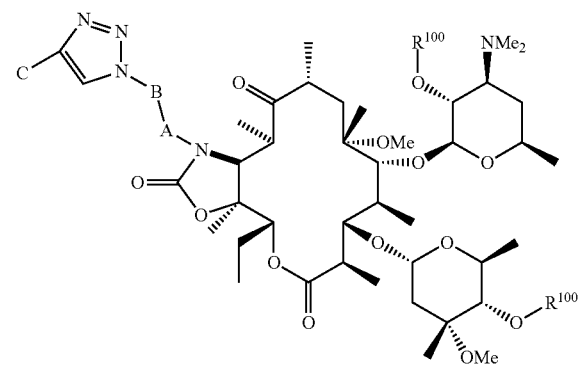

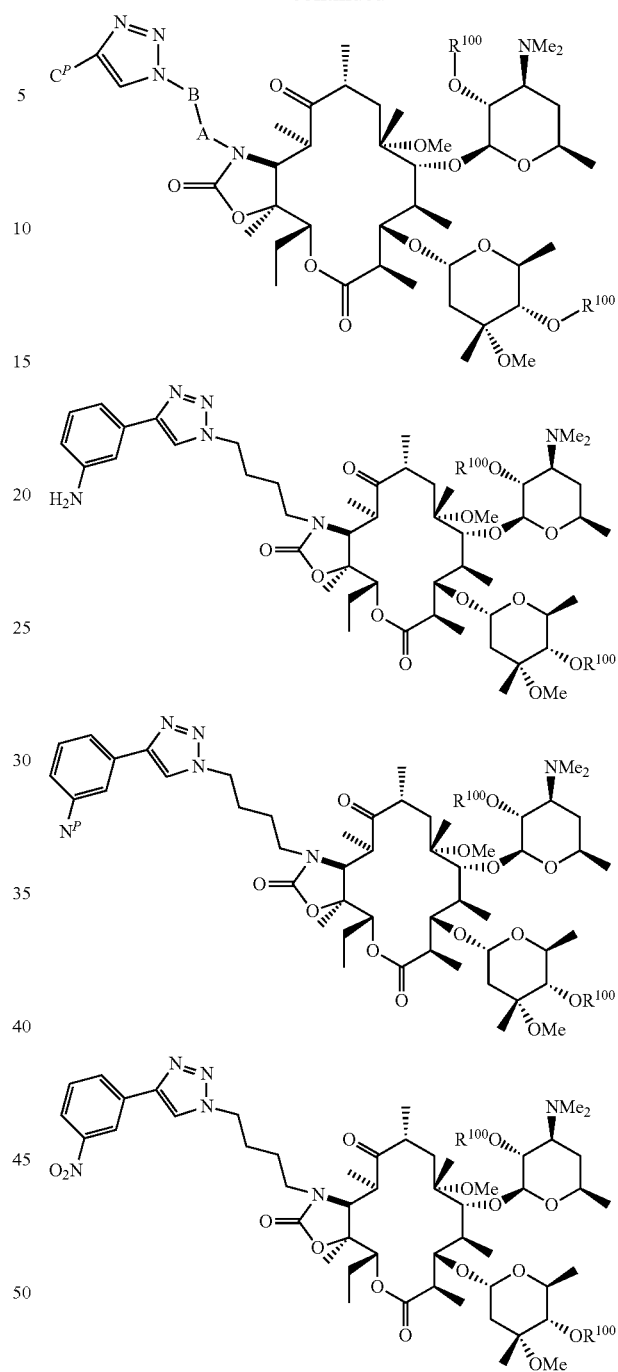

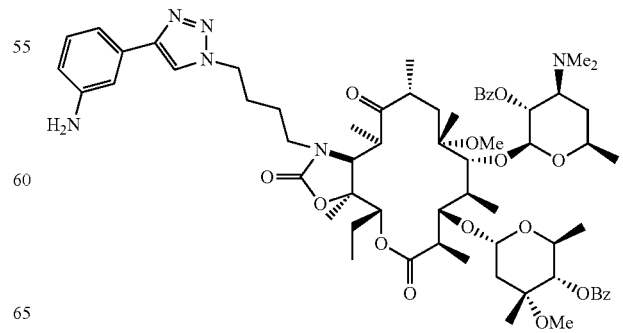

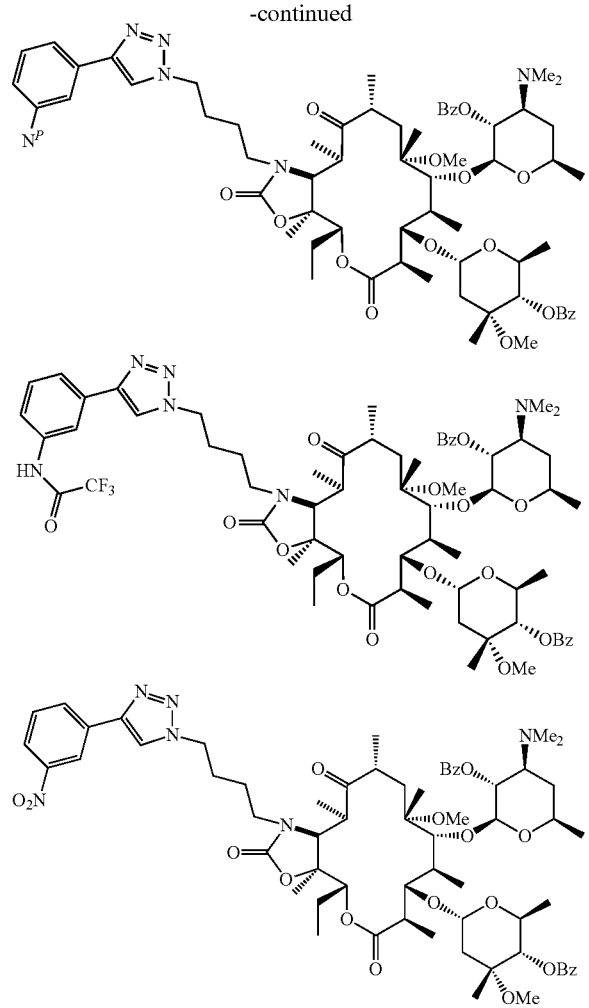

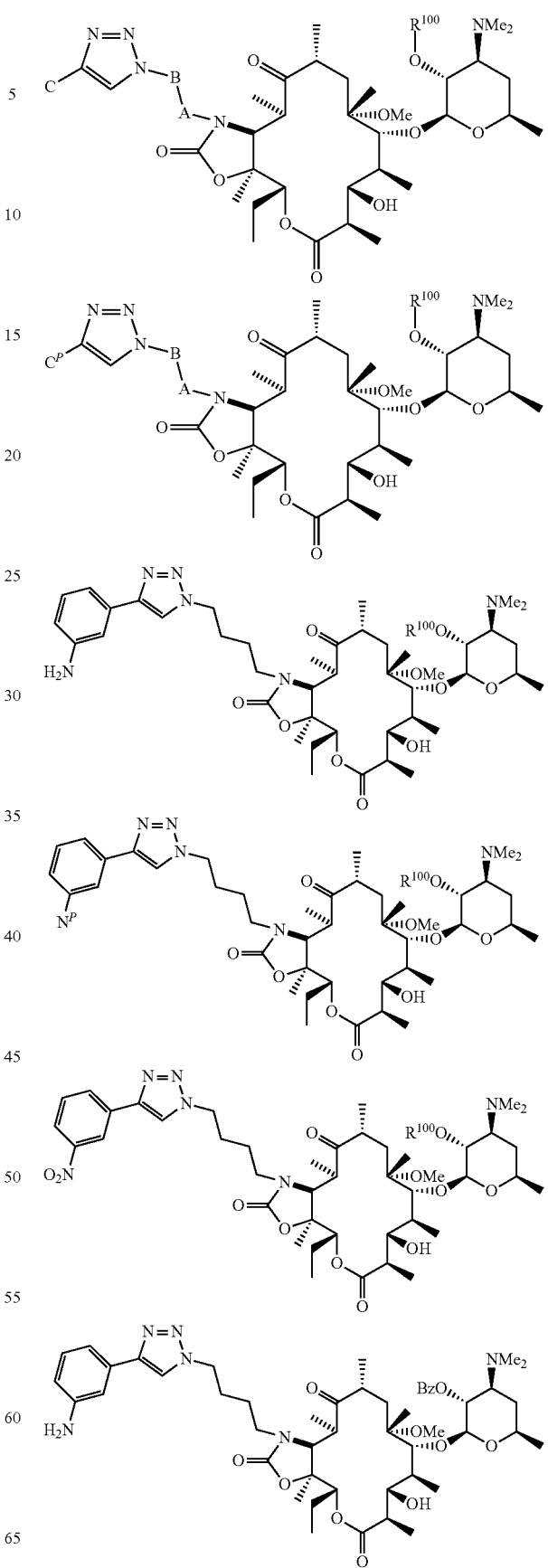

and salts thereof. The processes are generally performed in the presence of a polar solvent, including polar protic and polar aprotic solvents, or a mixture thereof. Illustrative polar protic solvents include, but are not limited to water, alcohols, such as methanol, ethanol, isopropanol, n-propanol, n-butanol, iso-butyl alcohol, tert-butyl alcohol, methoxyethanol, ethoxyethanol, pentanol, neo-pentyl alcohol, tert-pentyl alcohol, cyclohexanol, ethylene glycol, propylene glycol, benzyl alcohol, formamide, N-methylacetamide, N-methylformamide, glycerol, and the like, and mixtures thereof. Illustrative polar aprotic solvents include, but are not limited to dimethylformamide (DMF), dimethylacetamide (DMAC), 1,3-dimethyl-3,4,5,6-tetrahydro-2(1H)-pyrimidinone (DMPU), 1,3-dimethyl-2-imidazolidinone (DMI), N-methylpyrrolidinone (NMP), acetonitrile, dimethylsulfoxide (DMSO), propionitrile, ethyl formate, methyl acetate, hexachloroacetone, HMPA, HMPT, acetone, ethyl methyl ketone, ethyl acetate, isopropyl acetate, t-butyl acetate, sulfolane, N,N-dimethylpropionamide, nitromethane, nitrobenzene, tetrahydrofuran (THF), methyl tetrahydrofuran, dioxane, polyethers, and the like, and mixtures thereof. The processes may also be performed in the presence of an additional base. Illustrative bases include, but are not limited to DBU, DABCO, TEA, DIPEA, piperidine, and the like, and mixtures thereof.

In another illustrative embodiment, processes are described for preparing compounds of formulae -continued

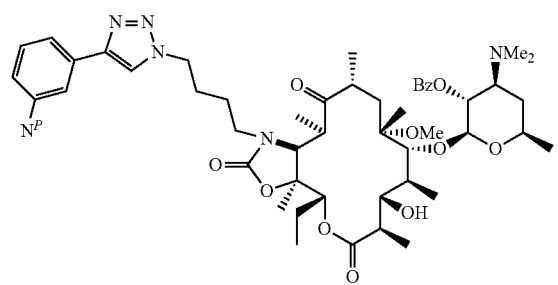
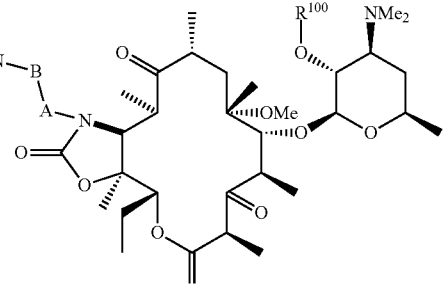
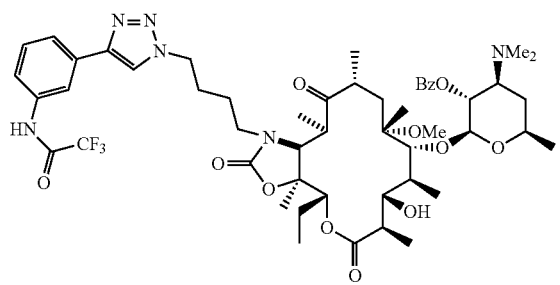
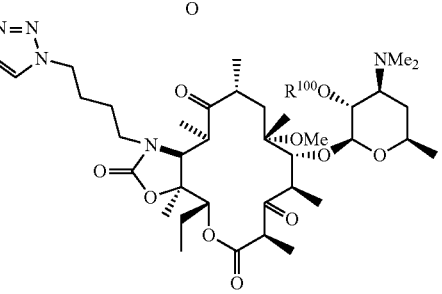
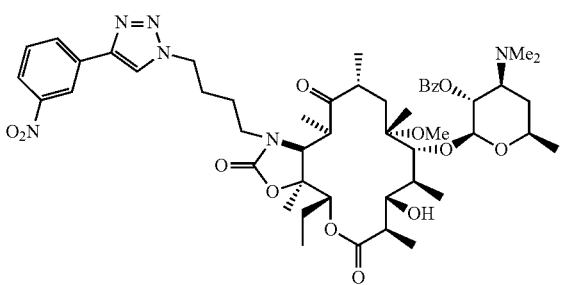
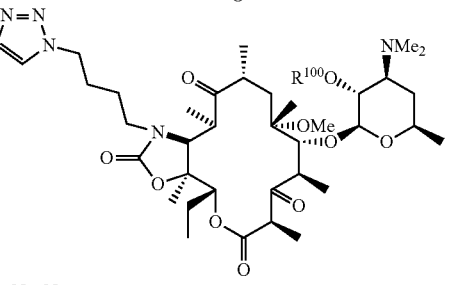
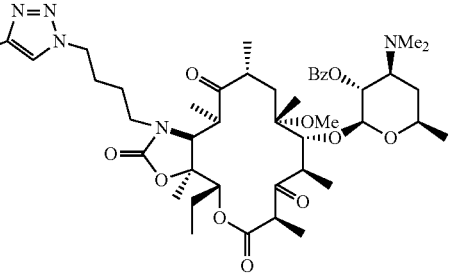
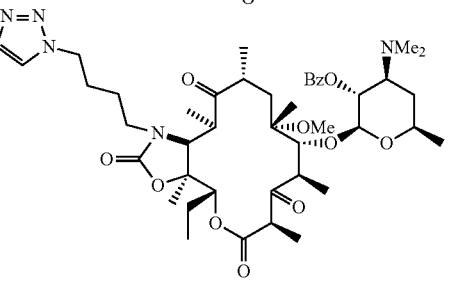

and salts thereof. The processes are generally performed in the presence of an acid. Illustrative acids include, but are not limited to, hydrochloric acid, hydrobromic acid, sulfuric acid, nitric acid, phosphoric acid, perchloric acid, trifluoroacetic acid, formic acid, hydrofluoric acid, and the like, and mixtures thereof. In one variation, the acid is hydrochloric acid. The processes are generally performed in a solvent such as water, a polar organic solvent, including alcohols such as methanol, ethanol, isopropanol, n-propanol, tert-butanol, n-butanol, and the like, and mixtures thereof. The processes may be performed at a wide variety of temperatures, including temperatures in the range from about 0° C. to about 70° C., and illustratively in the range from about 20° C. to about 60° C.

In another illustrative embodiment, processes are for preparing compounds of formula

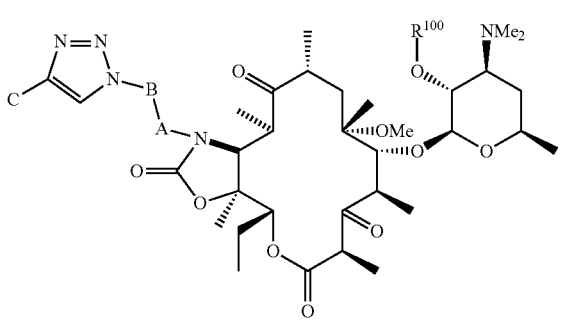

and salts thereof. The processes are generally performed in the presence of an oxidizing agent. Illustrative oxidizing reagents and conditions, include but are not limited to Corey-Kim oxidation, such as dimethylsulfide/N-chlorosuccinimide (DMS/NCS), di-n-butylsulfide/N-chlorosuccinimide, Dess-Martin reagent, Pfitzner-Moffat methods and modifications thereof, Swern conditions, such as DMSO/oxalyl chloride, DMSO/phosphorous pentoxide, DMSO/p-toluene sulfonyl chloride, DMSO/acetic anhydride, DMSO/trifluoroacetic anhydride, and DMSO/thionyl chloride, manganese, chromium and selenium reagents, tertiary amine oxides, Ni(Ac)$_2$/hypochlorite, DMSO/EDAC.HCl/pyridine.TFA and the like, and variations thereof, such as by including one or more phase-transfer catalysts.

In another illustrative embodiment, process are described for preparing compounds of formulae

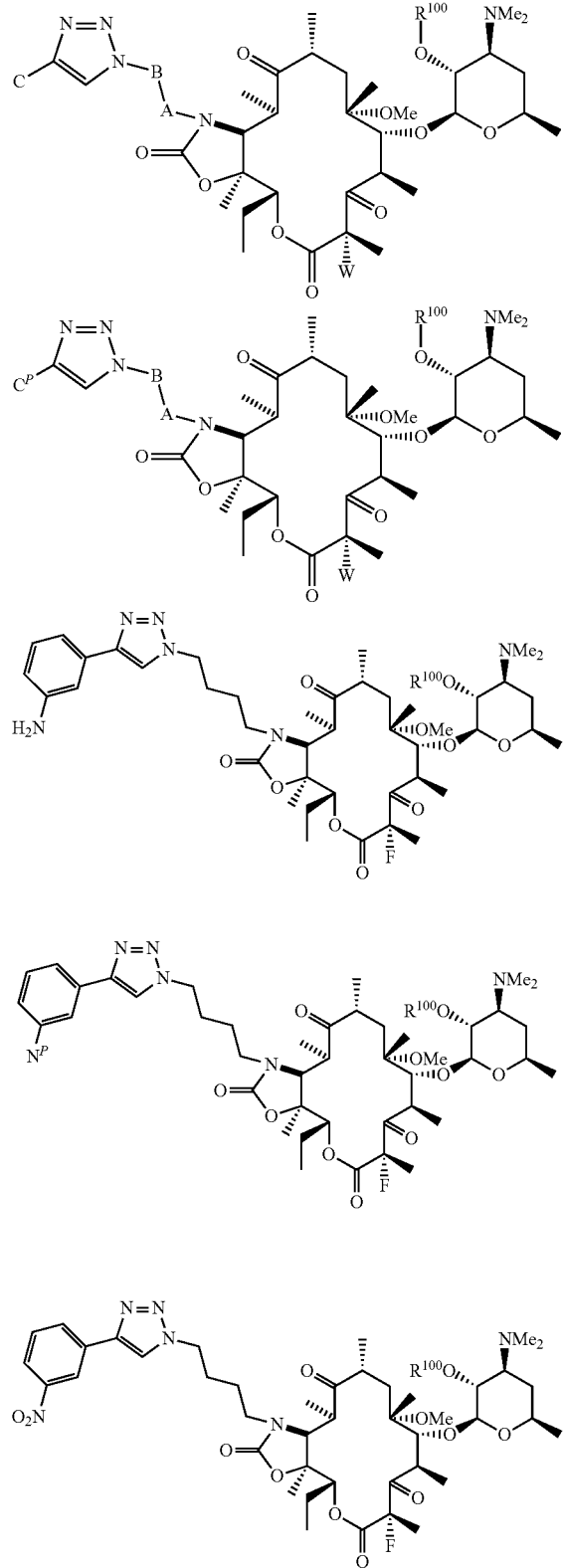

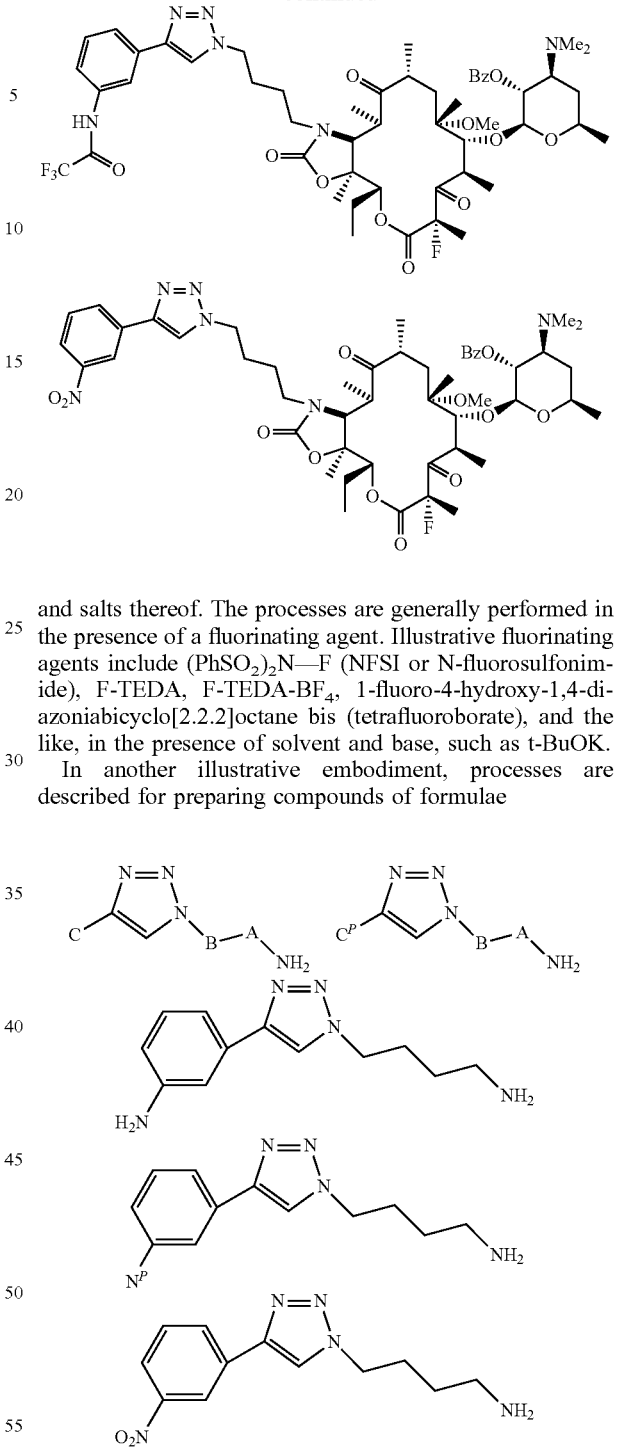

and salts thereof. The processes are generally performed in the presence of a fluorinating agent. Illustrative fluorinating agents include (PhSO$_2$)$_2$N—F (NFSI or N-fluorosulfonimide), F-TEDA, F-TEDA-BF$_4$, 1-fluoro-4-hydroxy-1,4-diazoniabicyclo[2.2.2]octane bis (tetrafluoroborate), and the like, in the presence of solvent and base, such as t-BuOK.

In another illustrative embodiment, processes are described for preparing compounds of formulae and salts thereof via Huisgen cyclization in the presence of a copper catalyst and base. The Huisgen cyclization is generally performed either solvent-free, in water or in an organic solvent such as acetonitrile or toluene, in the presence of base. Illustrative bases include but are not limited to organic bases, including alkyl and heteroaryl bases, such as triethylamine, diisopropylethylamine, DABCO, pyridine, lutidine, and the like, and inorganic bases, such as NaOH, KOH, K$_2$CO$_3$, NaHCO$_3$, and the like. The base is illustratively diisopropyl ethyl amine (DIPEA). The reaction is carried out at temperatures ranging from 20° C. to 80° C. The reaction may also be promoted with the use of a catalyst, including but not limited to a copper halide, illustratively copper iodide. The ratio of CuI to azide is illustratively from about 0.01 to 1 to about 0.1 to 1. In an alternate embodiment, the catalyst is an organic catalyst, such as phenolphthalein. Additional reaction conditions are described by Sharpless et al. in U.S. Patent Application Publication No. US 2005/0222427, Liang et al. in Bioorg. Med. Chem. Lett. 15 (2005) 1307-1310, and Romero et al. in Tetrahedron Letters 46 (2005) 1483-1487, the disclosures of which are incorporated herein by reference.

In another illustrative embodiment, processes are described for deprotecting compounds of formula

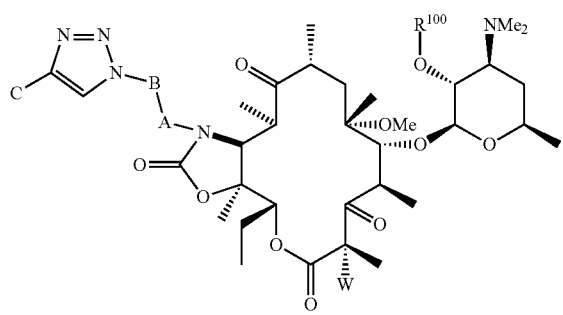

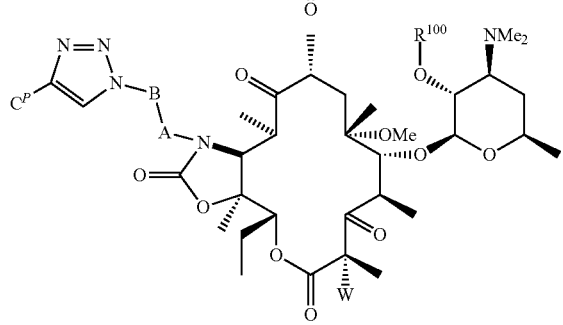

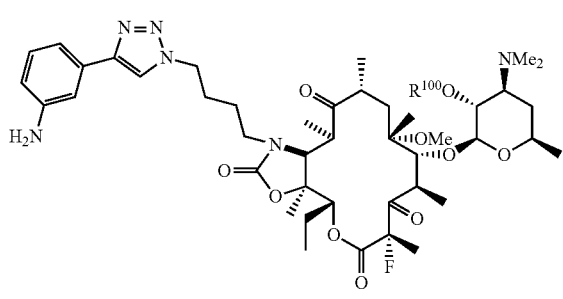

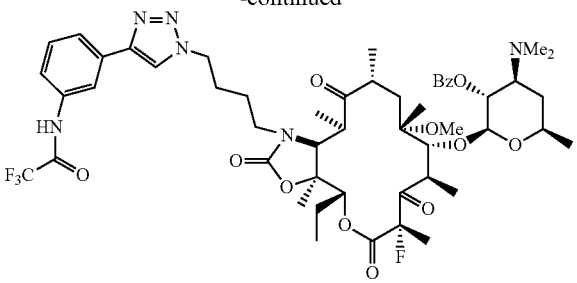

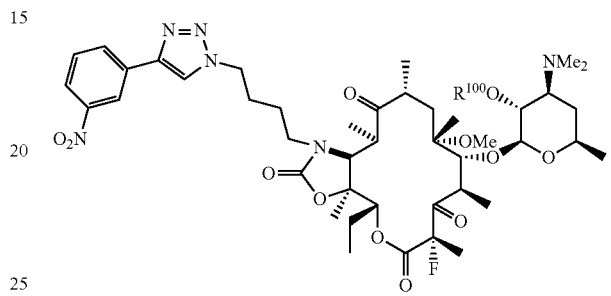

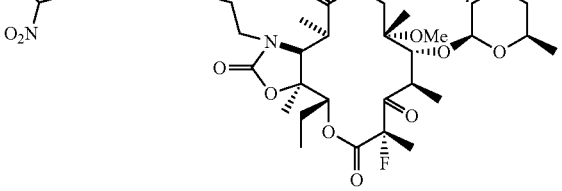

and salts thereof with an alcohol to prepare the corresponding deprotected compound of formula (I). Illustrative alcohols include, but are not limited to, methanol, ethanol, n-propanol, isopropanol, tert-butanol, n-butanol or mixtures thereof. Illustratively, the alcohol is methanol. The reaction may be performed at a temperature of about 0° C. to about 100° C., or at about 20° C. to about 70° C. The reaction may also be performed in the presence of mineral acid, such as a mineral acid selected from HCl, $H_2SO_4$ and the like, and mixtures thereof. In one illustrative embodiment the reaction is carried out in methanol at a temperature of about 55° C.

In another illustrative embodiment, processes are described for reducing compounds of formula

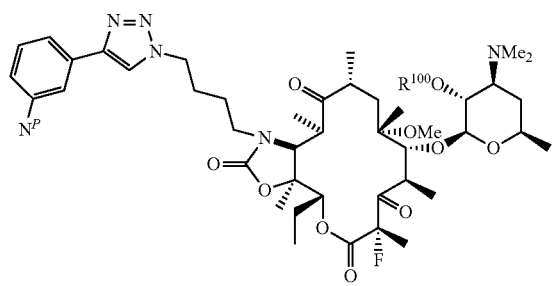

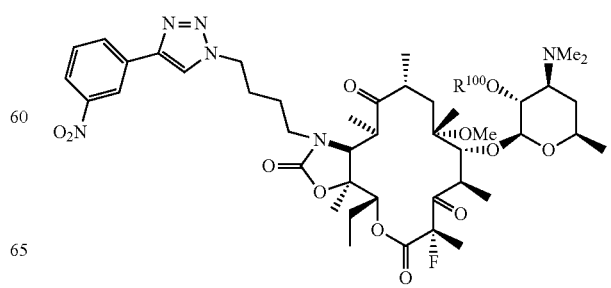

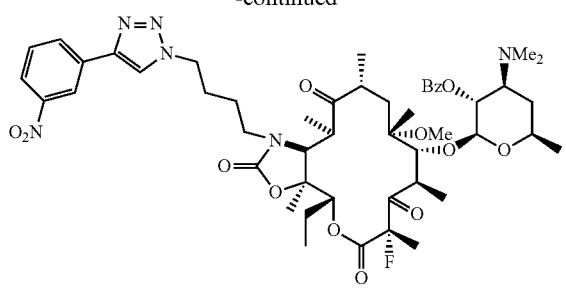

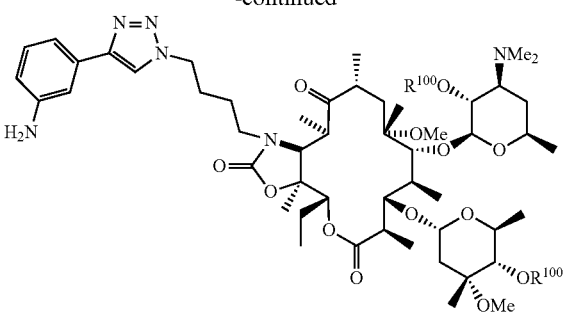

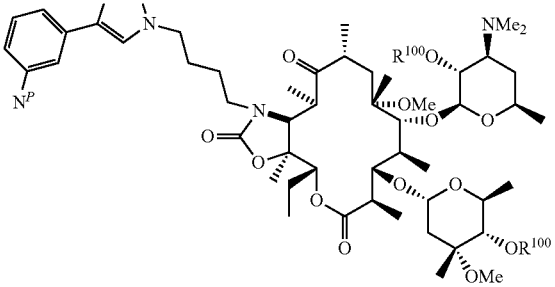

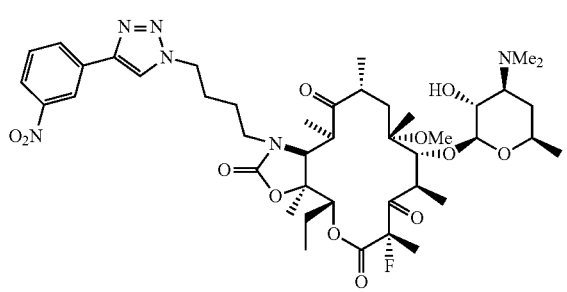

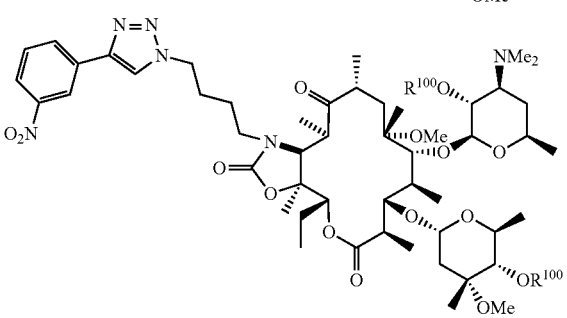

and salts thereof. The processes are generally performed in the presence of a reducing agent. Illustrative reducing agents include, but are not limited to, hydrogen gas, iron and an acid, transfer hydrogenation agents, Raney-Ni, nickel sponge, metal catalysts, such as Pt, Pd, and the like.

In another illustrative embodiment, described herein are compounds of formulae

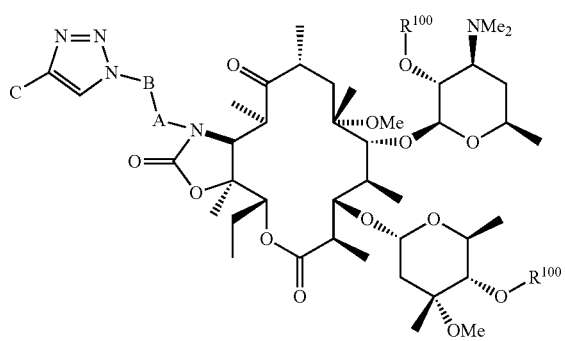

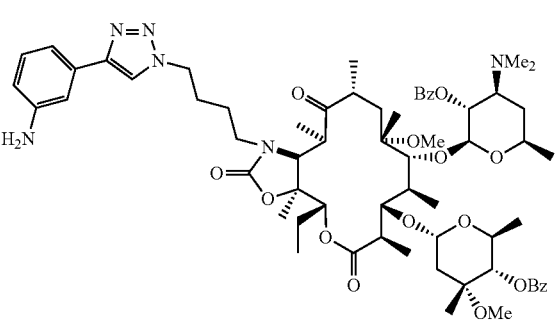

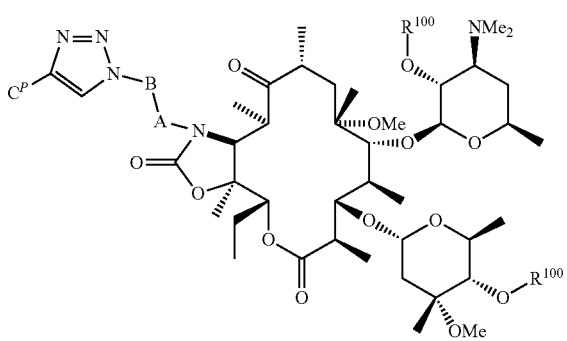

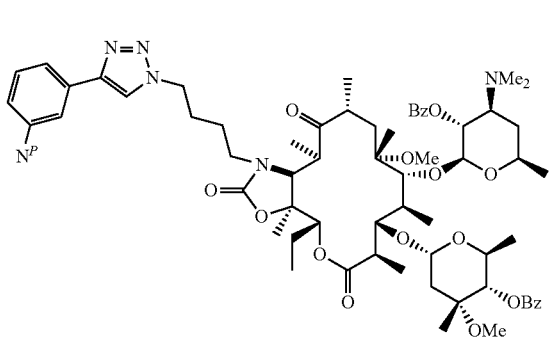

47
-continued
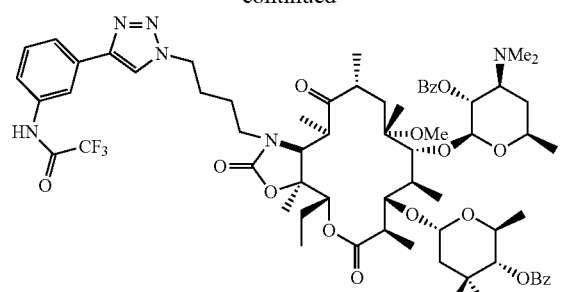
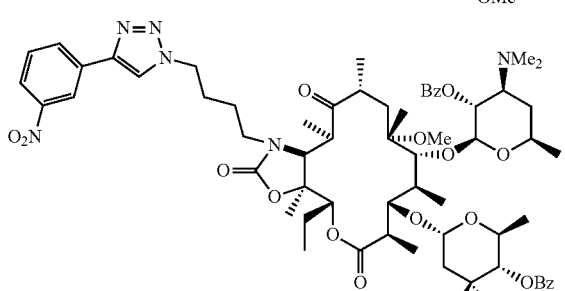
and salts thereof.
In another illustrative embodiment, described herein are compounds of formulae
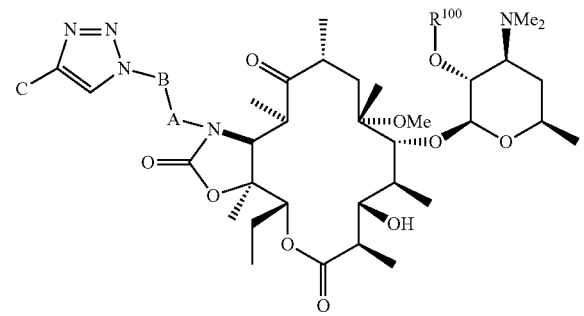
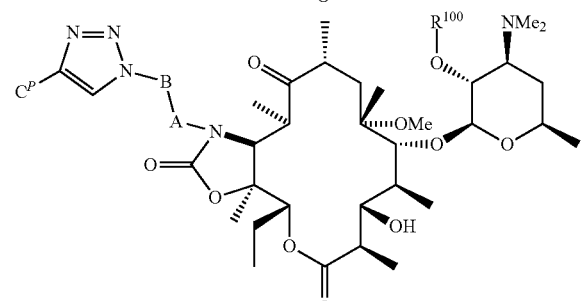
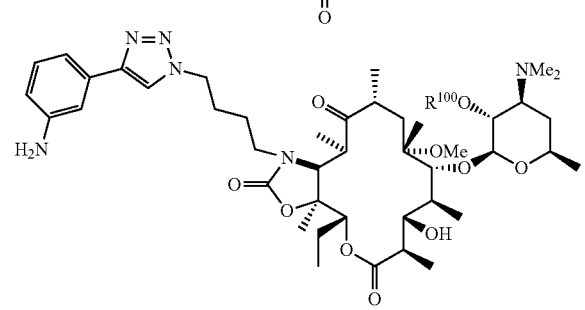
48
-continued
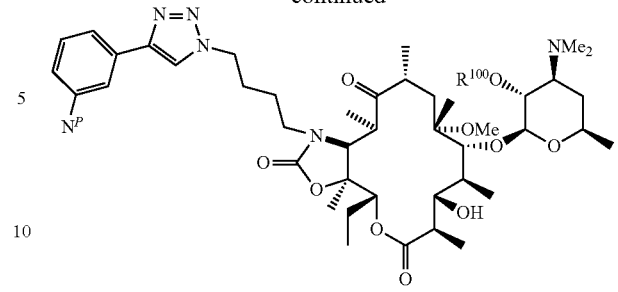
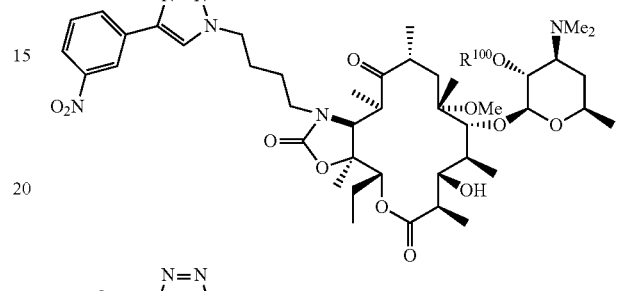
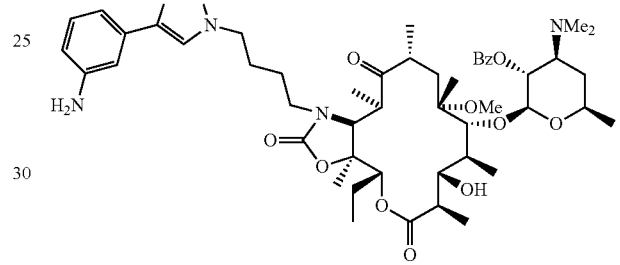
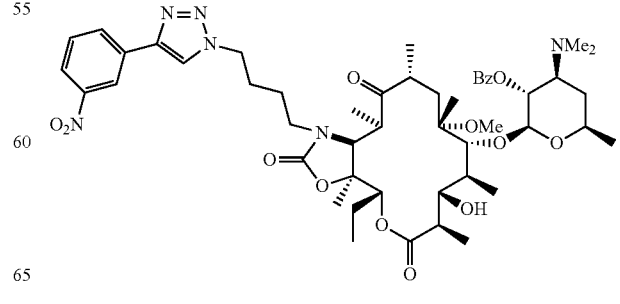
and salts thereof.

In another illustrative embodiment, described herein are compounds of formulae
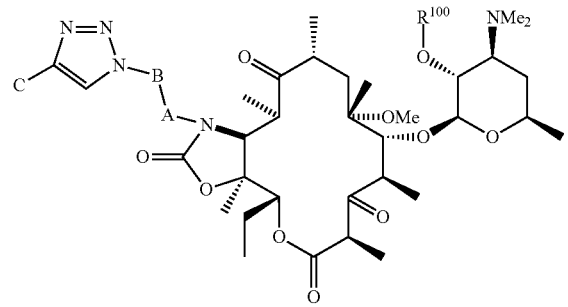
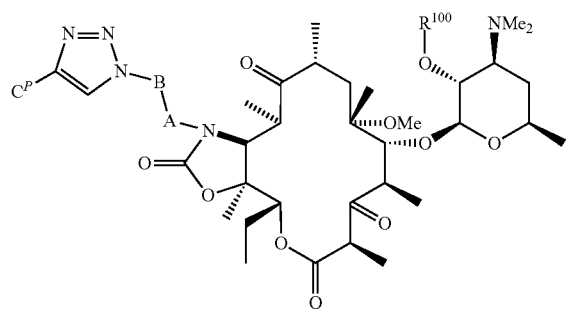
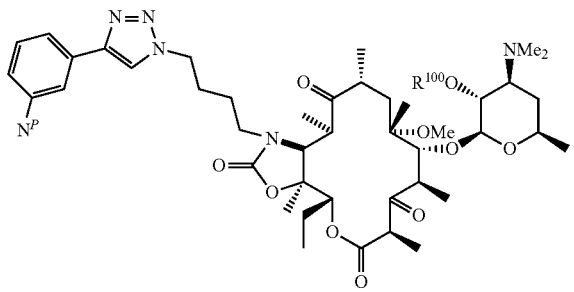
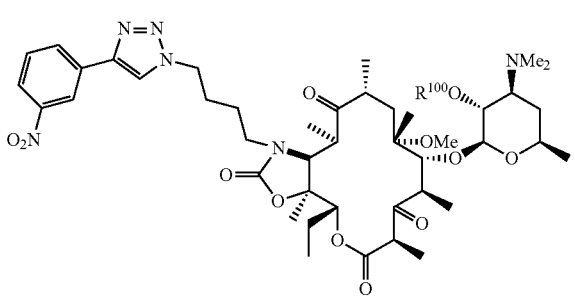
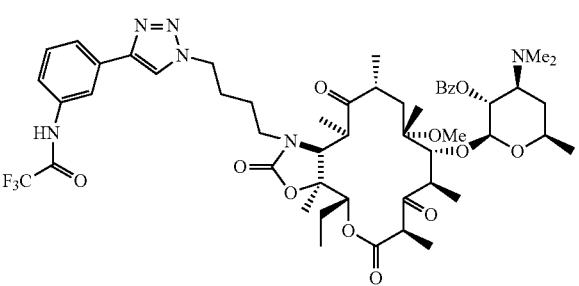
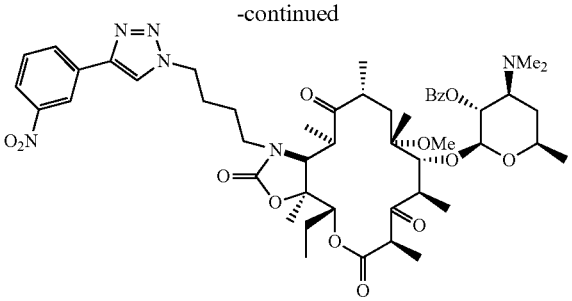
and salts thereof.
In another illustrative embodiment, described herein are compounds of formulae
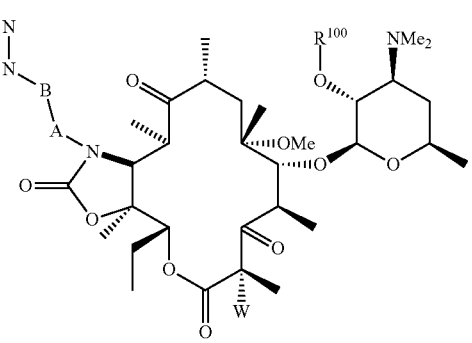
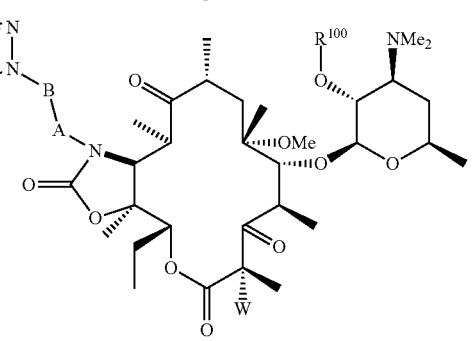
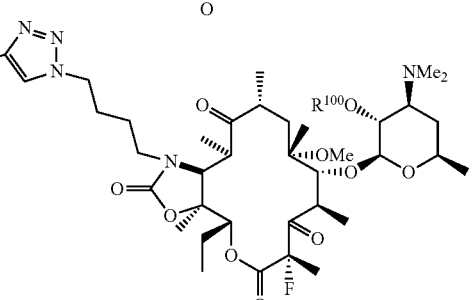
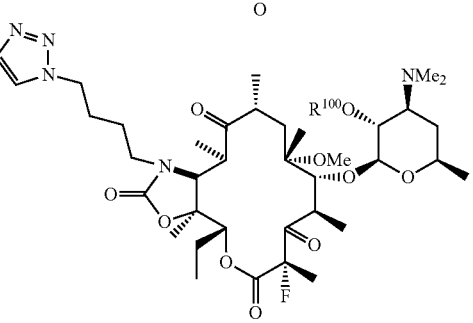

-continued

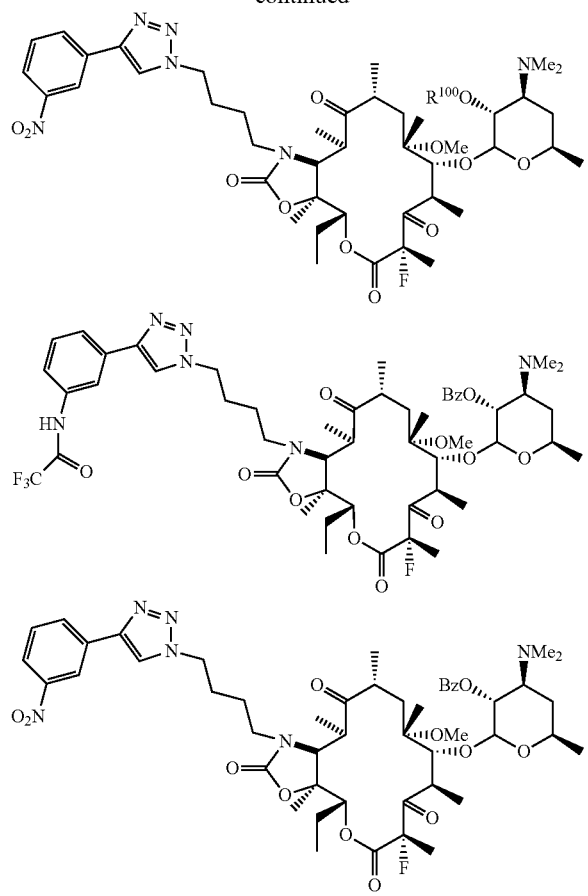

and salts thereof.

In another illustrative embodiment, described herein are compounds of formulae

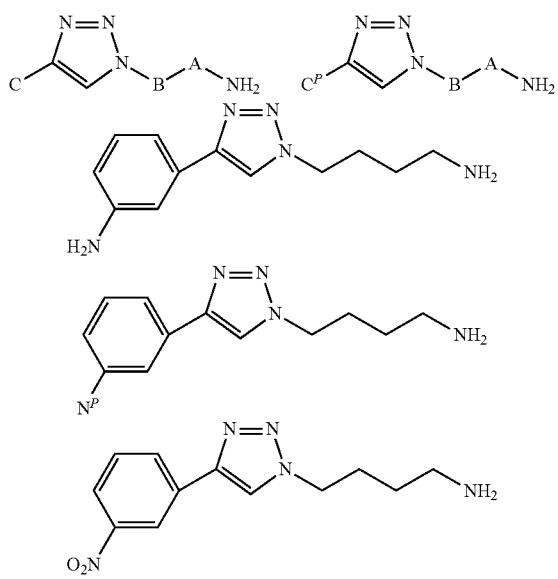

and salts thereof. In another embodiment, $N^P$ is an amide, or carbamate, such as Bz-NH, $CF_3C(O)$—NH, Cbz-NH, Boc-NY, Fmoc-NY, BsMoc-NH, Trityl-NH, MeOTrityl ((4-methoxyphenyl)diphenylmethyl)-NH, and the like.

In another illustrative embodiment, described herein are compounds of formulae

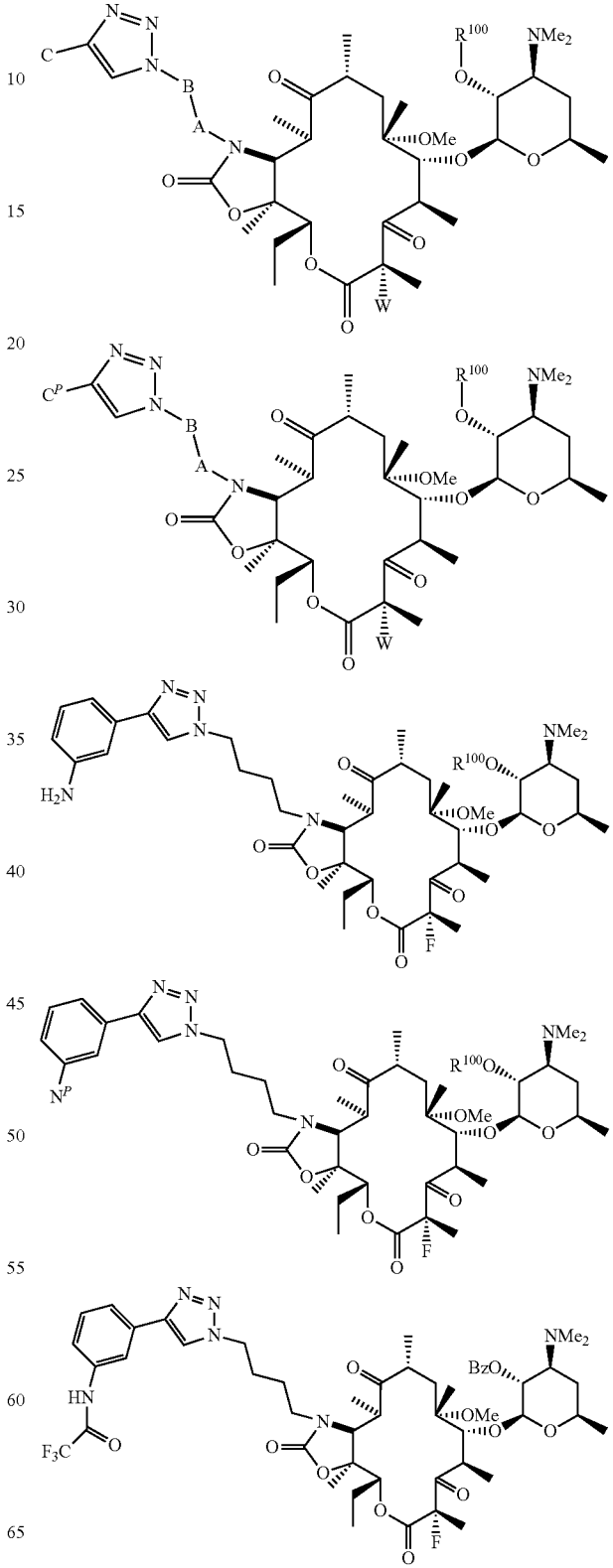

-continued

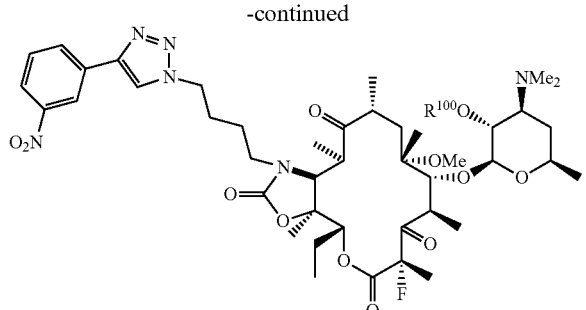

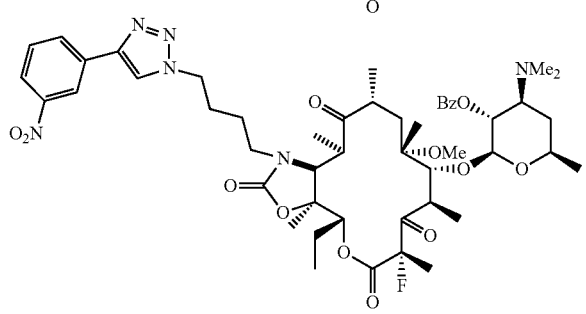

and salts thereof.

In another illustrative embodiment, described herein are compounds of formulae

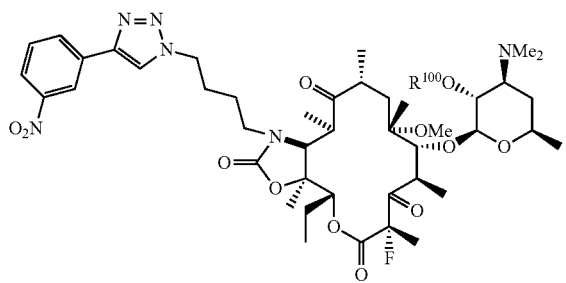

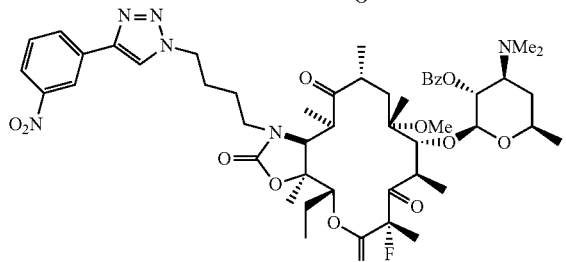

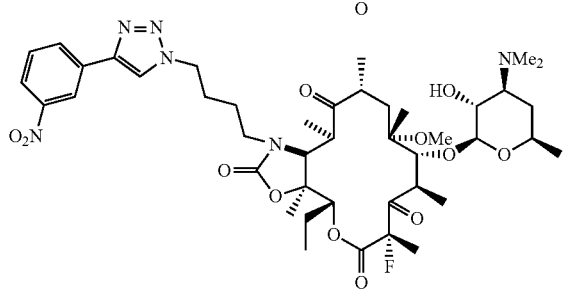

and salts thereof.

It is to be understood that in each of the foregoing embodiments, in each instance, the selection of each of $R^{100}$, $N^P$, A, B, C, $C^P$, W, and L is independently made from any of the species, subgenera, and genera described herein. In addition, it is to be understood that every combination of each of those selections of $R^{100}$, $N^P$, A, B, C, $C^P$, W, and L is described herein, including any combinations of species thereof, subgenera thereof, and genera thereof.

In each of the foregoing and each of the following embodiments, it is also to be understood that the formulae include and represent any and all crystalline forms, partially crystalline forms, and non-crystalline and/or amorphous forms of the compounds.

In each of the foregoing and each of the following embodiments, it is also to be understood that the formulae include and represent not only all pharmaceutically acceptable salts of the compounds, but also include any and all hydrates and/or solvates of the compound formulae. It is appreciated that certain functional groups, such as the hydroxy, amino, and like groups form complexes and/or coordination compounds with water and/or various solvents, in the various physical forms of the compounds. Accordingly, the above formulae are to be understood to be a description of such hydrates and/or solvates, including pharmaceutically acceptable solvates.

As used herein, the term "solvates" refers to compounds described herein complexed with a solvent molecule. It is appreciated that compounds described herein may form such complexes with solvents by simply mixing the compounds with a solvent, or dissolving the compounds in a solvent. It is appreciated that where the compounds are to be used as pharmaceuticals, such solvents are pharmaceutically acceptable solvents. It is further appreciated that where the compounds are to be used as pharmaceuticals, the relative amount of solvent that forms the solvate should be less than established guidelines for such pharmaceutical uses, such as less than International Conference on Harmonization (ICH) Guidelines. It is to be understood that the solvates may be isolated from excess solvent by evaporation, precipitation, and/or crystallization. In some embodiments, the solvates are amorphous, and in other embodiments, the solvates are crystalline.

As used herein, the term "alkyl" includes a chain of carbon atoms, which is optionally branched. As used herein, the terms "alkenyl" and "alkynyl" each include a chain of carbon atoms, which is optionally branched, and include at least one double bond or triple bond, respectively. It is to be understood that alkynyl may also include one or more double bonds. It is to be further understood that in certain embodiments, alkyl is advantageously of limited length, including $C_1$-$C_{24}$, $C_1$-$C_{12}$, $C_1$-$C_8$, $C_1$-$C_6$, and $C_1$-$C_4$, and $C_2$-$C_{24}$, $C_2$-$C_{12}$, $C_2$-$C_8$, $C_2$-$C_6$, and $C_2$-$C_4$, and the like Illustratively, such particularly limited length alkyl groups, including $C_1$-$C_8$, $C_1$-$C_6$, and $C_1$-$C_4$, and $C_2$-$C_8$, $C_2$-$C_6$, and $C_2$-$C_4$, and the like may be referred to as lower alkyl. It is to be further understood that in certain embodiments alkenyl and/or alkynyl may each be advantageously of limited length, including $C_2$-$C_{24}$, $C_2$-$C_{12}$, $C_2$-$C_8$, $C_2$-$C_6$, and $C_2$-$C_4$, and $C_3$-$C_{24}$, $C_3$-$C_{12}$, $C_3$-$C_8$, $C_3$-$C_6$, and $C_3$-$C_4$, and the like Illustratively, such particularly limited length alkenyl and/or alkynyl groups, including $C_2$-$C_8$, $C_2$-$C_6$, and $C_2$-$C_4$, and $C_3$-$C_8$, $C_3$-$C_6$, and $C_3$-$C_4$, and the like may be referred to as lower alkenyl and/or alkynyl. It is appreciated herein that shorter alkyl, alkenyl, and/or alkynyl groups may add less lipophilicity to the compound and accordingly will have different pharmacokinetic behavior. In embodiments of the invention described herein, it is to be understood, in each case, that the recitation of alkyl refers to alkyl as defined herein, and optionally lower alkyl. In embodiments of the invention described herein, it is to be understood, in each case, that the recitation of alkenyl refers to alkenyl as defined herein, and optionally lower alkenyl. In embodiments of the invention described herein, it is to be understood, in each case, that the recitation of alkynyl refers to alkynyl as defined herein, and optionally lower alkynyl. Illustrative alkyl, alkenyl, and alkynyl groups are, but not limited to, methyl, ethyl, n-propyl, isopropyl, n-butyl, isobutyl, sec-butyl, tert-butyl, pentyl, 2-pentyl, 3-pentyl, neopentyl, hexyl, heptyl, octyl, and the like, and the corresponding groups containing one or more double and/or triple bonds, or a combination thereof.

As used herein, the term "alkylene" includes a divalent chain of carbon atoms, which is optionally branched. As used herein, the term "alkenylene" and "alkynylene" includes a divalent chain of carbon atoms, which is optionally branched, and includes at least one double bond or triple bond, respectively. It is to be understood that alkynylene may also include one or more double bonds. It is to be further understood that in certain embodiments, alkylene is advantageously of limited length, including $C_1$-$C_{24}$, $C_1$-$C_{12}$, $C_1$-$C_8$, $C_1$-$C_6$, and $C_1$-$C_4$, and $C_2$-$C_{24}$, $C_2$-$C_{12}$, $C_2$-$C_8$, $C_2$-$C_6$, and $C_2$-$C_4$, and the like. Illustratively, such particularly limited length alkylene groups, including $C_1$-$C_8$, $C_1$-$C_6$, and $C_1$-$C_4$, and $C_2$-$C_8$, $C_2$-$C_6$, and $C_2$-$C_4$, and the like may be referred to as lower alkylene. It is to be further understood that in certain embodiments alkenylene and/or alkynylene may each be advantageously of limited length, including $C_2$-$C_{24}$, $C_2$-$C_{12}$, $C_2$-$C_8$, $C_2$-$C_6$, and $C_2$-$C_4$, and $C_3$-$C_{24}$, $C_3$-$C_{12}$, $C_3$-$C_8$, $C_3$-$C_6$, and $C_3$-$C_4$, and the like. Illustratively, such particularly limited length alkenylene and/or alkynylene groups, including $C_2$-$C_8$, $C_2$-$C_6$, and $C_2$-$C_4$, and $C_3$-$C_8$, $C_3$-$C_6$, and $C_3$-$C_4$, and the like may be referred to as lower alkenylene and/or alkynylene. It is appreciated herein that shorter alkylene, alkenylene, and/or alkynylene groups may add less lipophilicity to the compound and accordingly will have different pharmacokinetic behavior. In embodiments of the invention described herein, it is to be understood, in each case, that the recitation of alkylene, alkenylene, and alkynylene refers to alkylene, alkenylene, and alkynylene as defined herein, and optionally lower alkylene, alkenylene, and alkynylene. Illustrative alkyl groups are, but not limited to, methylene, ethylene, n-propylene, isopropylene, n-butylene, isobutylene, sec-butylene, pentylene, 1,2-pentylene, 1,3-pentylene, hexylene, heptylene, octylene, and the like.

As used herein, the term "cycloalkyl" includes a chain of carbon atoms, which is optionally branched, where at least a portion of the chain in cyclic. It is to be understood that cycloalkylalkyl is a subset of cycloalkyl. It is to be understood that cycloalkyl may be polycyclic. Illustrative cycloalkyl include, but are not limited to, cyclopropyl, cyclopentyl, cyclohexyl, 2-methylcyclopropyl, cyclopentyleth-2-yl, adamantyl, and the like. As used herein, the term "cycloalkenyl" includes a chain of carbon atoms, which is optionally branched, and includes at least one double bond, where at least a portion of the chain in cyclic. It is to be understood that the one or more double bonds may be in the cyclic portion of cycloalkenyl and/or the non-cyclic portion of cycloalkenyl. It is to be understood that cycloalkenylalkyl and cycloalkylalkenyl are each subsets of cycloalkenyl. It is to be understood that cycloalkyl may be polycyclic. Illustrative cycloalkenyl include, but are not limited to, cyclopentenyl, cyclohexylethen-2-yl, cycloheptenylpropenyl, and the like. It is to be further understood that chain forming cycloalkyl and/or cycloalkenyl is advantageously of limited length, including $C_3$-$C_{24}$, $C_3$-$C_{12}$, $C_3$-$C_8$, $C_3$-$C_6$, and $C_5$-$C_6$. It is appreciated herein that shorter alkyl and/or alkenyl chains forming cycloalkyl and/or cycloalkenyl, respectively, may add less lipophilicity to the compound and accordingly will have different pharmacokinetic behavior.

As used herein, the term "heteroalkyl" includes a chain of atoms that includes both carbon and at least one heteroatom, and is optionally branched. Illustrative heteroatoms include nitrogen, oxygen, and sulfur. In certain variations, illustrative heteroatoms also include phosphorus, and selenium. As used herein, the term "cycloheteroalkyl" including heterocyclyl and heterocycle, includes a chain of atoms that includes both carbon and at least one heteroatom, such as heteroalkyl, and is optionally branched, where at least a portion of the chain is cyclic. Illustrative heteroatoms include nitrogen, oxygen, and sulfur. In certain variations, illustrative heteroatoms also include phosphorus, and selenium. Illustrative cycloheteroalkyl include, but are not limited to, tetrahydrofuryl, pyrrolidinyl, tetrahydropyranyl, piperidinyl, morpholinyl, piperazinyl, homopiperazinyl, quinuclidinyl, and the like.

As used herein, the term "aryl" includes monocyclic and polycyclic aromatic carbocyclic groups, each of which may be optionally substituted. Illustrative aromatic carbocyclic groups described herein include, but are not limited to, phenyl, naphthyl, and the like. As used herein, the term "heteroaryl" includes aromatic heterocyclic groups, each of which may be optionally substituted. Illustrative aromatic heterocyclic groups include, but are not limited to, pyridinyl, pyrimidinyl, pyrazinyl, triazinyl, tetrazinyl, quinolinyl, quinazolinyl, quinoxalinyl, thienyl, pyrazolyl, imidazolyl, oxazolyl, thiazolyl, isoxazolyl, isothiazolyl, oxadiazolyl, thiadiazolyl, triazolyl, benzimidazolyl, benzoxazolyl, benzthiazolyl, benzisoxazolyl, benzisothiazolyl, and the like.

As used herein, the term "amino" includes the group $NH_2$, alkylamino, and dialkylamino, where the two alkyl groups in dialkylamino may be the same or different, i.e. alkylalkylamino. Illustratively, amino includes methylamino, ethylamino, dimethylamino, methylethylamino, and the like. In addition, it is to be understood that when amino modifies or is modified by another term, such as aminoalkyl, or acylamino, the above variations of the term amino are included therein. Illustratively, aminoalkyl includes $H_2N$-alkyl, methylaminoalkyl, ethylaminoalkyl, dimethylaminoalkyl, methylethylaminoalkyl, and the like. Illustratively, acylamino includes acylmethylamino, acylethylamino, and the like.

As used herein, the term "amino and derivatives thereof" includes amino as described herein, and alkylamino, alkenylamino, alkynylamino, heteroalkylamino, heteroalkenylamino, heteroalkynylamino, cycloalkylamino, cycloalkenylamino, cycloheteroalkylamino, cycloheteroalkenylamino, arylamino, arylalkylamino, arylalkenylamino, arylalkynylamino, heteroarylamino, heteroarylalkylamino, heteroarylalkenylamino, heteroarylalkynylamino, acylamino, and the like, each of which is optionally substituted. The term "amino derivative" also includes urea, carbamate, and the like.

As used herein, the term "hydroxy and derivatives thereof" includes OH, and alkyloxy, alkenyloxy, alkynyloxy, heteroalkyloxy, heteroalkenyloxy, heteroalkynyloxy, cycloalkyloxy, cycloalkenyloxy, cycloheteroalkyloxy, cycloheteroalkenyloxy, aryloxy, arylalkyloxy, arylalkenyloxy, arylalkynyloxy, heteroaryloxy, heteroarylalkyloxy, heteroarylalkenyloxy, heteroarylalkynyloxy, acyloxy, and the like, each of which is optionally substituted. The term "hydroxy derivative" also includes carbamate, and the like.

As used herein, the term "thio and derivatives thereof" includes SH, and alkylthio, alkenylthio, alkynylthio, heteroalkylthio, heteroalkenylthio, heteroalkynylthio, cycloalkylthio, cycloalkenylthio, cycloheteroalkylthio, cycloheteroalkenylthio, arylthio, arylalkylthio, arylalkenylthio, arylalkynylthio, heteroarylthio, heteroarylalkylthio, heteroarylalkenylthio, heteroarylalkynylthio, acylthio, and the like, each of which is optionally substituted. The term "thio derivative" also includes thiocarbamate, and the like.

As used herein, the term "acyl" includes formyl, and alkylcarbonyl, alkenylcarbonyl, alkynylcarbonyl, heteroalkylcarbonyl, heteroalkenylcarbonyl, heteroalkynylcarbonyl, cycloalkylcarbonyl, cycloalkenylcarbonyl, cycloheteroalkylcarbonyl, cycloheteroalkenylcarbonyl, arylcarbonyl, arylalkylcarbonyl, arylalkenylcarbonyl, arylalkynylcarbonyl, heteroarylcarbonyl, heteroarylalkylcarbonyl, heteroarylalkenylcarbonyl, heteroarylalkynylcarbonyl, acylcarbonyl, and the like, each of which is optionally substituted.

As used herein, the term "carbonyl and derivatives thereof" includes the group C(O), C(S), C(NH) and substituted amino derivatives thereof.

As used herein, the term "carboxylic acid and derivatives thereof" includes the group $CO_2H$ and salts thereof, and esters and amides thereof, and CN.

As used herein, the term "sulfinic acid or a derivative thereof" includes $SO_2H$ and salts thereof, and esters and amides thereof.

As used herein, the term "sulfonic acid or a derivative thereof" includes $SO_3H$ and salts thereof, and esters and amides thereof.

As used herein, the term "sulfonyl" includes alkylsulfonyl, alkenylsulfonyl, alkynylsulfonyl, heteroalkylsulfonyl, heteroalkenylsulfonyl, heteroalkynylsulfonyl, cycloalkylsulfonyl, cycloalkenylsulfonyl, cycloheteroalkylsulfonyl, cycloheteroalkenylsulfonyl, arylsulfonyl, arylalkylsulfonyl, arylalkenylsulfonyl, arylalkynylsulfonyl, heteroarylsulfonyl, heteroarylalkylsulfonyl, heteroarylalkenylsulfonyl, heteroarylalkynylsulfonyl, acylsulfonyl, and the like, each of which is optionally substituted.

The term "optionally substituted" as used herein includes the replacement of hydrogen atoms with other functional groups on the radical that is optionally substituted. Such other functional groups illustratively include, but are not limited to, amino, hydroxyl, halo, thiol, alkyl, haloalkyl, heteroalkyl, aryl, arylalkyl, arylheteroalkyl, heteroaryl, heteroarylalkyl, heteroarylheteroalkyl, nitro, sulfonic acids and derivatives thereof, carboxylic acids and derivatives thereof, and the like. Illustratively, any of amino, hydroxyl, thiol, alkyl, haloalkyl, heteroalkyl, aryl, arylalkyl, arylheteroalkyl, heteroaryl, heteroarylalkyl, heteroarylheteroalkyl, and/or sulfonic acid is optionally substituted.

As used herein, the terms "optionally substituted aryl" and "optionally substituted heteroaryl" include the replacement of hydrogen atoms with other functional groups on the aryl or heteroaryl that is optionally substituted. Such other functional groups illustratively include, but are not limited to, amino, hydroxy, halo, thio, alkyl, haloalkyl, heteroalkyl, aryl, arylalkyl, arylheteroalkyl, heteroaryl, heteroarylalkyl, heteroarylheteroalkyl, nitro, sulfonic acids and derivatives thereof, carboxylic acids and derivatives thereof, and the like. Illustratively, any of amino, hydroxy, thio, alkyl, haloalkyl, heteroalkyl, aryl, arylalkyl, arylheteroalkyl, heteroaryl, heteroarylalkyl, heteroarylheteroalkyl, and/or sulfonic acid is optionally substituted.

Illustrative substituents include, but are not limited to, a radical $-(CH_2)_xZ^X$, where x is an integer from 0-6 and $Z^X$ is selected from halogen, hydroxy, alkanoyloxy, including $C_1$-$C_6$ alkanoyloxy, optionally substituted aroyloxy, alkyl, including $C_1$-$C_6$ alkyl, alkoxy, including $C_1$-$C_6$ alkoxy, cycloalkyl, including $C_3$-$C_8$ cycloalkyl, cycloalkoxy, including $C_3$-$C_8$ cycloalkoxy, alkenyl, including $C_2$-$C_6$ alkenyl, alkynyl, including $C_2$-$C_6$ alkynyl, haloalkyl, including $C_1$-$C_6$ haloalkyl, haloalkoxy, including $C_1$-$C_6$ haloalkoxy, halocycloalkyl, including $C_3$-$C_8$ halocycloalkyl, halocycloalkoxy, including $C_3$-$C_8$ halocycloalkoxy, amino, $C_1$-$C_6$ alkylamino, ($C_1$-$C_6$ alkyl)($C_1$-$C_6$ alkyl)amino, alkylcarbonylamino, N—($C_1$-$C_6$ alkyl)alkylcarbonylamino, aminoalkyl, $C_1$-$C_6$ alkylaminoalkyl, ($C_1$-$C_6$ alkyl)($C_1$-$C_6$ alkyl)aminoalkyl, alkylcarbonylaminoalkyl, N—($C_1$-$C_6$ alkyl)alkylcarbonylaminoalkyl, cyano, and nitro; or $Z^X$ is selected from $-CO_2R^4$ and $-CONR^5R^6$, where $R^4$, $R^5$, and $R^6$ are each independently selected in each occurrence from hydrogen, $C_1$-$C_6$ alkyl, aryl-$C_1$-$C_6$ alkyl, and heteroaryl-$C_1$-$C_6$ alkyl.

Illustrative heterocycles include, but are not limited to pyrrolidines, piperidines, oxazolidines, isoxazolidines, thiazolidines, isothiazolidines, pyrrolidinones, piperidinones, oxazolidinones, isoxazolidinones, thiazolidinones, isothiazolidinones, and succinimides.

As used herein, the term "leaving group" refers to a reactive functional group that generates an electrophilic site on the atom to which it is attached such that nucleophiles may be added to the electrophilic site on the atom. Illustrative leaving groups include, but are not limited to, halogens, optionally substituted phenols, acyloxy groups, sulfonoxy groups, and the like. It is to be understood that such leaving groups may be on alkyl, acyl, and the like. Such leaving groups may also be referred to herein as activating groups, such as when the leaving group is present on acyl. In addition, conventional peptide, amide, and ester coupling agents, such as but not limited to PyBop, BOP-Cl, BOP, pentafluorophenol, isobutylchloroformate, and the like, form various intermediates that include a leaving group, as defined herein, on a carbonyl group.

It is to be understood that where members are grouped together in a common manner, such as in a Markush group, the present invention encompasses not only the entire group listed as a whole, but each member of the group individually and all possible subgroups of the main group. Accordingly, for all purposes, the present invention encompasses not only the main group, but also the main group absent one or more of the group members. The present invention also envisages the explicit exclusion of one or more of any of the group members in the claimed invention.

In another embodiment, the following process steps and compounds are each individually described herein.

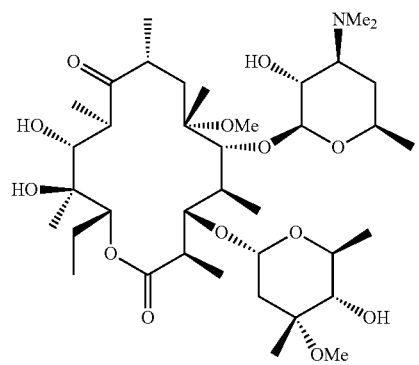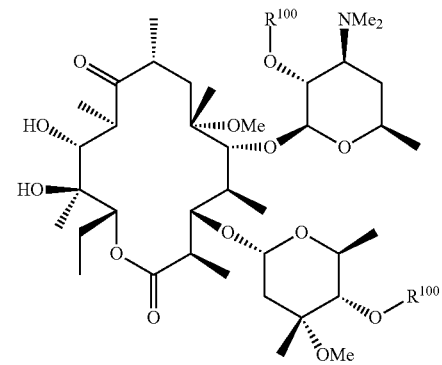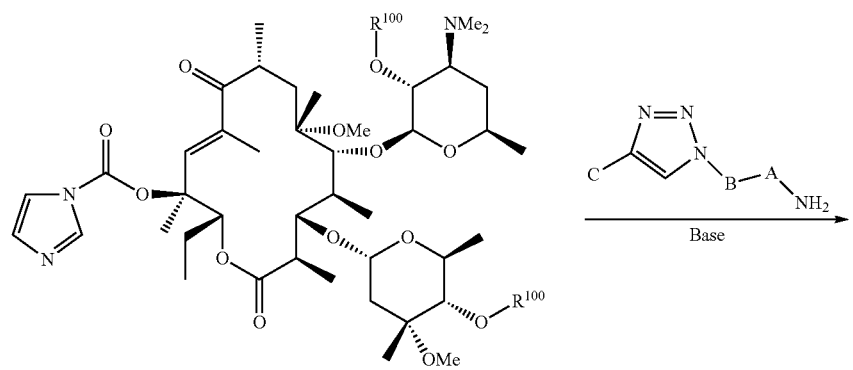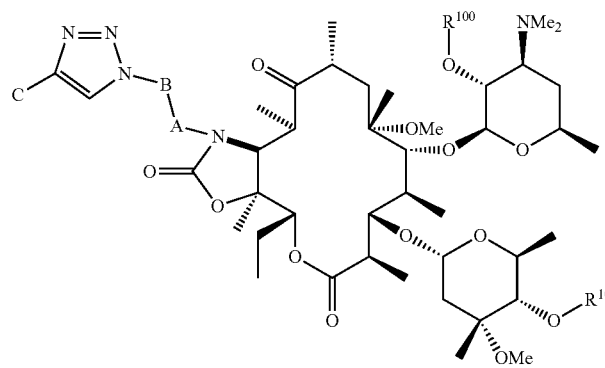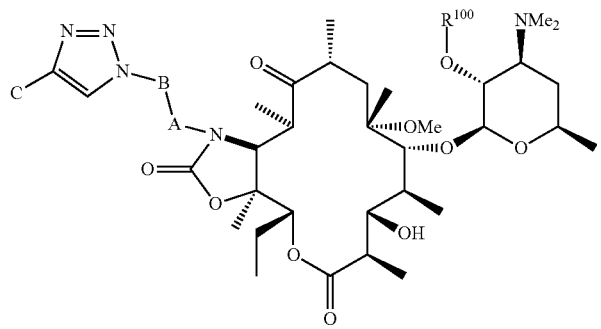

-continued
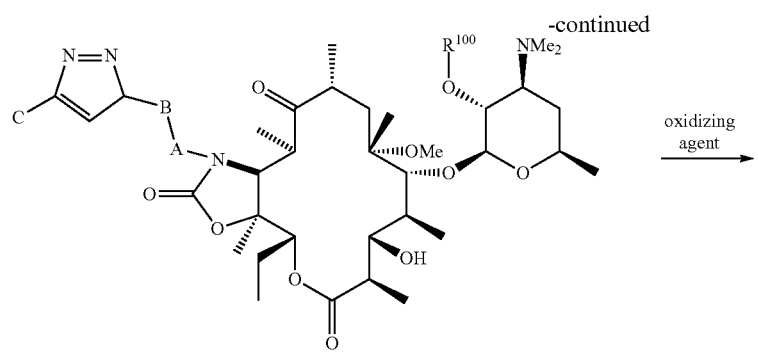
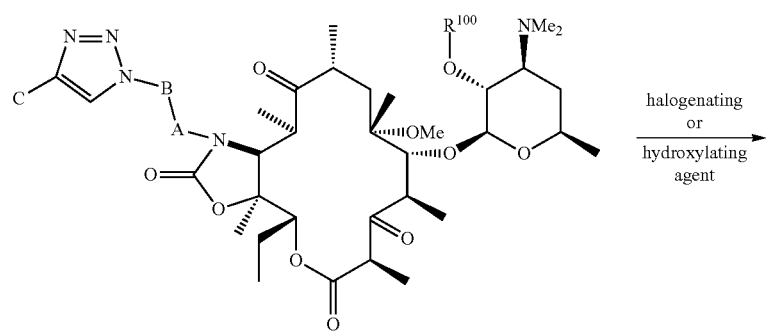
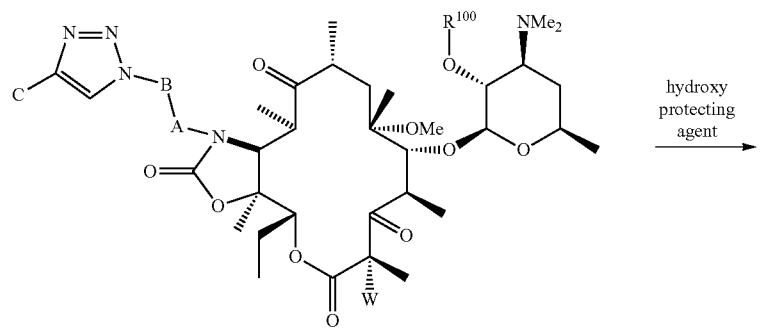
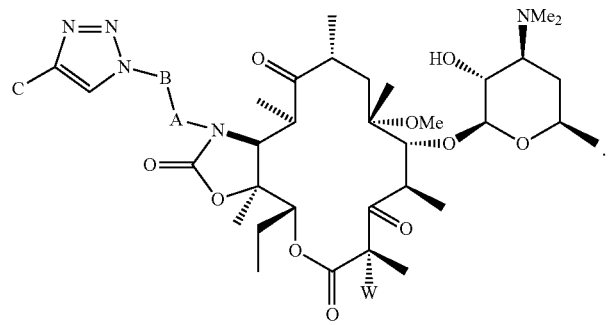
The corresponding process where C is replace by $C^P$ in one or more steps is also described herein.
In another embodiment, the following process steps and compounds are each individually described herein.

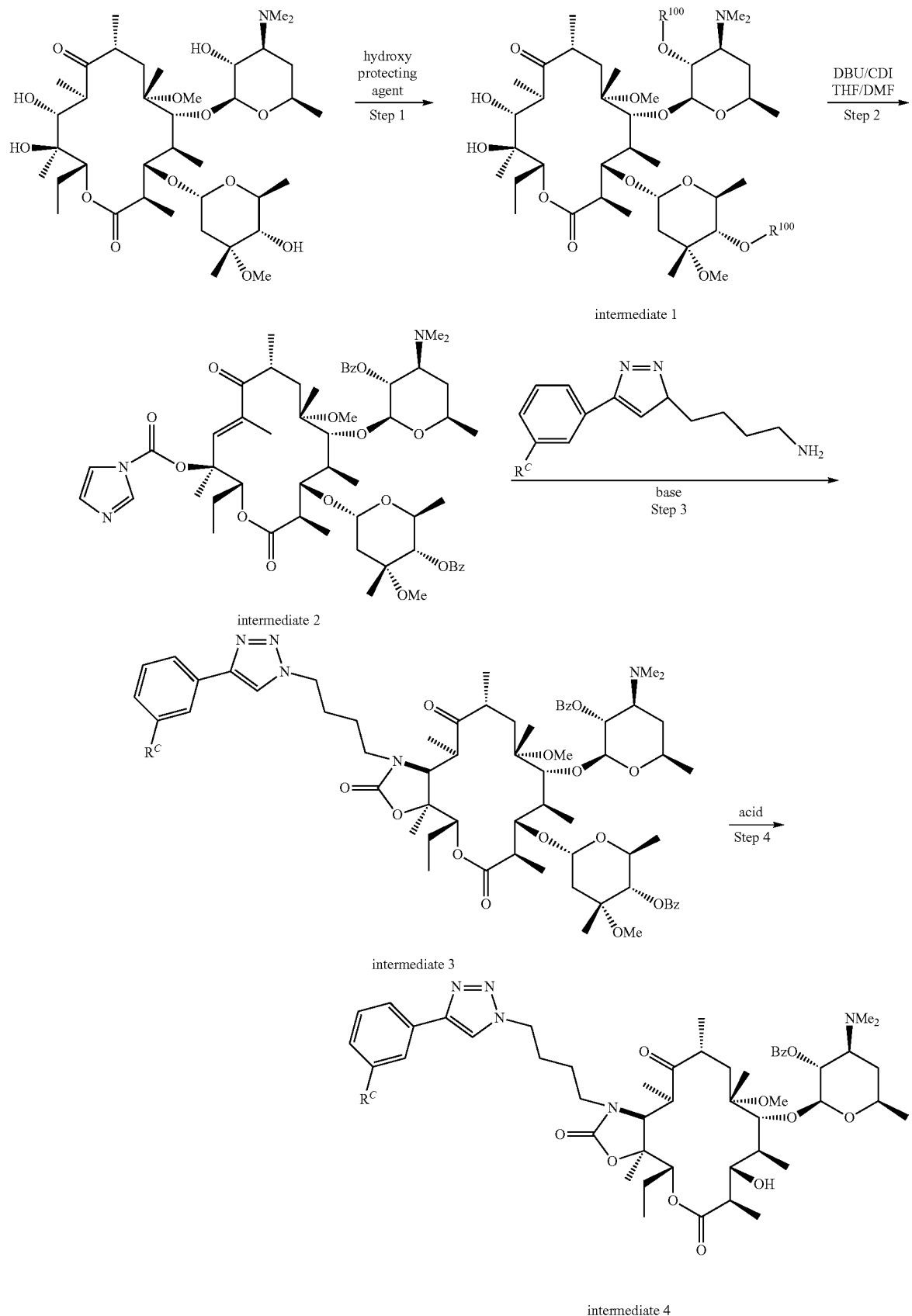

where $R^C$ is amino, or a protected amino derivative such as $N^P$, or nitro. The corresponding process where $R^C$ is $N^P$ is also described herein.
In another embodiment, the following process steps and compounds are each individually described herein.
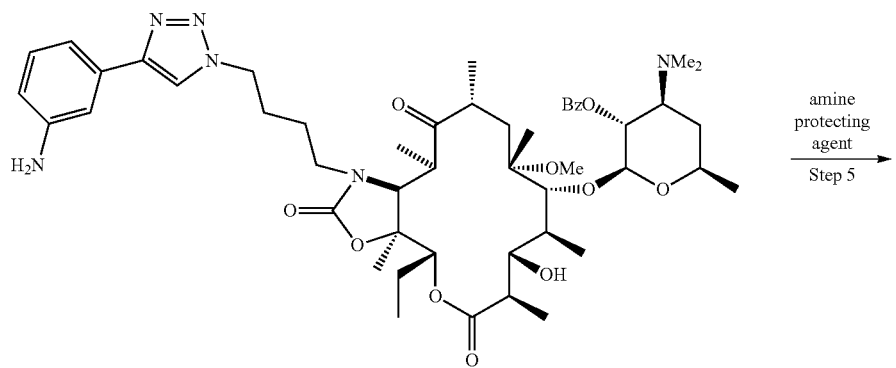
intermediate 4
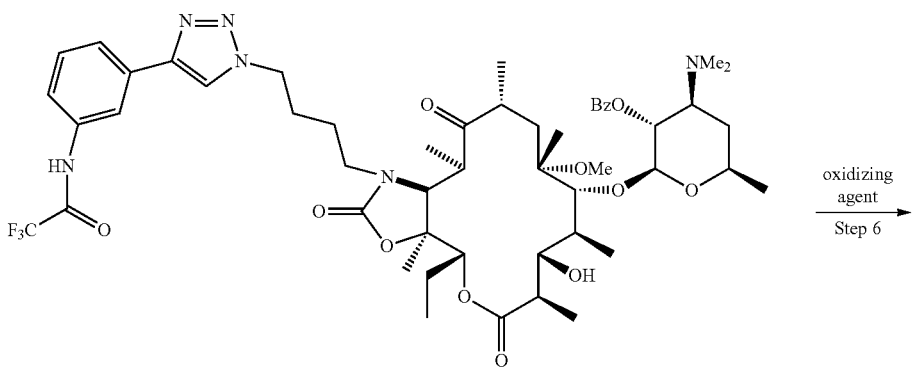
intermediate 5
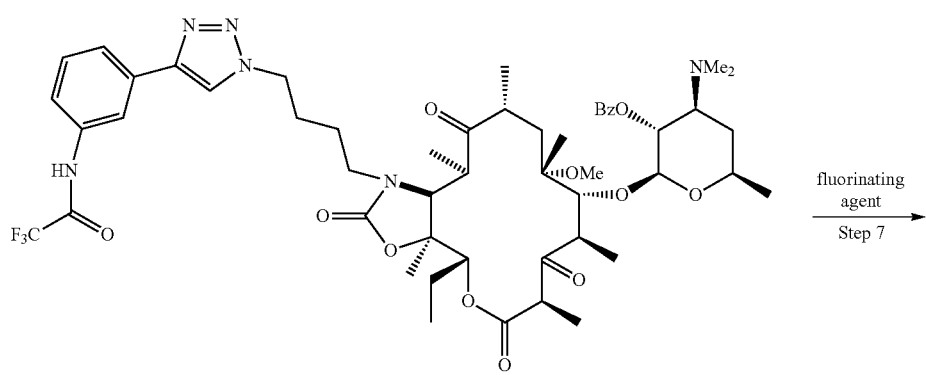
intermediate 6

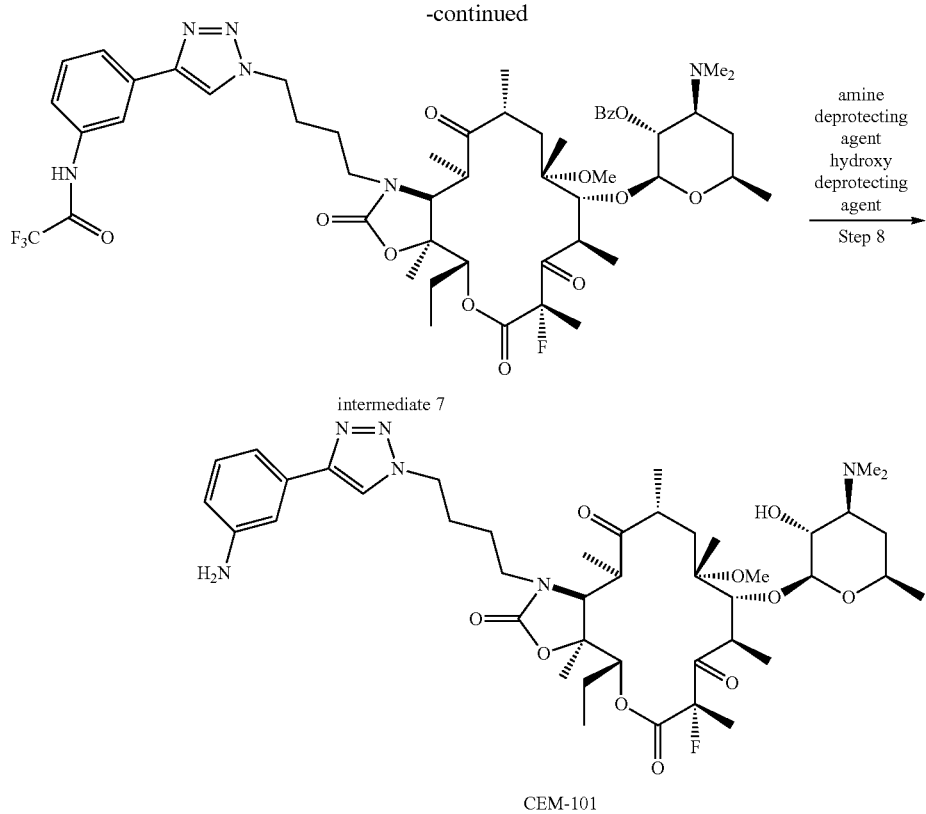
intermediate 7
CEM-101
In another embodiment, the following process steps and compounds are each individually described herein.
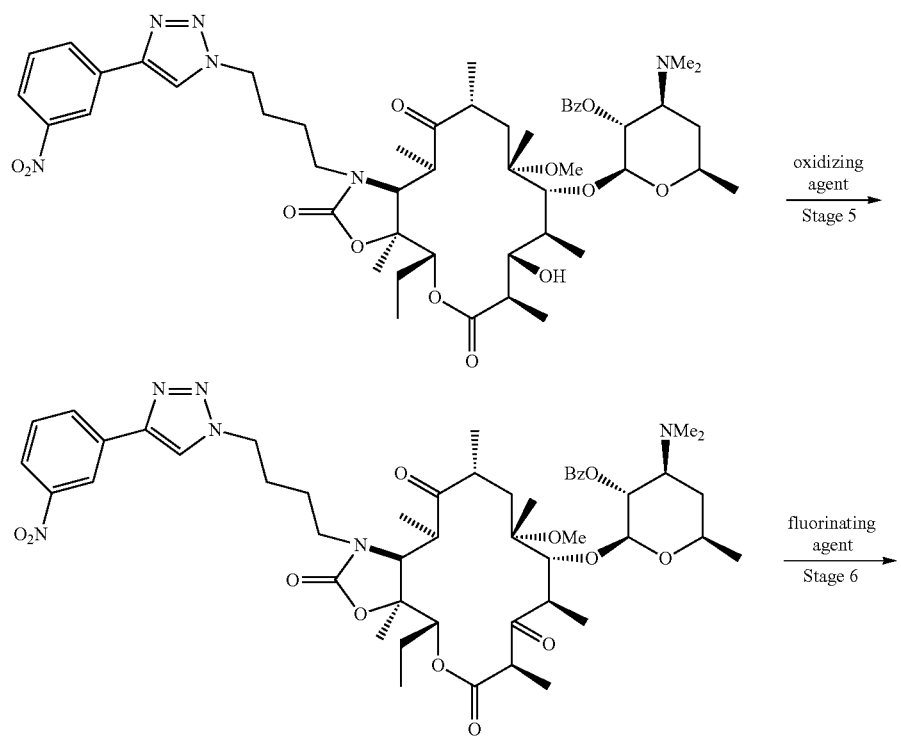

-continued

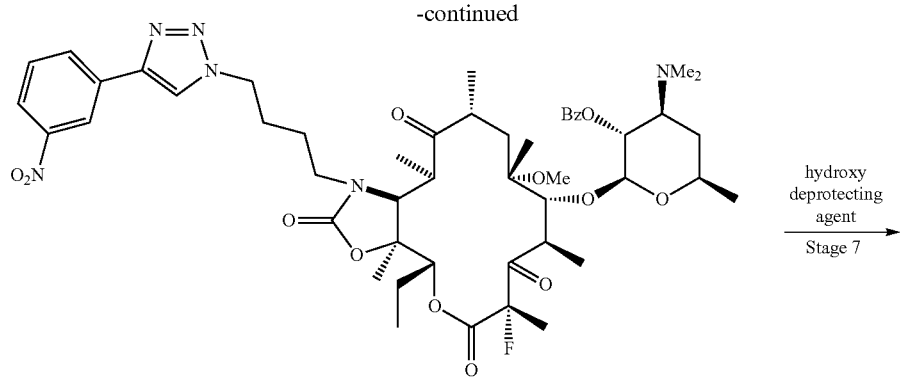

hydroxy deprotecting agent
Stage 7

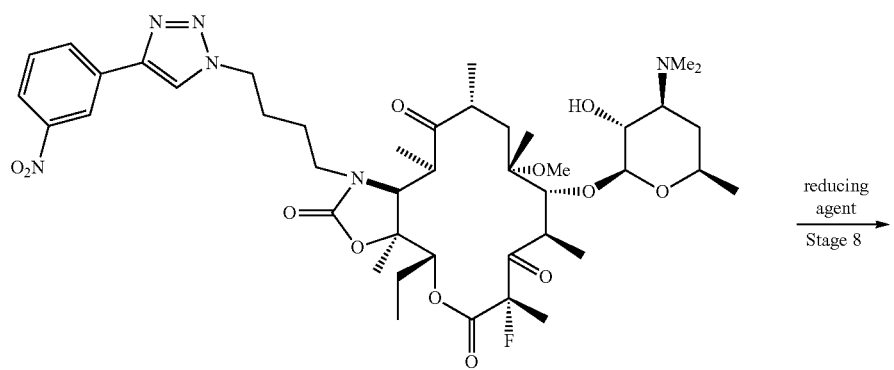

reducing agent
Stage 8

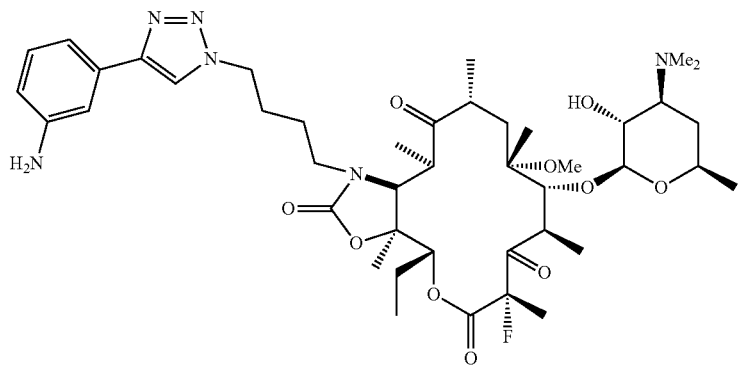

CEM-101

The processes and compounds described herein are further illustrated by the following examples. The following examples are intended to be illustrative and should not be construed or considered to be limiting in any manner.

EXAMPLES

Example. CEM-101 is prepared according to the following process.

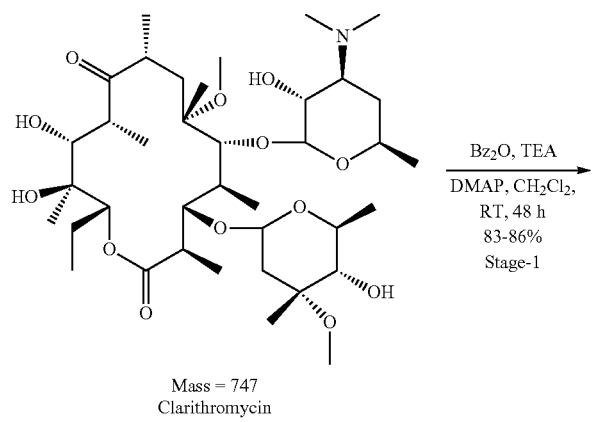
Mass = 747
Clarithromycin
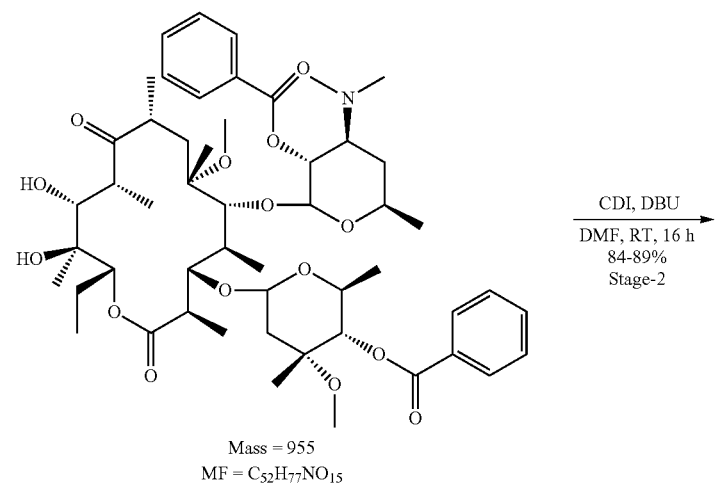
Mass = 955
MF = C$_{52}$H$_{77}$NO$_{15}$
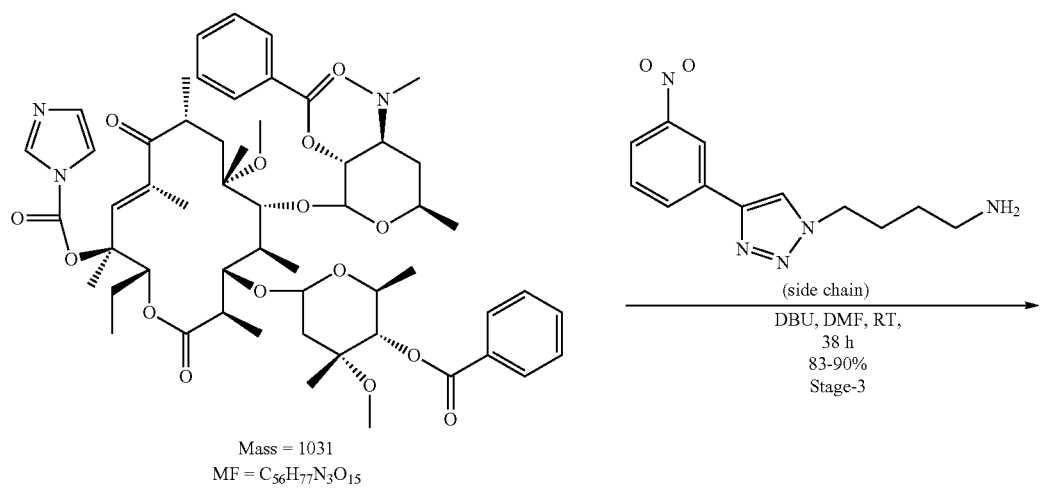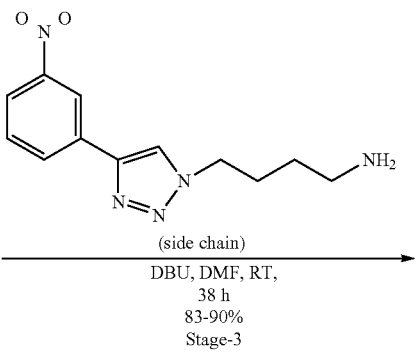
Mass = 1031
MF = C$_{56}$H$_{77}$N$_3$O$_{15}$
(side chain)
DBU, DMF, RT,
38 h
83-90%
Stage-3

-continued
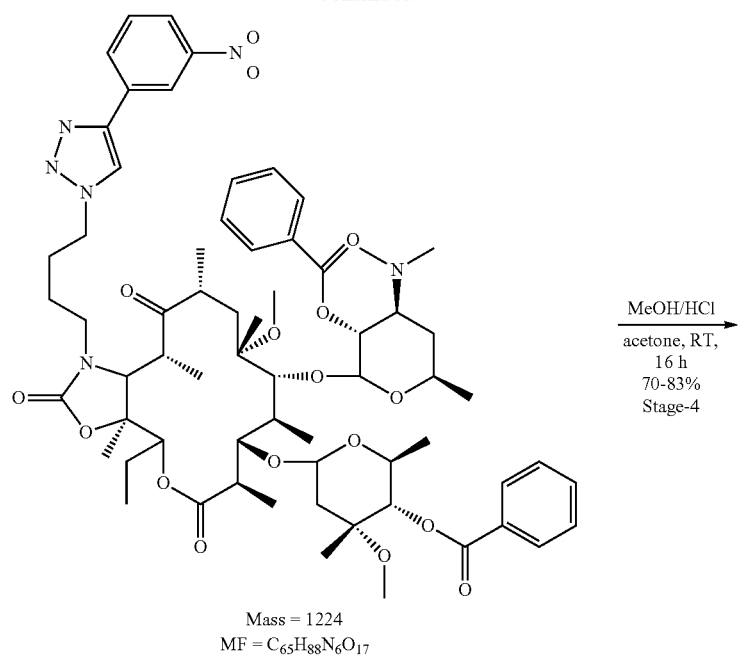
Mass = 1224
MF = C<sub>65</sub>H<sub>88</sub>N<sub>6</sub>O<sub>17</sub>
MeOH/HCl
acetone, RT,
16 h
70-83%
Stage-4
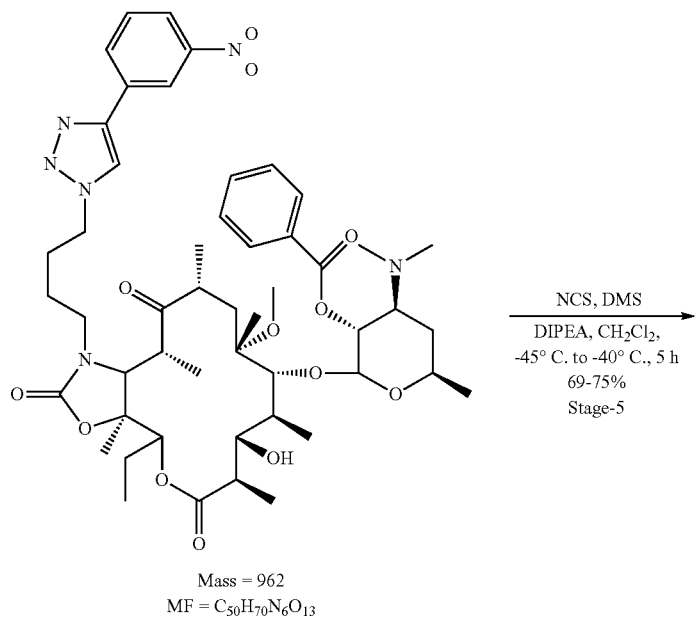
Mass = 962
MF = C<sub>50</sub>H<sub>70</sub>N<sub>6</sub>O<sub>13</sub>
NCS, DMS
DIPEA, CH₂Cl₂,
-45° C. to -40° C., 5 h
69-75%
Stage-5

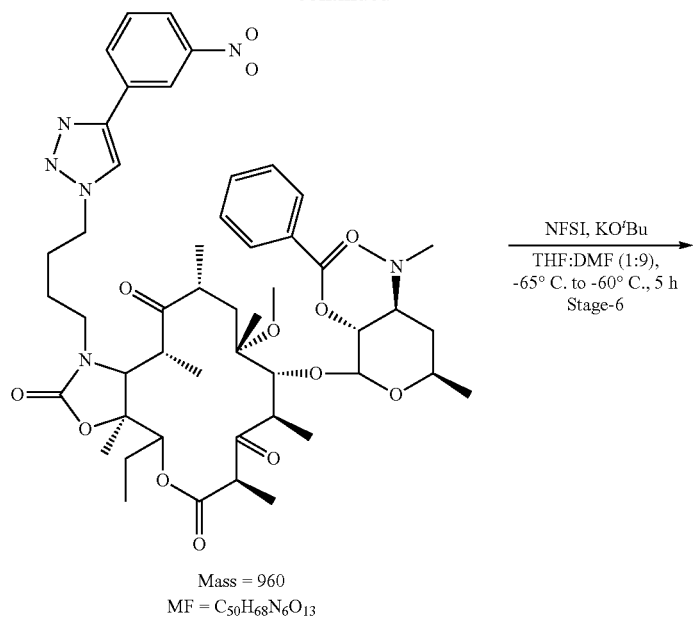
Mass = 960
MF = C₅₀H₆₈N₆O₁₃
NFSI, KO^tBu
THF:DMF (1:9),
-65° C. to -60° C., 5 h
Stage-6
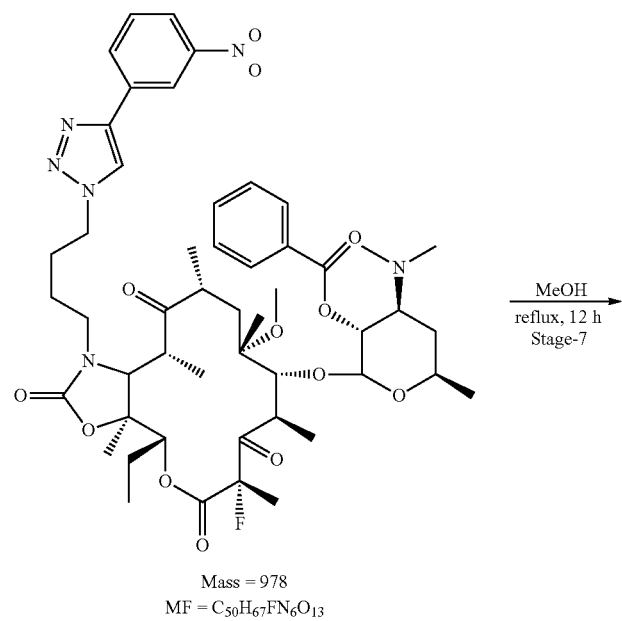
MeOH
reflux, 12 h
Stage-7
Mass = 978
MF = C₅₀H₆₇FN₆O₁₃

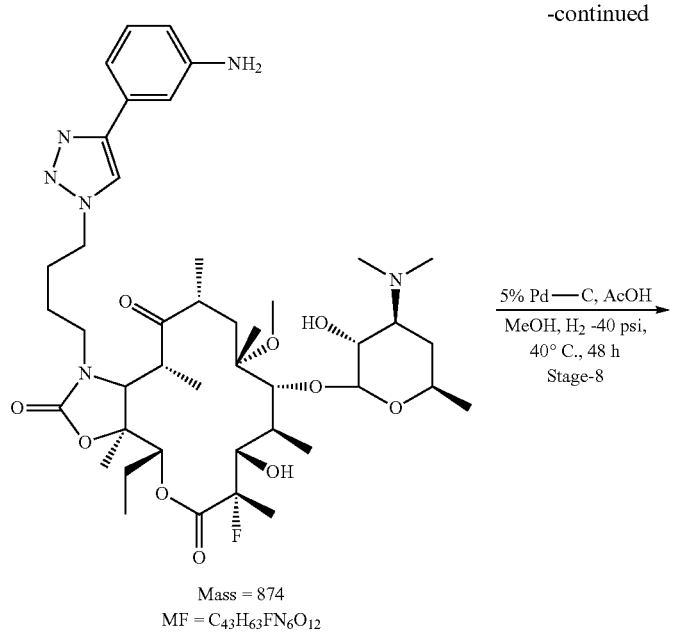

Mass = 874
MF = C43H63FN6O12

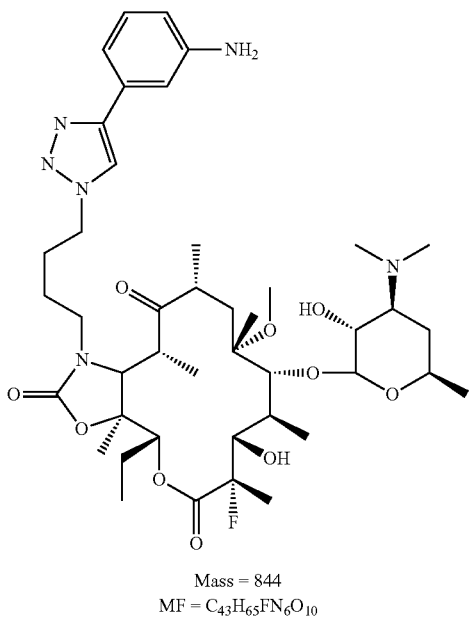

Mass = 844
MF = C43H65FN6O10

Example. Compounds of the Formula

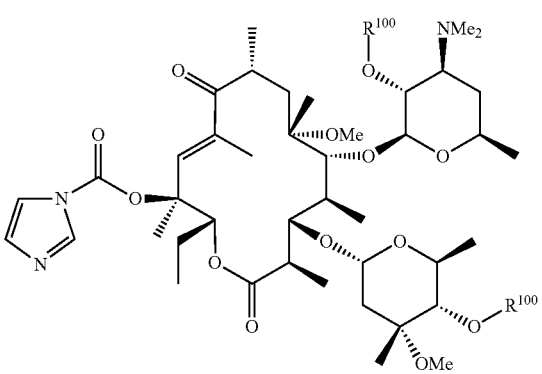

where $R^{100}$ is a hydroxy protecting group, such as an acyl group, including acetyl, benzoyl, and the like, are prepared using conventional processes, such as but not limited to processes described in PCT International Publication Nos. WO/2009/055557 and WO/2011/146829, the disclosures of which are incorporated herein by reference, in their entirety.

Example. Stage 1.

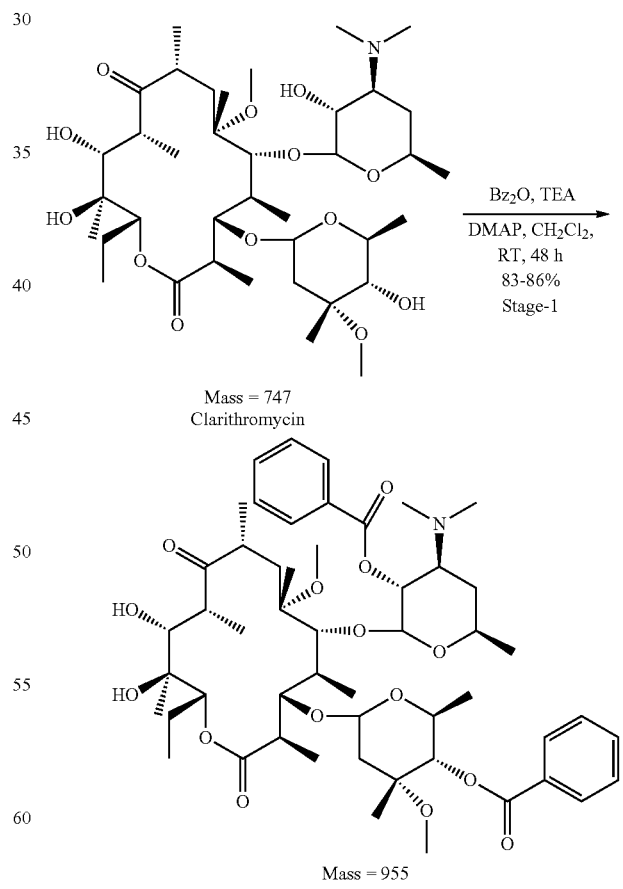

Mass = 747
Clarithromycin

Mass = 955
MF = C52H77NO15

Preparation of 2',4"-di-O-benzoyl-6-O-methylerythromycin A. 125 mL of ethyl acetate was added to 25 g clarithromycin A. 26.5 g benzoic anhydride, 5.7 g 4-dimethylamino pyridine and 6.7 g triethylamine were added to the reaction mixture at 25° C. to 35° C. The reaction mixture was stirred for about 70 hours at ambient temperature. After completion of the reaction, ethyl acetate was distilled out to obtain the title compound.

Example. Stage 2.

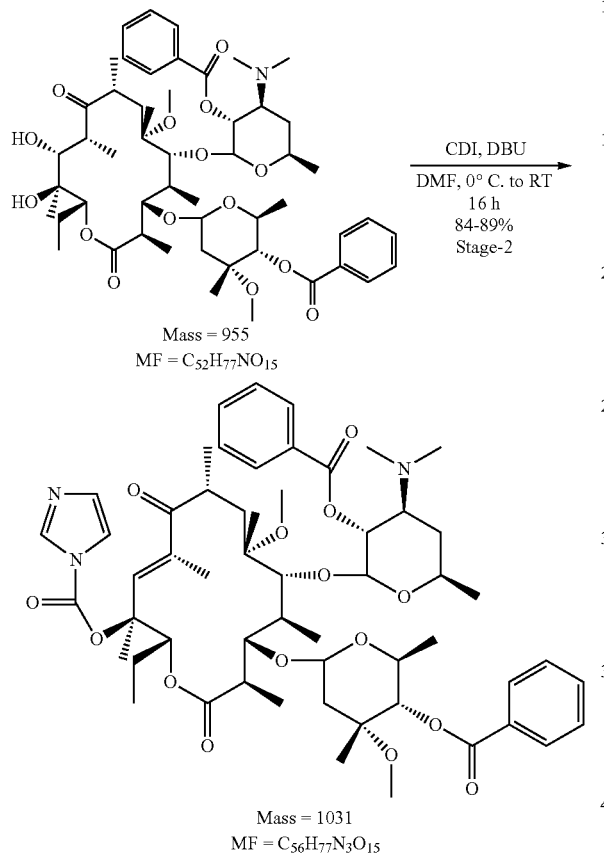

Preparation of 10,11-anhydro-2',4''-di-O-benzoyl-12-O-imidazolylcarbonyl-6-O-methylerythromycin A. Dimethylformamide (DMF, 100 mL) was added to 2',4''-di-O-benzoyl-6-O-methylerythromycin A at 25-35° C., then 1,8-diazabicyclo[5.4.0]undec-7-ene (DBU 6.4 g) was added to the reaction mixture and stirred at ambient temperature. 1,1'-Carbonyldiimidazole (CDI, 17 g) was added to the reaction and it was stirred until completion at ambient temperature. The title compound is isolated by addition of water, and collecting the resulting precipitate.

Example. Compounds of Formulae (A)

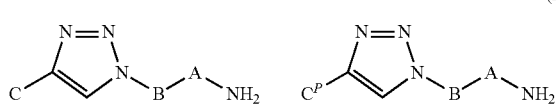

where A, B, C, and $C^P$ are as defined herein in each of the embodiments described herein, are prepared using conventional processes. Similarly, compounds of formula (A1)

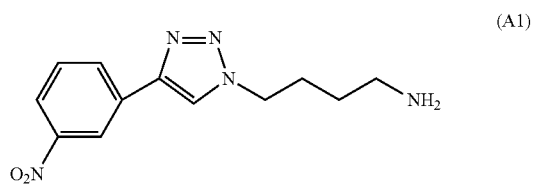 [SMILES: NCCCCn1cc(-c2cccc([N+](=O)[O-])c2)nn1]

are prepared using conventional processes. Similarly, compounds of formula (A2)

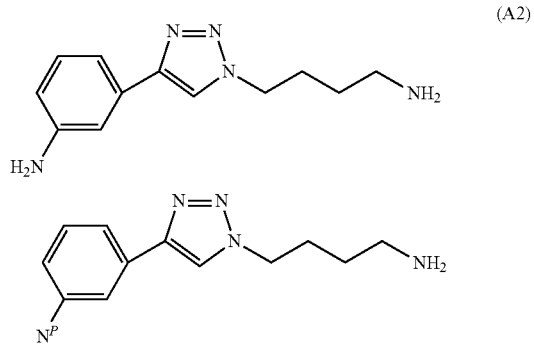

where $N^P$ is as defined herein in each of the embodiments described herein, are prepared using conventional processes. It is appreciated that the aminophenyl group of the compounds of formula (A2) may be protected prior to addition to Intermediate 3. Amino protected amide, carbamate, and urea derivatives are also prepared using conventional processes.

Example. Illustratively, the foregoing compounds may be prepared by the following processes, illustrated for compounds of formula (A1):

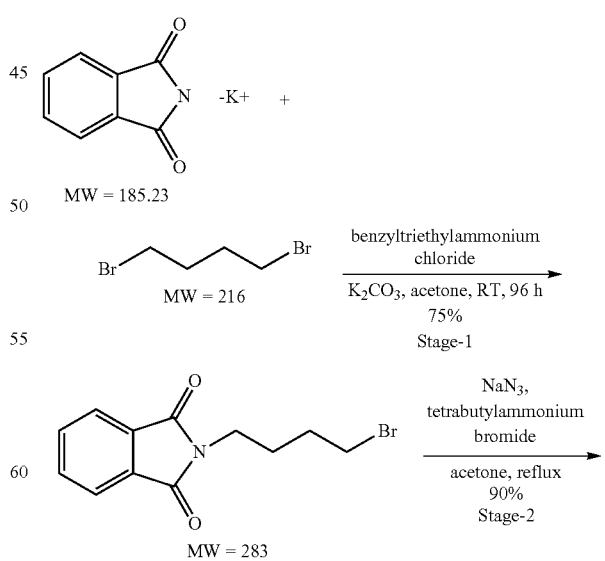

-continued

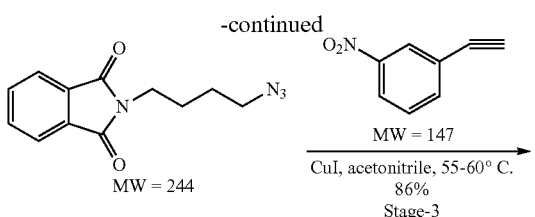

Stage-3: CuI, acetonitrile, 55-60° C., 86%

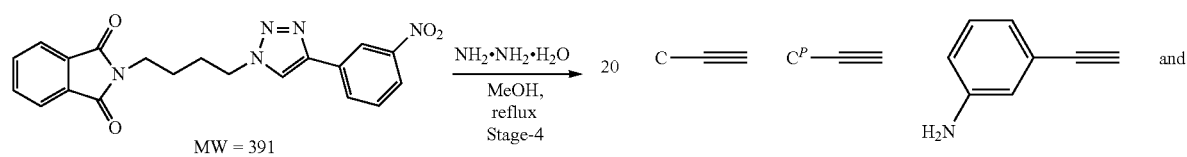

Stage-4: NH$_2$·NH$_2$·H$_2$O, MeOH, reflux

It is to be understood that the foregoing process may be used to prepare compounds of the formula (A) and/or (A1), including amino-protected derivatives thereof by the appropriate selection of starting materials, such as

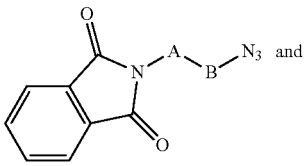

and

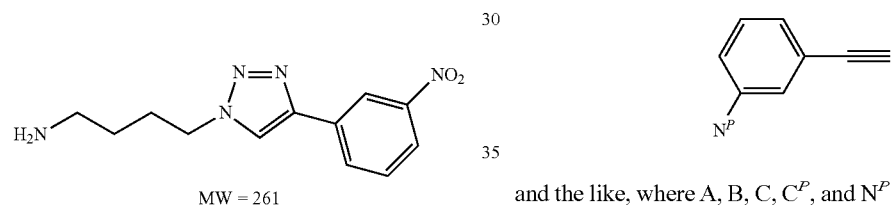

and and the like, where A, B, C, C$^P$, and N$^P$ are as defined herein in each of the embodiments described herein.

Example. Stage 3.

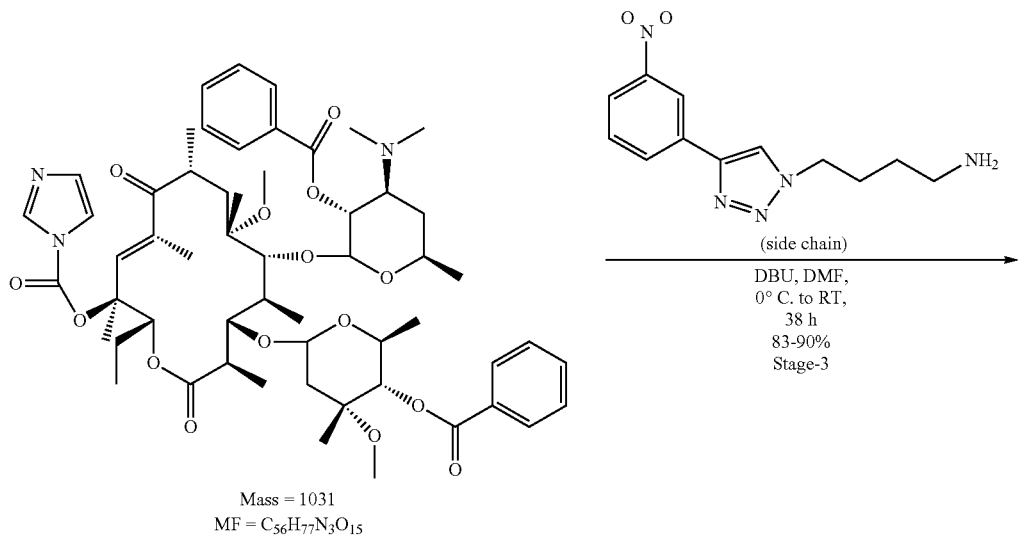

Stage-3: (side chain) DBU, DMF, 0° C. to RT, 38 h, 83-90%

Mass = 1031
MF = C$_{56}$H$_{77}$N$_3$O$_{15}$

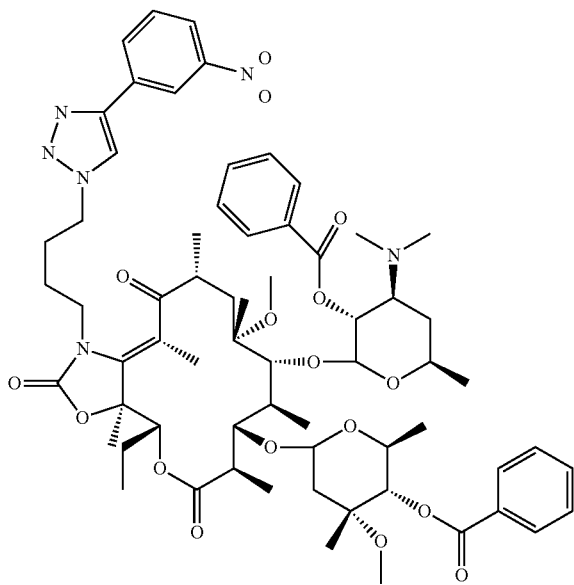

Mass = 1224
MF = C65H88N6O17

To a solution Stage-2 compound dissolved in 3000 mL of DMF (5.0 v, M/C<1.0%) at 0-5° C. was added drop wise DBU followed by side chain in portions. The reaction mixture was allowed to come to room temperature and stirred for 36 h. The HPLC recorded after 36 h showed <1% of un-reacted Stage-2 compound.

The reaction mixture was poured into ice cold water (6000 mL) and stirred for 2 h. The solid was filtered, washed with water (2500 mL) and suck dried for 2 h to obtain 650 g of crude product with 85% HPLC purity.

The crude product was added at room temperature to a bi-phasic solution of ethyl acetate (1500 mL) and 1 N aqueous HCl (1500 mL) and stirred for 1 h. The solid was filtered, washed with ethyl acetate (600 mL) and suck dried for 2 h. The solid was suspended again in ethyl acetate (1500 mL), stirred for 1 h at room temperature and filtered. The filter cake was dried in a vacuum oven at 40-45° C. till the moisture content was not more than 3%. The pure product was obtained as a white solid in 88% yield (620 g) and 98% purity.

Example. Stage 4.

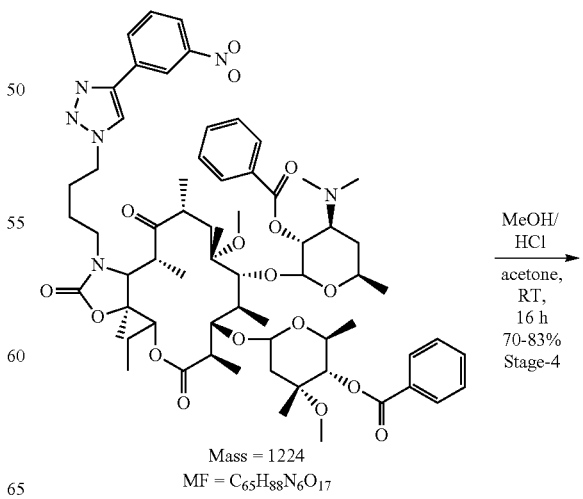

Mass = 1224
MF = C65H88N6O17

MeOH/
HCl
acetone,
RT,
16 h
70-83%
Stage-4

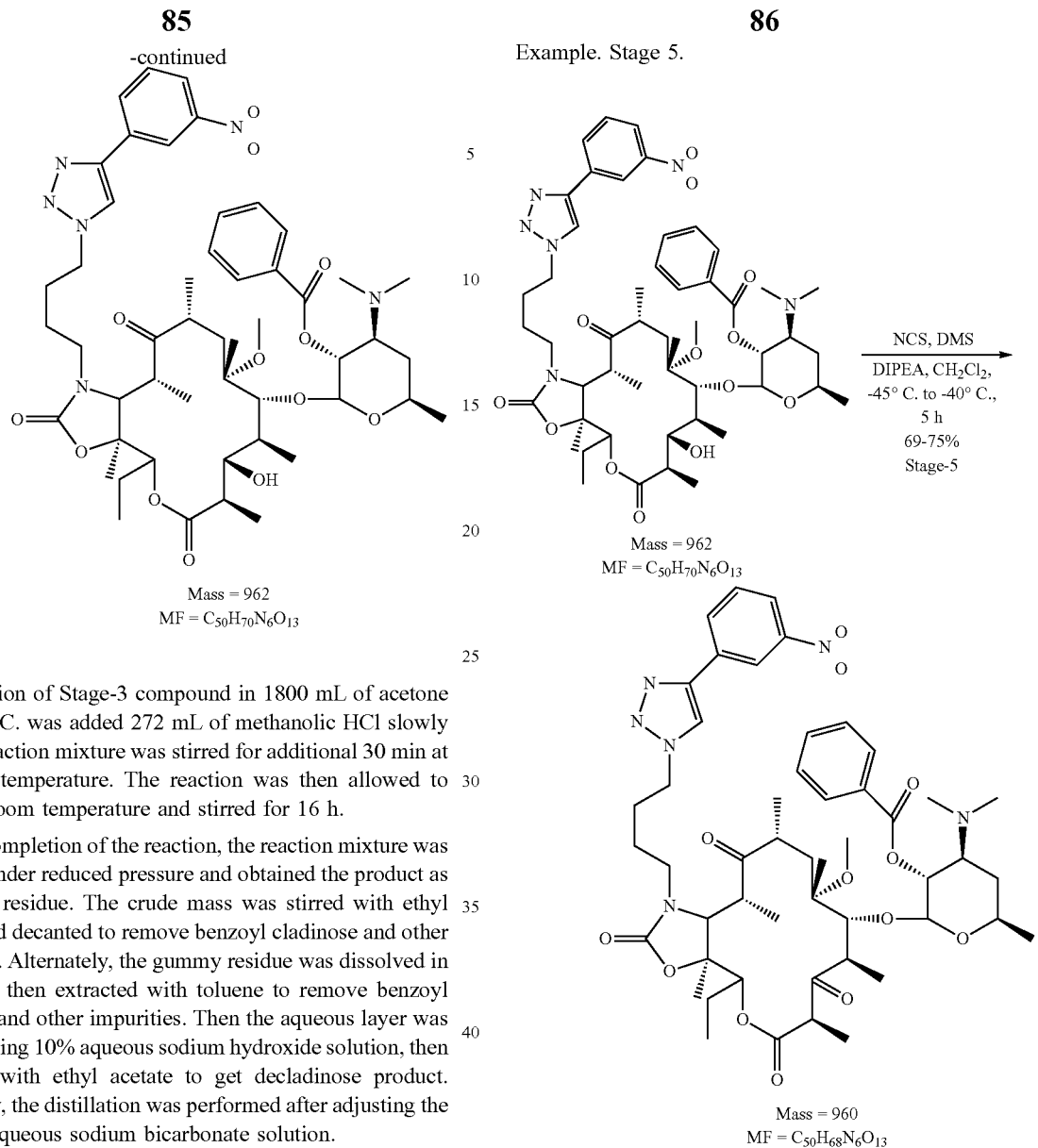

To a solution of Stage-3 compound in 1800 mL of acetone at 0 to 5° C. was added 272 mL of methanolic HCl slowly and the reaction mixture was stirred for additional 30 min at the same temperature. The reaction was then allowed to come to room temperature and stirred for 16 h.

After completion of the reaction, the reaction mixture was distilled under reduced pressure and obtained the product as a gummy residue. The crude mass was stirred with ethyl acetate and decanted to remove benzoyl cladinose and other impurities. Alternately, the gummy residue was dissolved in water and then extracted with toluene to remove benzoyl cladinose and other impurities. Then the aqueous layer was basified using 10% aqueous sodium hydroxide solution, then extracted with ethyl acetate to get decladinose product. Optionally, the distillation was performed after adjusting the pH with aqueous sodium bicarbonate solution.

The suspension was filtered and washed with acetone (200 mL). The pH of the filtrate was adjusted to 5 using saturated aqueous sodium bicarbonate solution and the solvents acetone and methanol were distilled under reduced pressure (below 40-45° C.). The residue was extracted with dichloromethane (3×200 mL) and the combined organic layer was dried over anhydrous sodium sulphate and distilled dichloromethane to obtain 130 g of crude product. The HPLC showed benzoyl cladinose and the desired product as major peaks (together showed 98% by area).

The crude product was stirred at room temperature in 5% ethyl acetate in hexanes (40 mL of ethyl acetate and 760 mL of hexanes) for 2 h and filtered. The filter cake was washed with 5% ethyl acetate in hexanes (10 mL of ethyl acetate and 190 mL of hexanes) and dried in a vacuum oven at 40-45° C. till the LOD was note more than 1% and M/C not more than 0.5%. The pure was obtained as a white solid in 86.6% yield (132 g) and 92.0% HPLC purity.

Example. Stage 5.

To a solution of N-chlorosuccinimide dissolved in 1600 mL of dichloromethane at −50° C. was added dimethyl sulfide over a period of 30 min, maintaining the temperature between −40 to −35° C. After stirring the reaction mixture for 60 min, a solution of Stage-4 compound in 1400 mL of dichloromethane was added over a period of 2 h maintaining the internal temperature between −40 to −35° C. The reaction mixture was stirred for further 90 min at −45° C. (HPLC showed <1% of the un-reacted starting material) and 177 mL of N-diisopropylethylamine was added cautiously over a period of 1 h maintaining the internal temperature between −45 to −40° C. The reaction mixture was warmed to 10° C. and stirred for 90 min.

To the reaction mixture 3000 mL of water was added and warmed the reaction mass to room temperature (25-30° C.). The organic layer was separated and washed successively with 1N aqueous HCl (2000 mL), water (2000 mL) followed by 10% aqueous sodium bicarbonate solution (2000 mL). The organic layer was then dried over anhydrous sodium sulphate and the solvent was distilled under reduced pressure to obtain 190 g of crude product having 85% HPLC purity.

The crude product was suspended in 400 mL of MTBE and heated at 55° C. for 2 h. The suspension was cooled to room temperature and stirred for 1 h. The solid was filtered and dried in a vacuum oven at 40-45° C. to obtain the pure product with LOD not more than 1.0% and M/C not more than 0.5%. The pure was obtained as a white solid in 89.1% yield (178 g) and 93.0% HPLC purity.

Example. Stage 6.

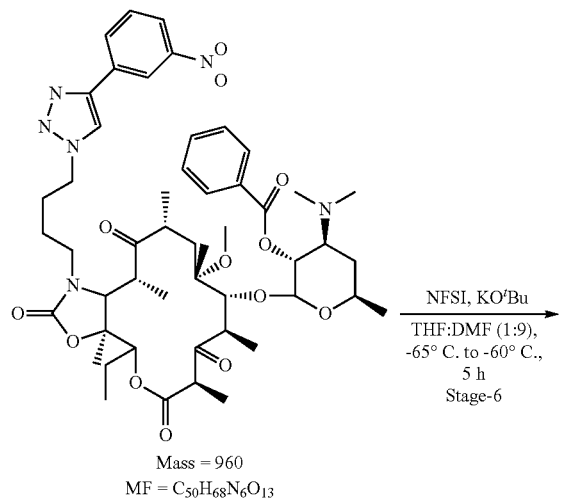

Mass = 960
MF = $C_{50}H_{68}N_6O_{13}$

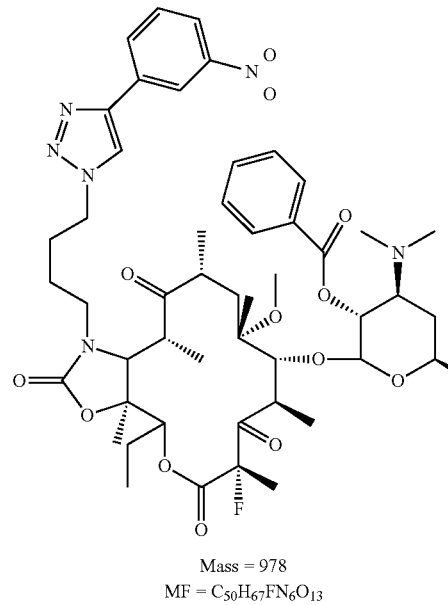

Mass = 978
MF = $C_{50}H_{67}FN_6O_{13}$

To a solution of Stage-5 compound dissolved in 9:1 mixture of DMF:THF (1350 mL of DMF and 150 mL of THF) at −65 to −60° C. was added K$^t$OBu in 10 equal portions and stirred the reaction mixture for 60 min at the same temperature. A solution of NFSI dissolved in 9:1 mixture of DMF:THF (900 mL of DMF and 100 mL of THF) was added to the reaction mixture over a period of 3-4 h maintaining the internal temperature between −65 to −60° C. The contents were stirred for further 60 min at the same temperature.

The reaction mixture was poured into 1000 mL of saturated aqueous NaHCO$_3$ solution maintained at 0° C. and stirred for 30 min. The precipitated solid was filtered, washed with 2×100 mL of water and dried in a vacuum oven at 45-50° C. till LOD was not more than 3.0% and M/C not more than 3%. The crude product was obtained a brown solid in 87.6% yield (90 g) and 80-90% HPLC purity. Further purification may be performed using column chromatography on fluorisil Example. Stage 7.

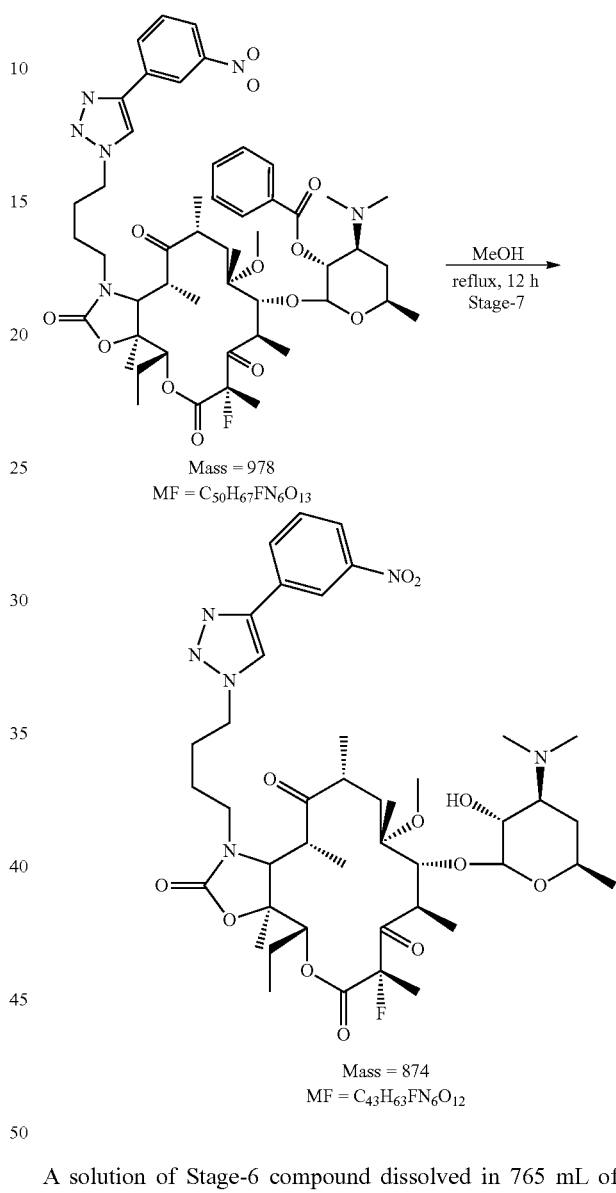

A solution of Stage-6 compound dissolved in 765 mL of methanol was heated at reflux temperature for 12 h. The HPLC after 12 h showed <1% of the starting material and at this stage charcoal was added and stirred for further 2 h at reflux temperature.

The suspension was filtered over a celite bed and the filtrate was concentrated under reduced pressure (at <45° C.) to obtain the crude product as brown gummy solid.

The crude product was stirred at room temperature in 5% MTBE in hexanes (14 mL of MTBE and 255 mL of hexanes) for 2 h. The solid was filtered and the purification was repeated two more times with 5% MTBE in hexanes (14 mL of MTBE and 255 mL of hexanes each time) to obtain 73 g of product (90% yield) as pale brown solid with 90.54% purity.

Example. Stage 8.

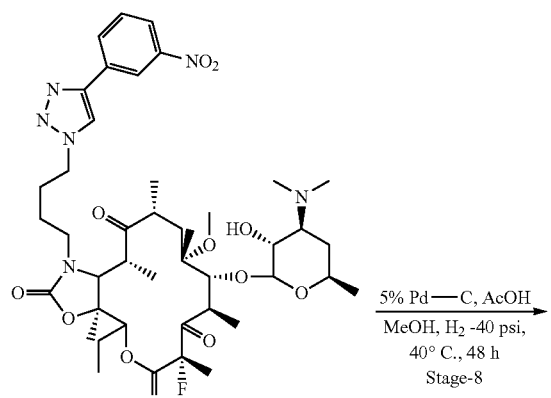

To a solution of Stage-7 compound dissolved in 450 mL of methanol was added 1.0 equiv of acetic acid followed by 3.3 w/w % of Pd—C. The suspension was stirred at 40° C. under 40 psi of hydrogen pressure for 6 h and HPLC showed 15% conversion of the starting material. The second lot of 6.6% w/w of Pd—C was added and continued to stir the reaction at 40° C. under 40 psi of hydrogen pressure for 24 h. At this stage HPLC showed 55% conversion of the starting material. The third lot of 3.3% Pd—C was added to the reaction mixture and after 12 h<1% of un-reacted starting material was observed.

The reaction mixture was cooled to room temperature and the suspension was filtered through a celite bed. The filter cake was washed with 200 mL of methanol and the combined filtrates were subjected to distillation under reduced pressure (below 45° C. temperature) to obtain gummy solid. The gummy solid was dissolved in 125 mL of dichloromethane and washed with 25 mL of aqueous ammonia solution. The organic layer was dried over sodium sulphate and dichloromethane was distilled to obtain crude product as pale brown solid (21 g) in 80% HPLC purity.

The crude product was suspended in 50 mL of IPA and stirred at 55-60° C. for 3 days. The suspension was allowed to cool to room temperature and filtered. The filter cake was washed with 25 mL of cold IPA and dried under vacuum at 40-45° C. to obtain 12.6 g (52% yield) of the product with 94% purity.

Example. CEM-101 is prepared according to the following process.

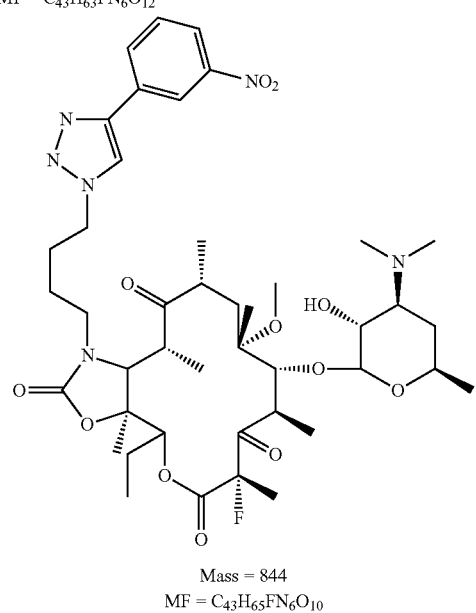

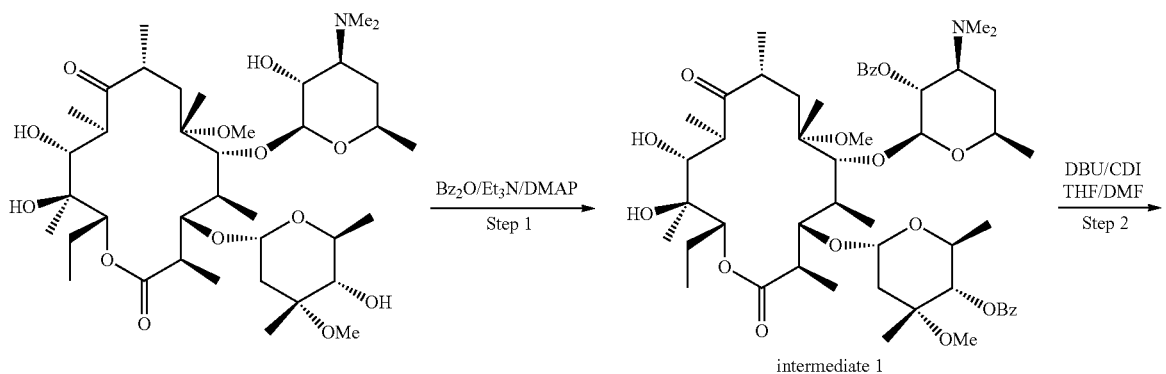

-continued
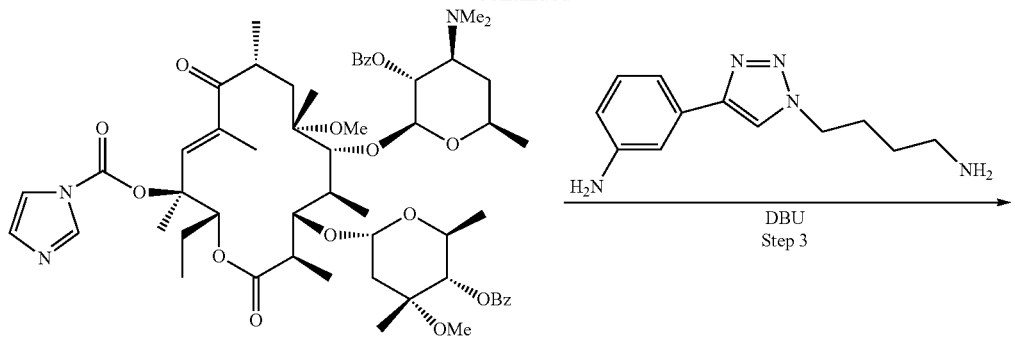
intermediate 2
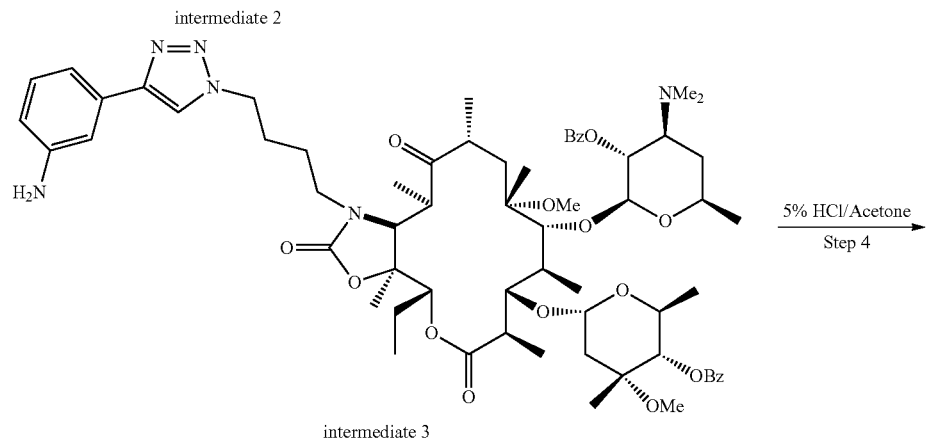
intermediate 3
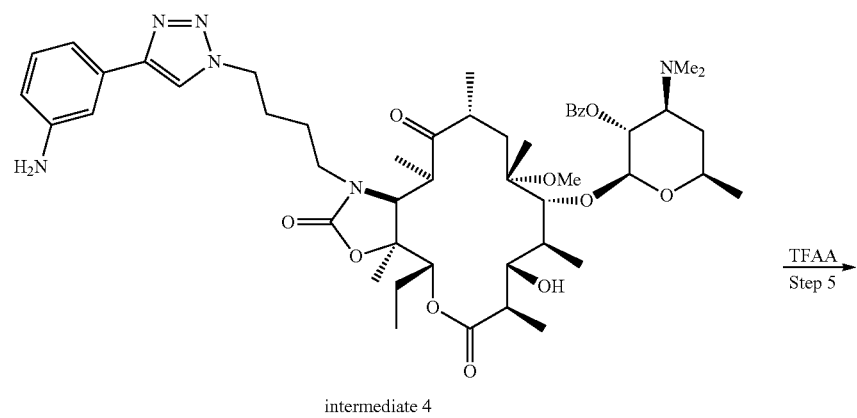
intermediate 4
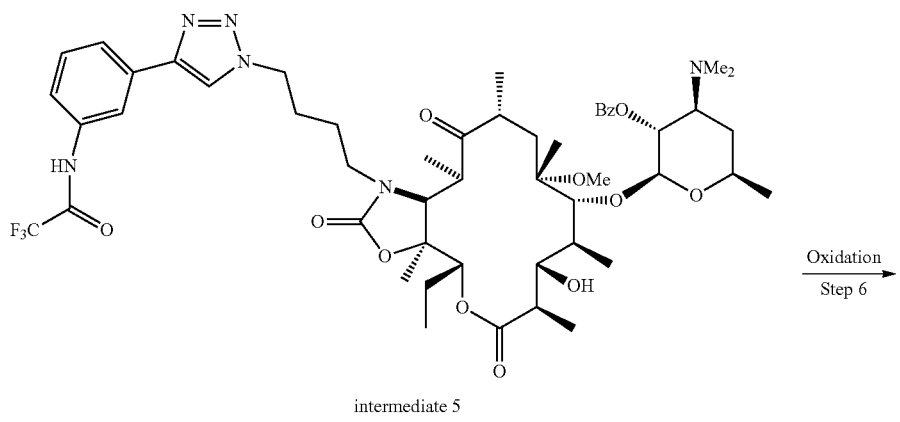
intermediate 5

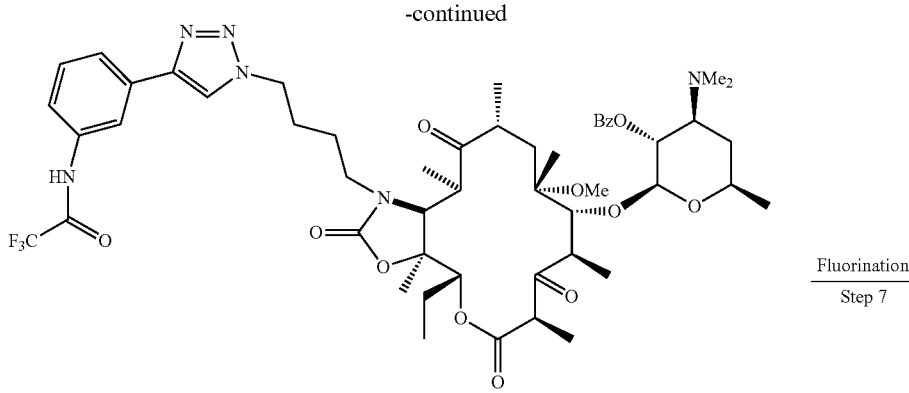

intermediate 6

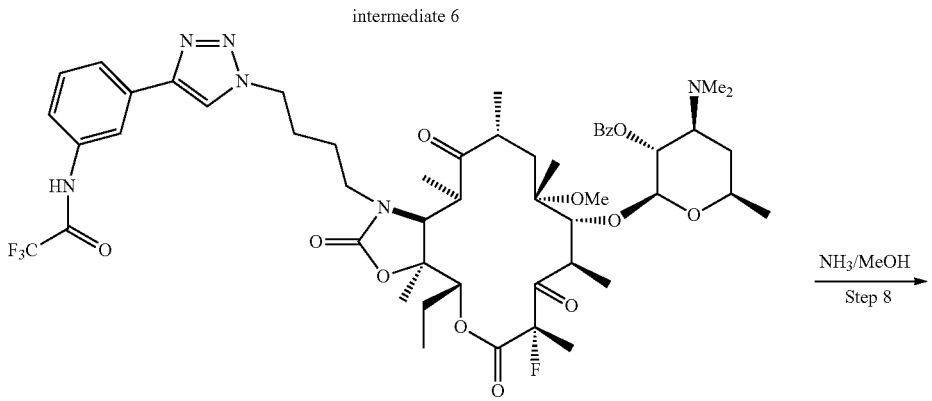

intermediate 7

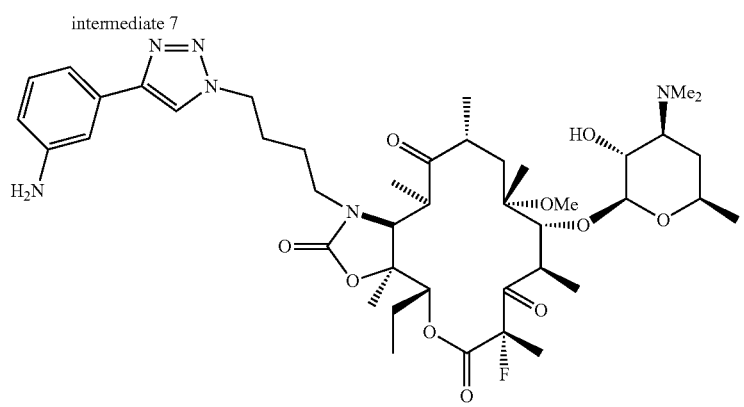

CEM-101

Example. Intermediate 4.

Intermediate 4 is prepared as described in PCT International Publication Nos. WO/2009/055557 and WO/2011/146829 from clarithromycin, and generally according to the process shown in Scheme 1. 62 g of Intermediate 1 was prepared in 80% yield from clarithromycin. 15 g of Intermediate 2 was prepared from Intermediate 1 in 93% yield. Cyclization of Intermediate 2 gave 6.6 g of intermediate 3 in 86% yield. Removal of cladinose from intermediate 3 Step 4 gave 4.4 g of Intermediate 4 in 85% yield. The product identity was confirmed by mass spectrometry and NMR.

Example. Intermediate 5.

Trifluoroacetic anhydride (113 mg, 0.54 mmol) was added dropwise to a solution of Intermediate 4 (500 mg, 0.54 mmol) in anhydrous DCM (9 mL) at 0° C. After the addition, the reaction mixture was stirred at 0° C. for 1 h. The reaction mixture was diluted with DCM, washed successively with dilute aqueous NaHCO₃ solution and brine, and dried over anhydrous MgSO₄. After filtration, the filtrate was concentrated to dryness to give 450 mg of crude Intermediate 5 as a light brown solid. Mass spectroscopy analysis of crude Intermediate 5 showed the desired product peak as the major component. The ¹H-NMR spectrum of crude Intermediate 5 showed peaks corresponding to the desired structure of the product. The ¹H-NMR spectrum also showed the presence of unreacted Intermediate 4. The material (~85% purity) was used without further purification.

Example. Intermediate 6.

To a solution of Intermediate 5 (100 mg, 0.097 mmol, ~85% purity) in anhydrous DCM (3 mL) was added Dess-Martin periodinane (50 mg, 0.116 mmol, 1.2 eq). The resulting reaction mixture was stirred at room temperature for 1.5 h. The reaction mixture was diluted with DCM, washed successively with dilute aqueous sodium thiosulfate solution and brine, and dried over anhyd MgSO$_4$. After filtration, the filtrate concentrated to dryness. The crude product was subjected to silica gel column chromatography (eluent: acetone/DCM, 20/80, v/v) to afford 55 mg of pure Intermediate 6 as a white solid in 72% yield. The $^1$H-NMR spectrum of Intermediate 6 confirmed the structure of the product and its good purity.

Example. Intermediate 7.

A solution of Intermediate 6 (82 mg, 0.08 mmol) in DMF (1 mL) was cooled to −30° C. DBU (14 mg, 0.088 mmol) was added, and the resulting mixture was stirred at −30° C. for 20 min. To the reaction mixture stirring at −30° C. was added dropwise a solution of NSFI (25 mg, 0.08 mmol) in DMF (1 mL). After the addition, the reaction mixture was stirred at −30° C. for 20 min. The reaction mixture was quenched with dilute aqueous solution of NaHCO$_3$ and extracted with DCM. The combined DCM extract was washed with brine, and dried over anhyd MgSO$_4$. After filtration, the filtrate was concentrated to dryness. The crude product was subjected to silica gel column chromatography (eluent: acetone/DCM, 20/80, v/v) to afford 61 mg of pure Intermediate 7 as a white solid in 86% yield. The $^1$H-NMR spectrum of Intermediate 7 confirmed the desired structure of the product and its good purity.

Example. CEM-101.

A solution of Intermediate 7 (60 mg) in methanol (1 mL) containing 0.3 mL of NH$_4$OH was stirred at room temperature overnight. Mass spectroscopy analysis of an aliquot of the reaction mixture showed a peak with a Mw corresponding to CEM-101 as the major component along with unreacted Intermediate 7. The reaction mixture was diluted with DCM, washed successively with water and brine, and dried over anhyd MgSO$_4$. After filtration, the filtrate was concentrated to dryness. The crude product was dissolved in methanol (10 mL) and heated at reflux for one hour. The reaction mixture was concentrated to a small volume and the residue was subjected to silica gel column chromatography (eluent: DCM/MeOH/NH$_4$OH, 95/5/0.5, by volume) to afford 40 mg of CEM-101. The $^1$H-NMR spectrum confirmed the desired structure of the product.

Example. Synthesis of Intermediate 3a.

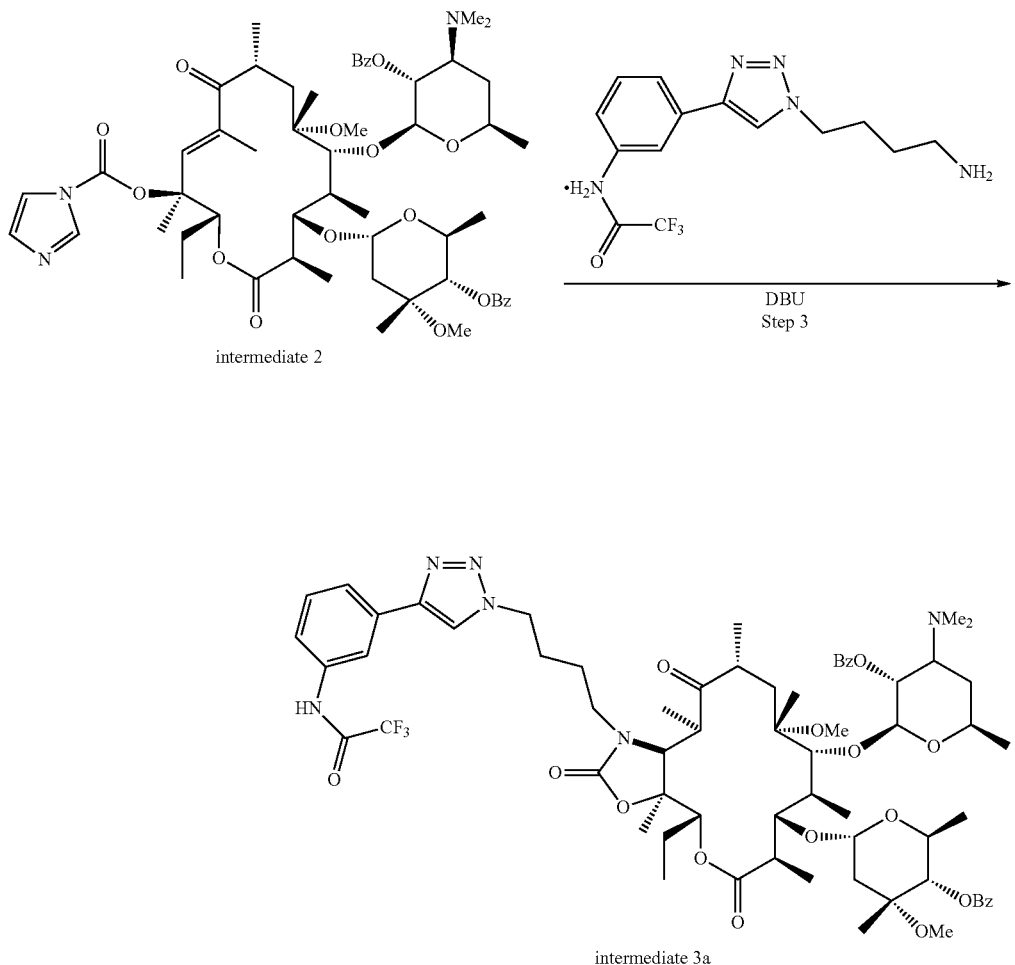

intermediate 2 intermediate 3a

A mixture of intermediate 2 (1.0 g), protected side chain-HCl salt (1.3 eq.), DBU (2.5 eq.), and DMF was heated at 40-70° C. with stirring under nitrogen. Reaction progress was monitored by TLC, HPLC, and MS. When complete, the mixture was partitioned between DCM and brine, washed with water, dried over anhydrous MgSO$_4$, filtered and evaporated. The residue was purified by HPLC to give ≥90% yield of the title compound. $^1$H NMR spectra and mass spectra (MW 1292) were consistent with the title compound.

Example. Synthesis of Intermediate 3a

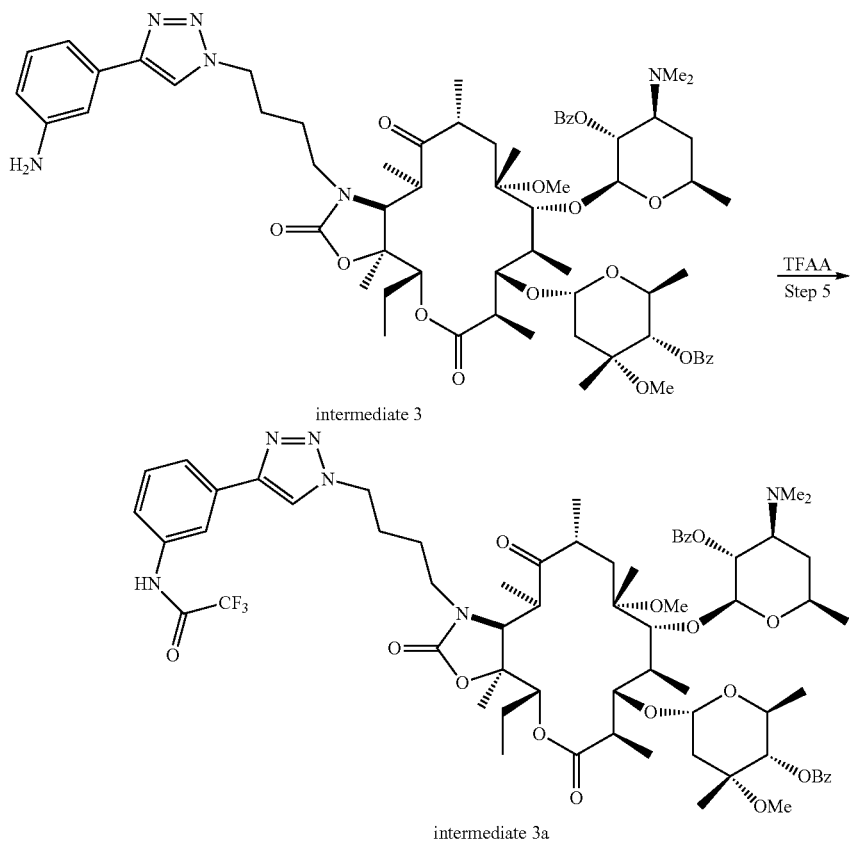

intermediate 3a

A solution of Intermediate 3 (650 mg, 0.544 mmol) in anhydrous DCM (10 mL) was cooled to 5° C. with an ice-bath. To this was added trifluoroacetic anhydride (172 mg, 0.82 mmol, 1.5 equivalent), and the resulting reaction mixture was stirred for 10 min at 5° C., before gradual warming to ambient temperature over 1.5 hr. The reaction was quenched with ice cold diluted aqueous $NaHCO_3$ and extracted with DCM. The combined DCM extract was washed with brine and dried over anhydrous $MgSO_4$. The drying agent was removed by filtration, and the filtrate was concentrated to dryness. The crude product was purified through silica gel column chromatography (eluent: DCM/MeOH/NH4OH=95/5/0.5, by volume) to give 540 mg of product in 77% yield. Both the $^1$H-NMR spectrum and mass spectrum of the product showed peaks conforming to the desired structure of Intermediate 3a.

Example. Synthesis of Intermediate 5

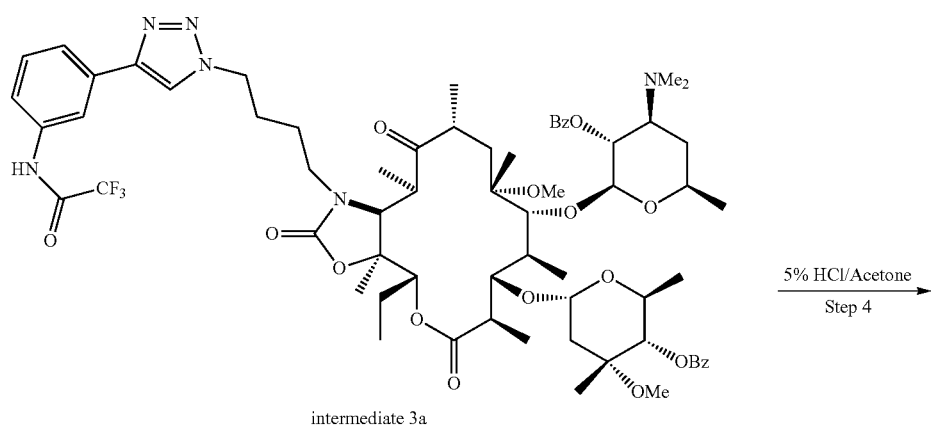

intermediate 3a

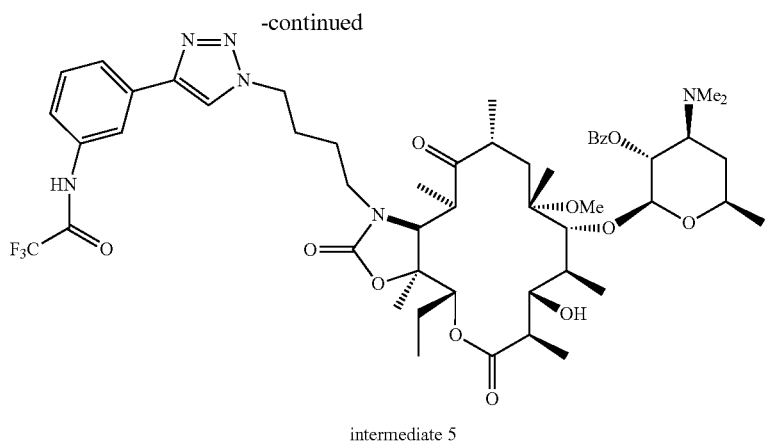

intermediate 5

To a solution of Intermediate 3a (150 mg, 0.116 mmol) in acetone (3 mL) was added DBU (35 mg, 0.233 mmol, 2.0 equivalent), followed by conc. HCl (300 µL). The resulting reaction mixture was stirred at room temperature for 5 hrs. Mass analysis of an aliquot of the reaction mixture showed complete reaction with clean reaction profile. The reaction mixture was poured into a mixture of DCM and ice water. The mixture was made basic by the addition of dilute NH$_4$OH and extracted with DCM. The combined DCM extract was washed with brine, dried over anhydrous MgSO$_4$. The drying agent was removed by filtration, and the filtrate was concentrated to dryness. The crude product was purified through silica gel column chromatography (eluent: DCM/MeOH/NH4OH=95/5/0.5, by volume) to give 103 mg of Intermediate 5 in 86% of yield. The $^1$H-NMR spectrum and mass spectrum of the product showed peaks corresponding to those expected for the desired structure of intermediate 5 with good purity.

Example. Synthesis of Intermediate 6a

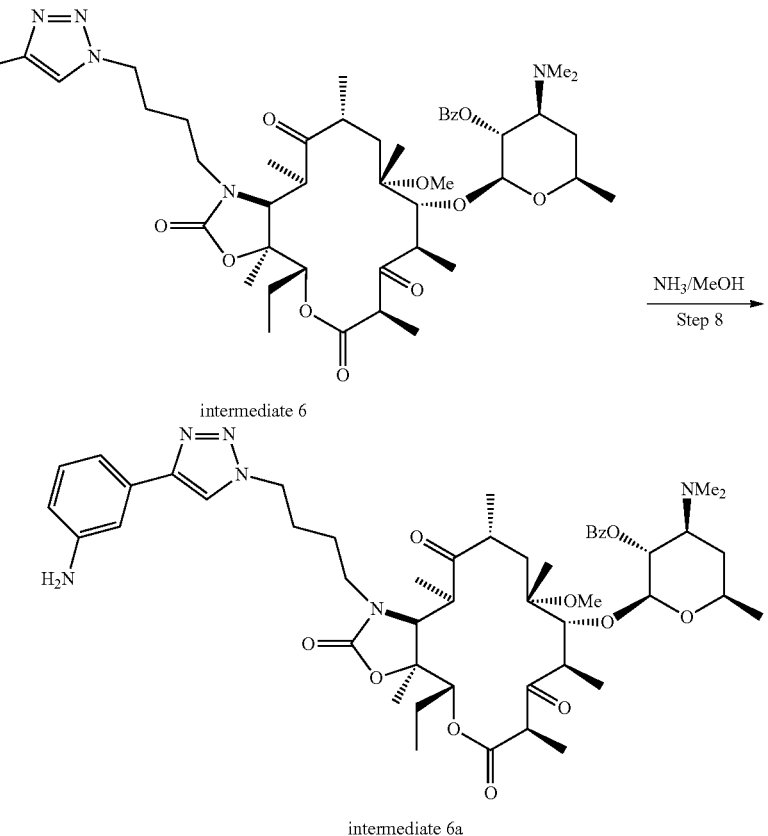

To a solution of Intermediate 6, (1.0 mmol) in methanol (10 mL) is added ammonium hydroxide solution (NH$_4$OH, 30 mmol). The resulting clear solution is stirred at ambient temperature overnight to give a turbid reaction mixture. The reaction mixture is concentrated to dryness, dissolved in DCM, washed successively with diluted aqueous NaHCO$_3$ solution and brine, and then dried over anhydrous. MgSO$_4$. After filtration to remove the drying agent, the filtrate is concentrated to dryness to afford 0.8 mmol of Intermediate 6a (90% yield). The 1H-NMR spectrum and mass spectrum are consistent with the title compound.

What is claimed is:

1. A process for preparing a compound of formula (I)

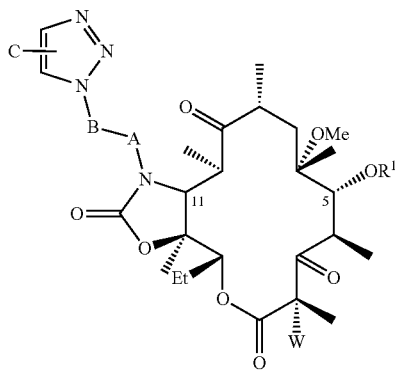

(I)

or a pharmaceutically acceptable salt thereof; wherein

R$^1$ is a desosamine or a desosamine derivative;

A is —CH$_2$—, —C(O)—, —C(O)O—, —C(O)NH—, —S(O)$_2$—, —S(O)$_2$NH—, or —C(O)NHS(O)$_2$—;

B is saturated C$_0$-C$_{10}$; or B is unsaturated C$_2$-C$_{10}$; or -A-B- taken together is alkylene, alkenylene, cycloalkylene, or arylene;

C represents 2 substituents independently selected in each instance from the group consisting of hydrogen, halogen, hydroxy, acyl, acyloxy, sulfonyl, ureyl, and carbamoyl, and alkyl, alkoxy, heteroalkyl, aryl, heteroaryl, arylalkyl, and heteroarylalkyl, each of which is optionally substituted; and W is hydrogen, F, Cl, Br, I, or OH;

the process comprising (A) contacting a compound of formula

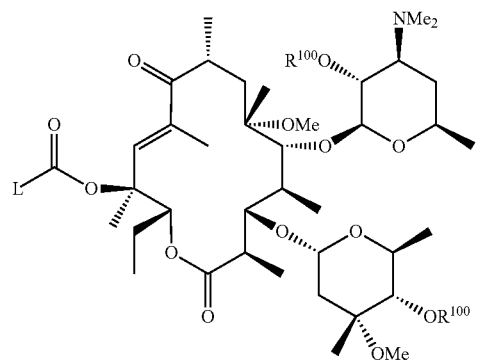

or a salt thereof, where R$^{100}$ is a hydroxyl protecting group, and L is a leaving group, with a compound of formula

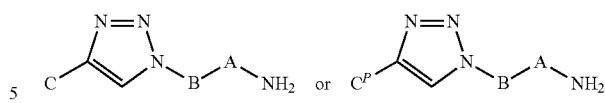

or a salt thereof, where C is as defined herein, and C$^P$ is a protected form of C, and a base, to prepare a compound of formula

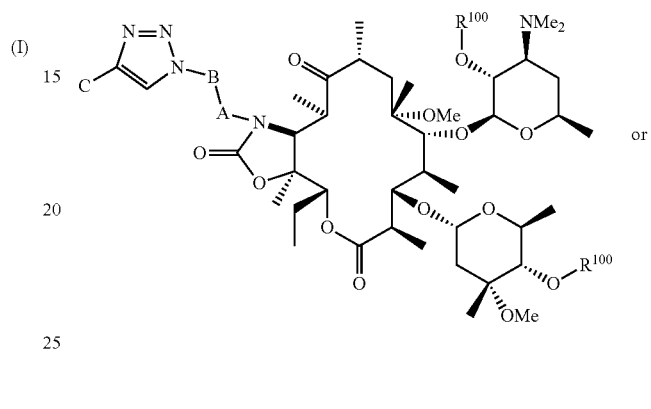

or a salt thereof; or (C) contacting a compound of formula

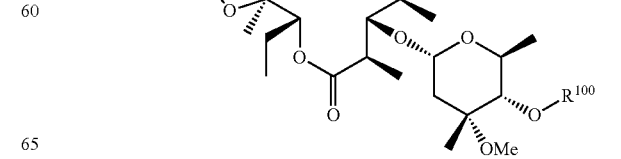

103
-continued
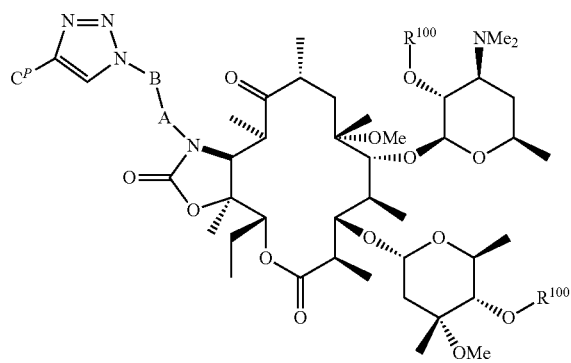
or a salt thereof, with an acid to prepare a compound of formula
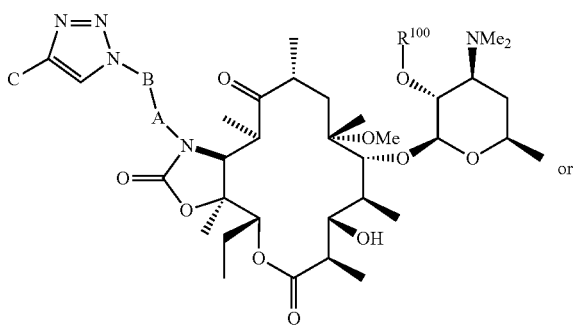
or a salt thereof; or
(E) contacting a compound of formula
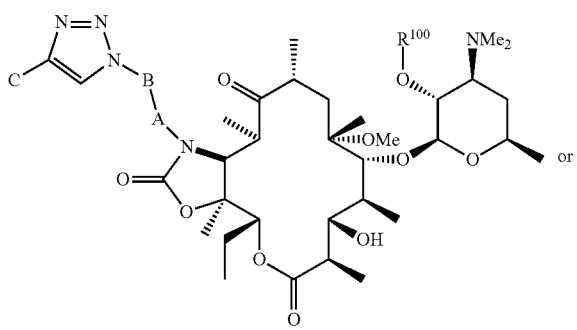
or
104
-continued
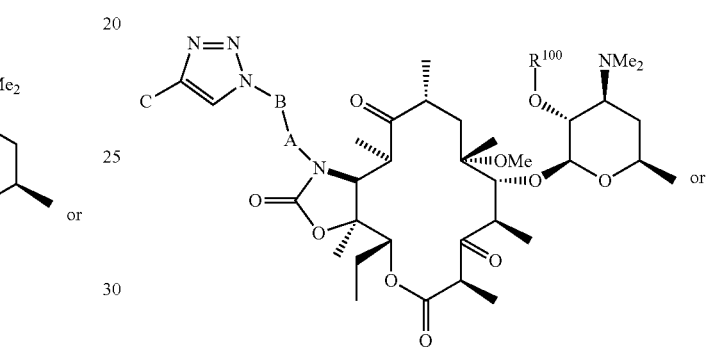
or a salt thereof, with an oxidizing agent to prepare a compound of formula
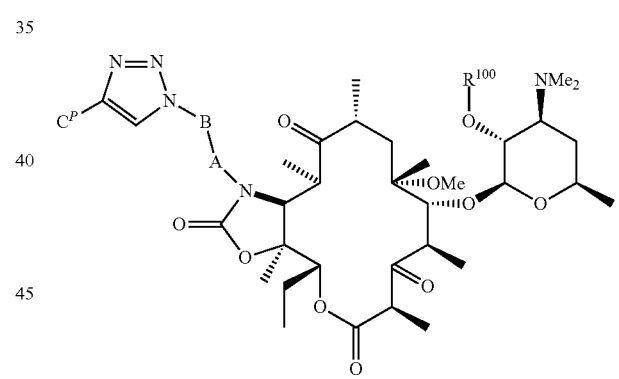
or a salt thereof; or
(F) contacting a compound of formula
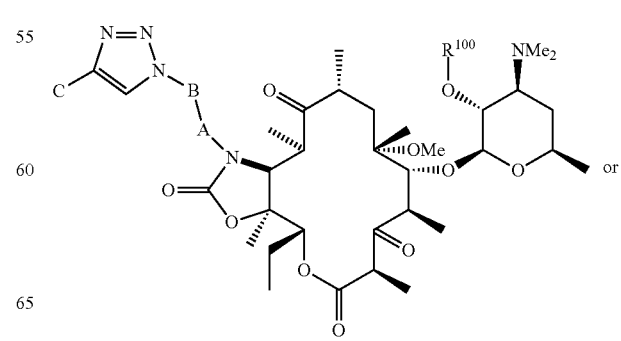
or -continued

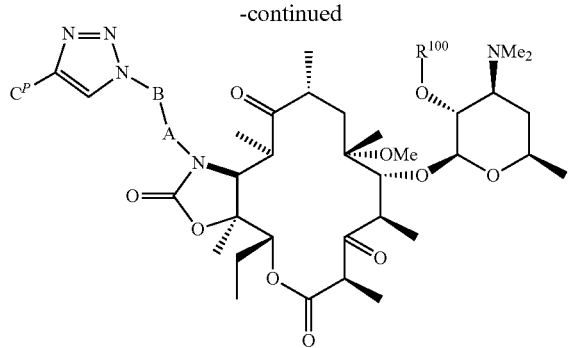

or a salt thereof, with a hydroxylating or halogenating agent to prepare a compound of formula

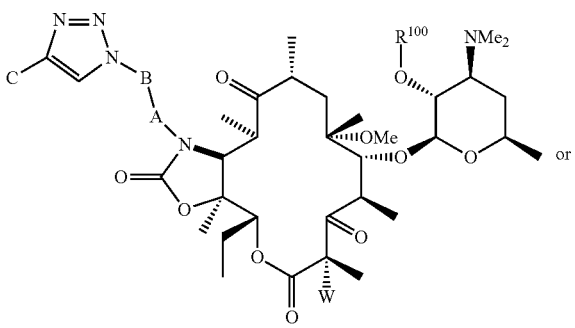

or

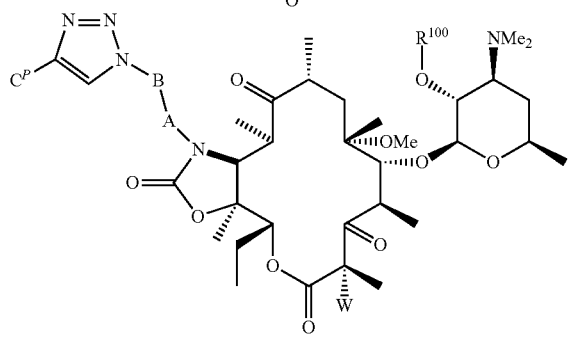

or a salt thereof, wherein W is F, Cl, Br, I, or OH; any combination of the foregoing.

2. The process of claim 1 comprising
(a) contacting a compound of formula

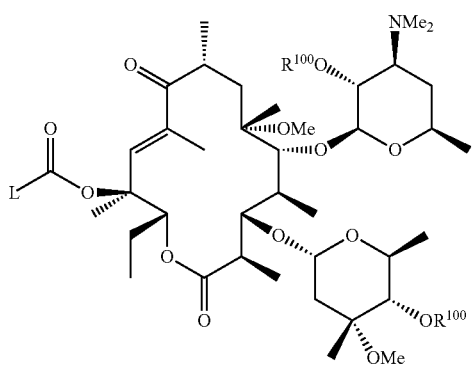

or a salt thereof, where $R^{100}$ is a hydroxyl protecting group, and L is a leaving group, with a compound of formula

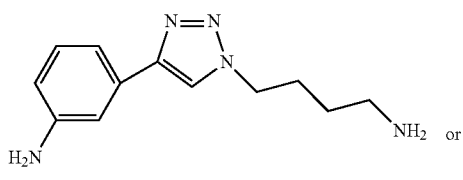

or

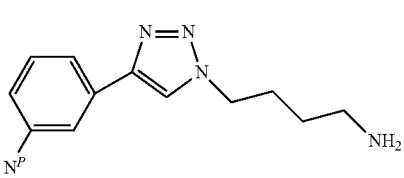

or a salt thereof, where $N^P$ is a protected amine, and a base; to prepare a compound of formula

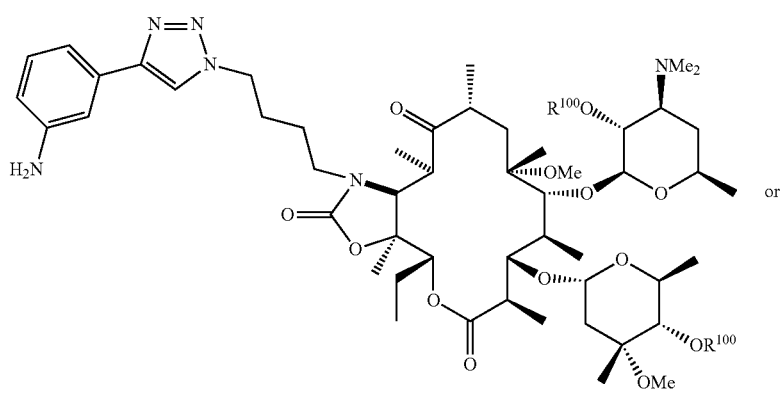

or

-continued
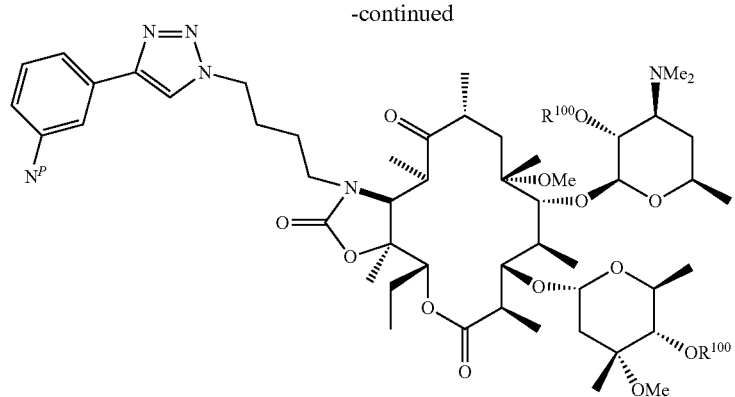
or a salt thereof; or
(c) contacting a compound of formula
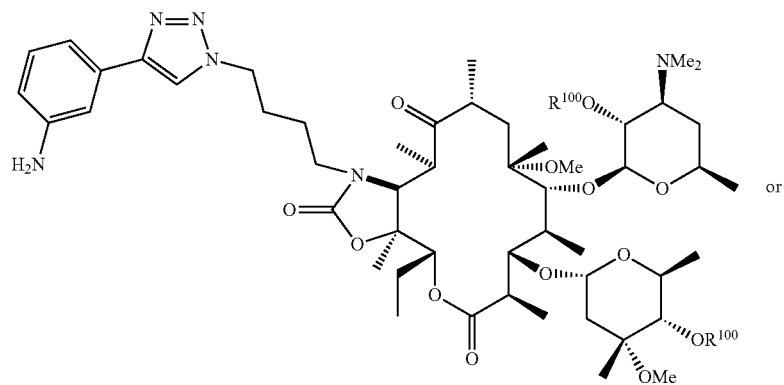
or
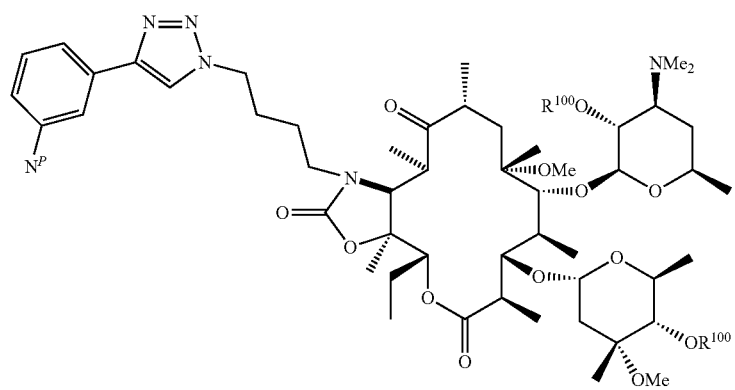

or a salt thereof, with an acid to prepare a compound of formula
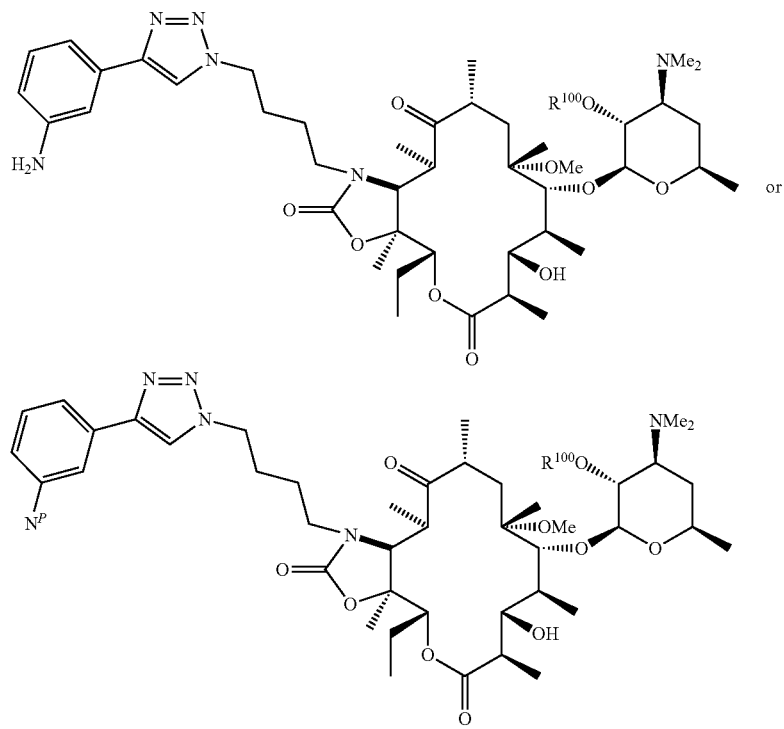
or a salt thereof; or
(e) contacting a compound of formula
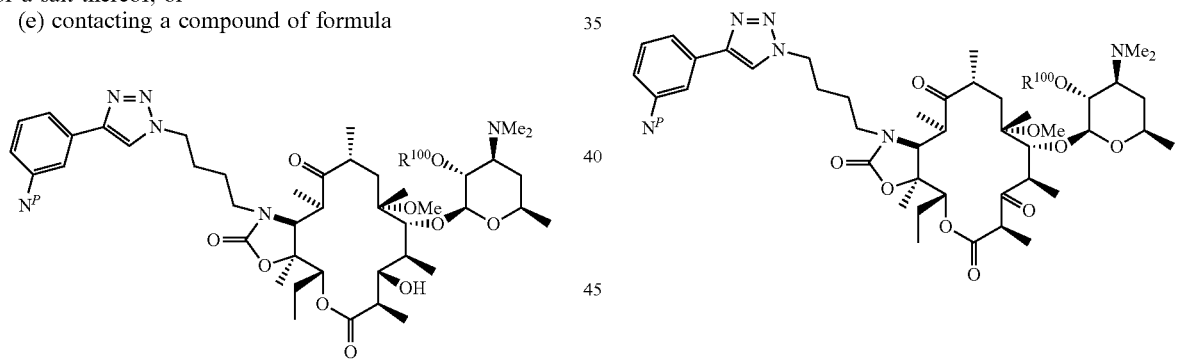
or a salt thereof, with an oxidizing agent to prepare a compound of formula
or a salt thereof; or
(g) contacting a compound of formula
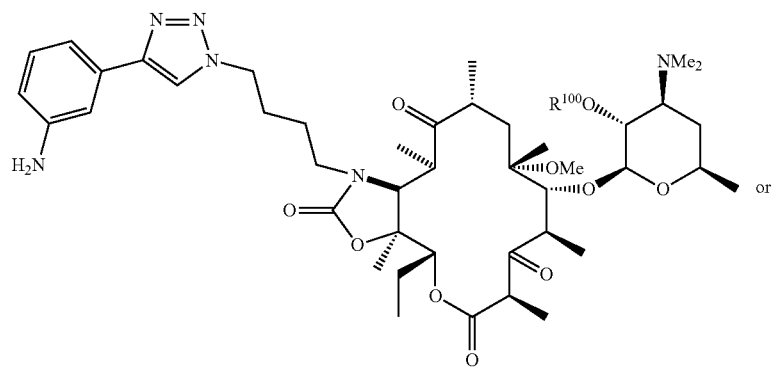

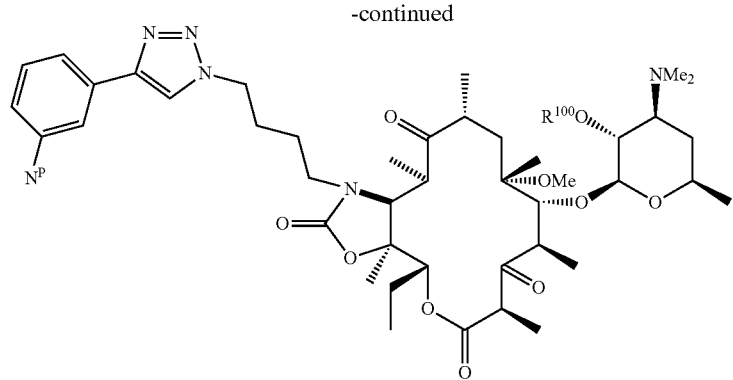
or a salt thereof, with a fluorinating agent to prepare a compound of formula
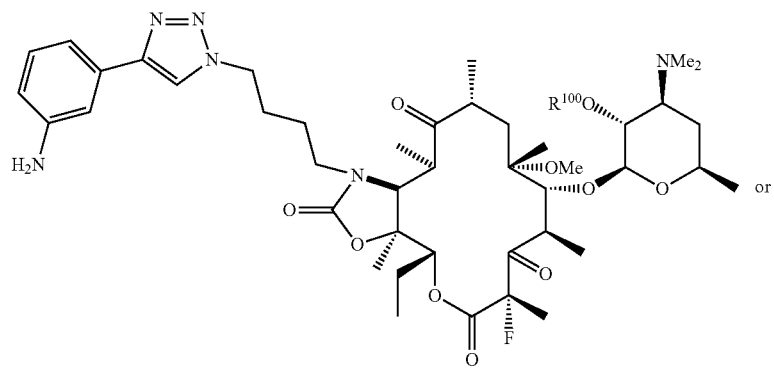
or a salt thereof; or
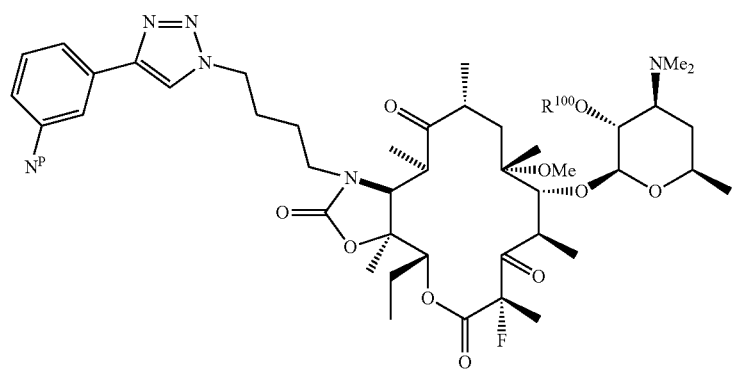
or a salt thereof; or
any combination of the foregoing.

3. The process of claim 2 wherein $N^P$ is $NHC(O)CF_3$.

4. The process of claim 1 comprising (a') contacting a compound of formula

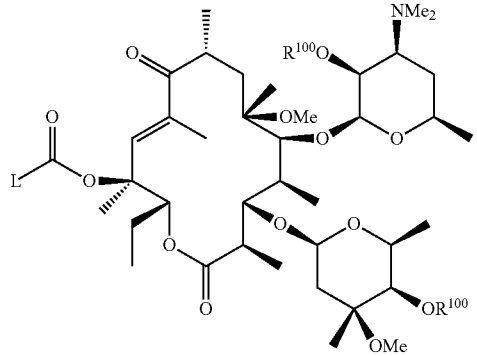

or a salt thereof, where $R^{100}$ is a hydroxyl protecting group, and L is a leaving group, with a compound of formula

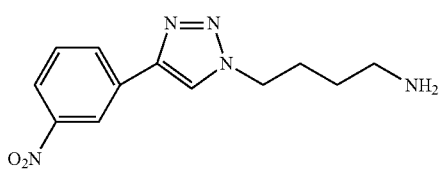

or a salt thereof, and a base; to prepare a compound of formula

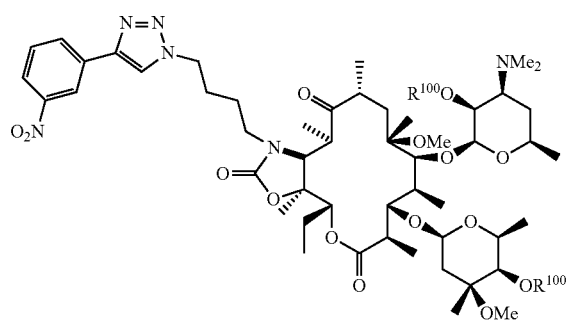

or a salt thereof; or (b') contacting a compound of formula

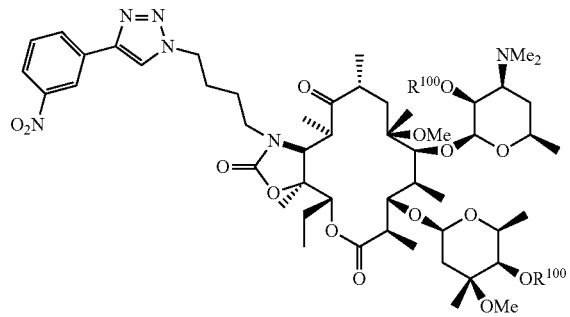

or a salt thereof, with an acid to prepare a compound of formula

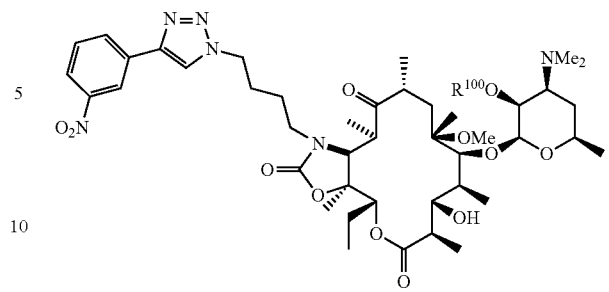

or a salt thereof; or (c') contacting a compound of formula

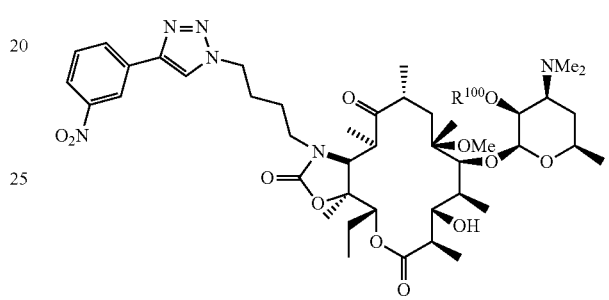

or a salt thereof, with an oxidizing agent to prepare a compound of formula

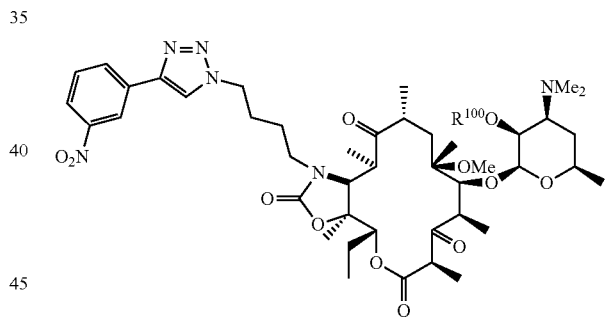

or a salt thereof; or (d') contacting a compound of formula

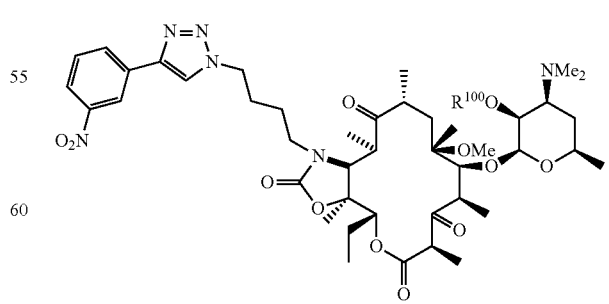

or a salt thereof, with a fluorinating agent to prepare a compound of formula

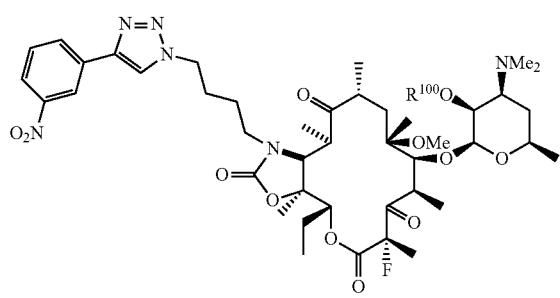

or a salt thereof; or any combination of the foregoing.

5. The process of claim 1 wherein the leaving group is halo, pentafluorophenoxy, a sulfonate, a hydroxyamino, or imidazol-1-yl.

6. The process of claim 1 wherein the base is DBU.

7. The process of claim 1 wherein the halogenating agent is NFSI, F-TEDA, or 1-chloromethyl-4-fluoro-1,4-diazoniabicyclo[2.2.2]octane bis(tetrafluoroborate).

8. The process of claim 1 wherein C is aryl, heteroaryl, arylalkyl, or heteroarylalkyl, each of which is optionally substituted.

9. The process of claim 1 wherein A is $CH_2$.

10. The process of claim 1 wherein B is $(CH_2)_n$ and n is an integer from 2 to 6.

11. The process of claim 1 wherein B is $(CH_2)_n$, and n is 2, 3, or 4.

12. The process of claim 1 wherein B is $(CH_2)_n$, and n is 3.

13. The process of claim 1 wherein $R^{100}$ is acyl.

14. The process of claim 1 wherein $R^{100}$ is alkylcarbonyl or optionally substituted benzoyl.

15. The process of claim 1 wherein $R^{100}$ is acetyl or benzoyl.

16. The process of claim 1 wherein W is H or F.

17. The process of claim 1 wherein W is F.

* * * * *